US012527699B2

(12) United States Patent
Jeon et al.

(10) Patent No.: US 12,527,699 B2
(45) Date of Patent: Jan. 20, 2026

(54) SYSTEM OF A PULL-ON WEARABLE ARTICLE AND AN ABSORBENT ARTICLE

(71) Applicant: Kimberly-Clark Worldwide, Inc., Neenah, WI (US)

(72) Inventors: YangSook Jeon, Dongjak-gu (KR); CheolHee Kim, Suseong-gu (KR); JeongOg Byun, Songpa-gu (KR); JungNam Kim, Dongdaemun-gu (KR); Candace D. Krautkramer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 509 days.

(21) Appl. No.: 17/920,427

(22) PCT Filed: Apr. 30, 2020

(86) PCT No.: PCT/US2020/030746
§ 371 (c)(1),
(2) Date: Oct. 21, 2022

(87) PCT Pub. No.: WO2021/221661
PCT Pub. Date: Nov. 4, 2021

(65) Prior Publication Data

US 2023/0157904 A1 May 25, 2023

(51) Int. Cl.
*A61F 13/49* (2006.01)
*A61F 13/514* (2006.01)

(52) U.S. Cl.
CPC ........ *A61F 13/49* (2013.01); *A61F 13/51496* (2013.01)

(58) Field of Classification Search
CPC .. A61F 13/49; A61F 13/51496; A61F 13/496; A61F 13/84; A61F 13/15268; A61F 2013/15276
See application file for complete search history.

(56) References Cited

U.S. PATENT DOCUMENTS 4,560,381 A * 12/1985 Southwell ............... A61F 13/76 604/396
4,695,279 A 9/1987 Steer
(Continued)

FOREIGN PATENT DOCUMENTS

| | | | |
|---|---|---|---|
| EP | 2301504 | A1 | 3/2011 |
| JP | 2004329272 | A | 11/2004 |
| WO | 2021221660 | A1 | 11/2021 |

OTHER PUBLICATIONS

Transformation Textiles, “EVA Classic Dignity Kit”, Dec. 19, 2019, https://transformation-textiles.myshopify.com/products/10-dignity-kits-eva-classic.

*Primary Examiner* — Susan S Su
*Assistant Examiner* — Erin A Kim
(74) *Attorney, Agent, or Firm* — KIMBERLY-CLARK WORLDWIDE, INC.

(57) ABSTRACT

A pull-on wearable article can have a front region, a back region, and a crotch region located between the front region and the back region. The pull-on wearable article has a permanent closed waist configuration providing the pull-on wearable article with a waist opening and two leg openings. An informational cue can be associated with the pull-on wearable article to communicate to the wearer of the pull-on wearable article where to place the crotch region of an absorbent article when placing the absorbent article into the pull-on wearable article. The informational cue triggers a cognitive response in the wearer of the pull-on wearable article and can be an attention attracting graphic, a textural feature, or a combination of an attention attracting graphic, textural feature, or a combination thereof.

17 Claims, 36 Drawing Sheets

(56) References Cited

U.S. PATENT DOCUMENTS

| | | | |
|---|---|---|---|
| 4,938,753 | A | 7/1990 | Van Gompel et al. |
| 5,269,775 | A | 12/1993 | Freeland et al. |
| 5,650,214 | A | 7/1997 | Anderson et al. |
| 6,102,902 | A | 8/2000 | Jackson |
| 6,193,703 | B1 | 2/2001 | Jackson |
| 6,240,569 | B1 | 6/2001 | Van Gompel et al. |
| 6,287,169 | B1 | 9/2001 | Willms et al. |
| 7,322,966 | B1 | 1/2008 | Deerin |
| 7,553,303 | B2 | 6/2009 | Speak |
| 7,887,522 | B2 | 2/2011 | Roe et al. |
| 8,167,862 | B2 | 5/2012 | Digiacomantonio et al. |
| 9,750,287 | B2 | 9/2017 | Cohen Larren et al. |
| 2003/0158532 | A1 | 8/2003 | Magee et al. |
| 2003/0163104 | A1 | 8/2003 | Tears et al. |
| 2005/0261653 | A1* | 11/2005 | Digiacomantonio ... A61F 13/84 604/385.03 |
| 2006/0069378 | A1 | 3/2006 | Winkel et al. |
| 2006/0149197 | A1 | 7/2006 | Niemeyer |
| 2007/0083181 | A1 | 4/2007 | LaVon et al. |
| 2008/0119816 | A1 | 5/2008 | Carstens |
| 2012/0136330 | A1 | 5/2012 | Schlinz et al. |
| 2014/0018760 | A1 | 1/2014 | Orchard, IV et al. |
| 2014/0257228 | A1* | 9/2014 | Wang .................... A61F 13/505 604/385.14 |
| 2015/0257948 | A1 | 9/2015 | Steele |
| 2018/0055700 | A1 | 3/2018 | Roe et al. |
| 2020/0078233 | A1 | 3/2020 | Hughes et al. |
| 2020/0323702 | A1 | 10/2020 | Arizti et al. |
| 2023/0157904 | A1 | 5/2023 | Jeon et al. |

* cited by examiner

SYSTEM OF A PULL-ON WEARABLE ARTICLE AND AN ABSORBENT ARTICLE

BACKGROUND OF THE DISCLOSURE

Products such as absorbent articles are often used to collect and retain human body exudates containing, for example, urine, menses, and/or blood. Comfort, absorbency, and discretion are three main product attributes and areas of concern for the wearer of the absorbent article. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of absorbent articles for absorption of body exudates are available in the form of feminine pads, sanitary napkins, panty shields, and pantiliners. These absorbent articles generally have an absorbent core positioned between a body-facing liquid permeable topsheet layer and a garment-facing liquid impermeable backsheet layer. The edges of the topsheet layer and the backsheet layer are often bonded together at their periphery to form a seal to contain the absorbent core and body exudates received into the product through the topsheet layer. In use, absorbent articles such as, for example, feminine pads and sanitary napkins are typically positioned in the crotch portion of an undergarment for absorption of the body exudates and a garment attachment adhesive on the backsheet layer can be used to attach the product to the inner crotch portion of the undergarment. Some of these absorbent articles can also include wing-like structures for wrapping about the wearer's undergarment to further secure the product to the undergarment and to protect the undergarment from staining. Such wing-like structures (also known as flaps or tabs) are frequently made from lateral extensions of the topsheet and/or backsheet layers.

Wearers of such absorbent articles, however, desire discretion, comfort, and close to the body fit. Absorbent articles which are attached to a wearer's undergarment may experience twisting, contorting, and shifting out of place as they are subjected to the movement of the wearer's undergarment. Twisting, contorting, and shifting of the absorbent article can be exacerbated by misplacement of the absorbent article into the wearer's undergarment itself. While any wearer of an absorbent article can experience an occasional misplacement of the absorbent article in their undergarment, such misplacement may be a more frequent occurrence for a wearer who may be youthful and early in their menstrual cycle learning process, who may have diminished physical dexterity with their hands, who may have physical dexterity with their hands but have diminished eyesight, and/or who may have mental development disabilities. Misplacement of the absorbent article into the wearer's undergarment can result in misalignment of the crotch region of the absorbent article with the wearer's genital region from which the body exudates will emerge. In such situations, the body exudates will be inefficiently captured by the absorbent article and can result in failure of the absorbent article to capture and contain the body exudates within the absorbent article. The twisting, contorting, and shifting of the misplaced absorbent article can also result in the formation of a gap between the body of the wearer of the absorbent article and the absorbent article itself. The presence of the gap can be a cause of concern to the wearer of the absorbent article due to the lack of a close to the body fit. The presence of the gap can result in a further reduction in the performance of the absorbent article to capture and absorb body exudates directly into the absorbent article.

There is a need for a pull-on wearable article that can assist a wearer of an absorbent article with appropriate placement of the absorbent article into the pull-on wearable article. Such is desirable to provide wearers of absorbent articles with increased peace of mind while wearing the absorbent article regardless of the wearer's physical or mental capabilities.

SUMMARY OF THE DISCLOSURE

In various embodiments, a system of a pull-on wearable article to be worn in combination with an absorbent article can have the pull-on wearable article which can have a longitudinal direction axis and a transverse direction axis; a front region comprising a front waist edge and a back region comprising a back waist edge; a crotch region located between the front region and the back region and comprising a narrowest transverse direction region wherein the narrowest transverse direction region is located between the transverse direction axis and the front waist edge; a permanent closed waist configuration wherein the pull-on wearable article has a waist opening and two leg openings; and a first informational cue positioned in the crotch region, at least a portion of the first informational cue in an overlapping configuration with at least a portion of the narrowest transverse direction region, wherein the first informational cue communicates to a wearer of the pull-on wearable article where to place the absorbent article within the pull-on wearable article; the absorbent article can have a longitudinal direction axis and a transverse direction axis; an anterior region, a posterior region, and a crotch region located between the anterior region and the posterior region; a topsheet layer, a backsheet layer, and an absorbent core positioned between the topsheet layer and the backsheet layer; and a first complementary informational cue located at a mid-point of the crotch region of the absorbent article and associated with the backsheet layer.

In various embodiments, the first informational cue of the pull-on wearable article is internally visible. In various embodiments, the pull-on wearable article further has a second informational cue wherein the second informational cue is located in the front region of the pull-on wearable article. In various embodiments, the pull-on wearable article further has a third informational cue wherein the third informational cue is located in the back region of the pull-on wearable article.

In various embodiments, the pull-on wearable article further has a second informational cue wherein the second informational cue is externally visible.

In various embodiments, the first informational cue of the pull-on wearable article is a graphic. In various embodiments, the first informational cue of the pull-on wearable article is a first textural feature. In various embodiments, the first complementary informational cue of the absorbent article is a second textural feature. In various embodiments, the second textural feature of the absorbent article mates with the first textural feature of the pull-on wearable article to secure the absorbent article within the pull-on wearable article.

In various embodiments, the first informational cue of the pull-on wearable article is a combination of a graphic and a textural feature.

In various embodiments, the first informational cue of the pull-on wearable article is externally visible.

In various embodiments, the pull-on wearable article is durable. In various embodiments, the crotch region of the pull-on wearable article comprises an article body layer. In various embodiments, at least a portion of the crotch region of the pull-on wearable article comprises a wicking layer. In various embodiments, at least a portion of the crotch region of the pull-on wearable article comprises a liquid impermeable barrier layer. In various embodiments, at least a portion of the crotch region of the pull-on wearable article comprises an absorbent layer.

In various embodiments, the absorbent article further has a pair of wings. In various embodiments, the absorbent article further comprises a second complementary informational cue located in the anterior region of the absorbent article and associated with the backsheet layer. In various embodiments, the absorbent article further comprises a third complementary informational cue located in the posterior region of the absorbent article and associated with the backsheet layer.

Figure 1:
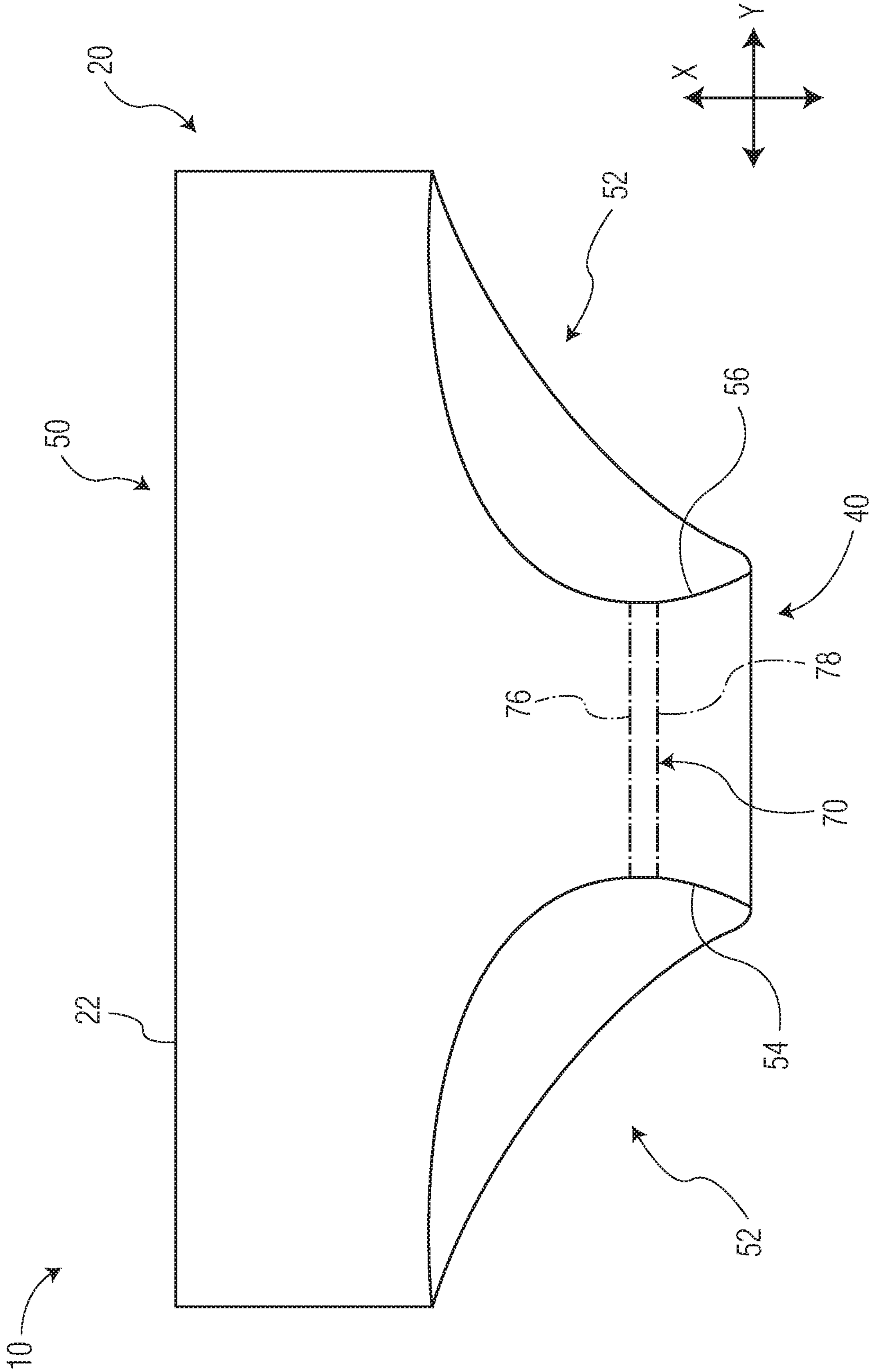
FIG. 1 provides an illustration of an embodiment of a front view of a pull-on wearable article.

Repeat use of reference characters in the present specification and drawings is intended to represent the same or analogous features or elements of the disclosure.

Figure 50:
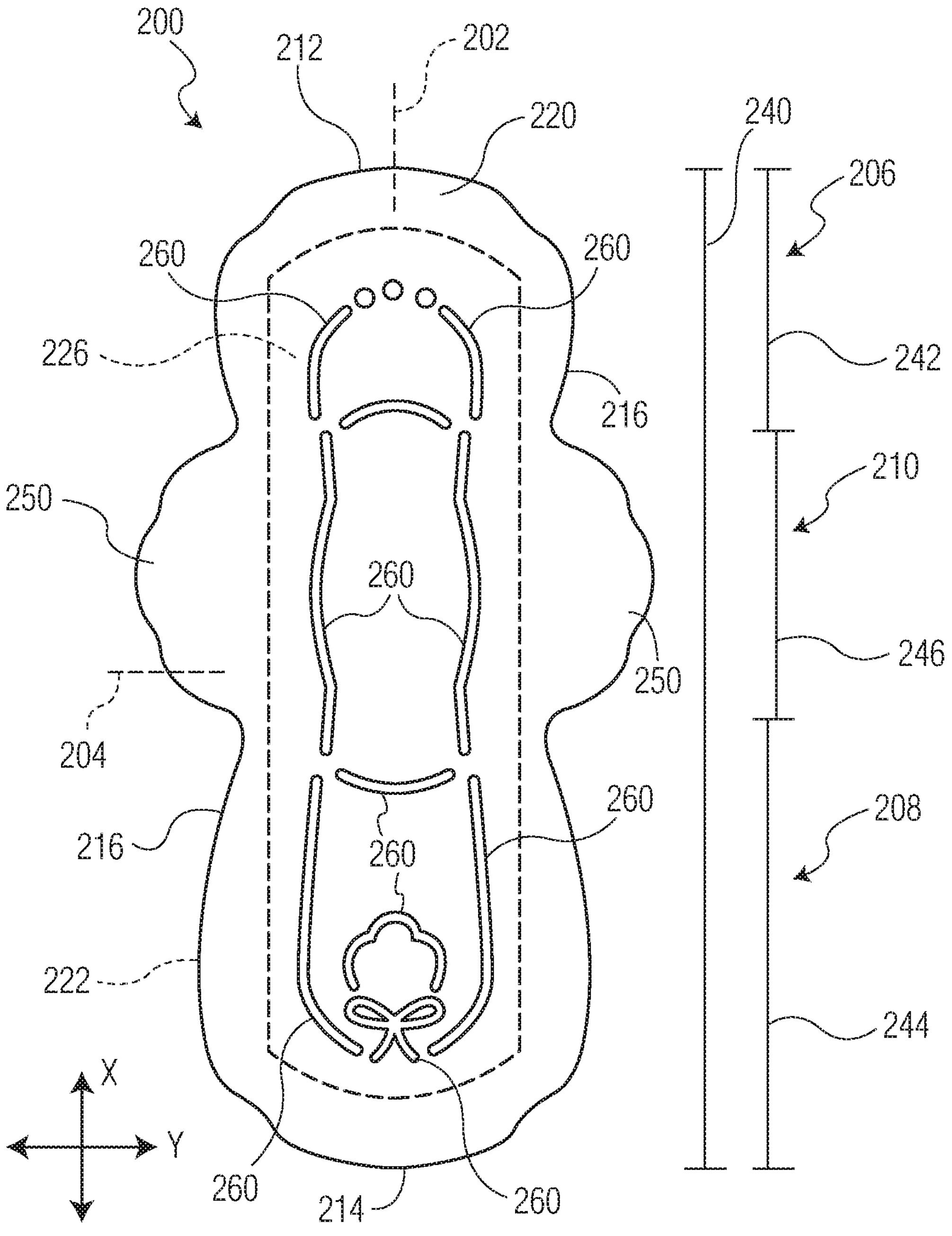

FIG. 50 is a top view of an embodiment of an absorbent article.

DETAILED DESCRIPTION OF THE DISLOSURE

The present disclosure is directed towards a pull-on wearable article which has a front region, a back region, and a crotch region located between the front region and the back region. The pull-on wearable article has a permanent closed waist configuration providing the pull-on wearable article with a waist opening and two leg openings. An informational cue can be associated with the pull-on wearable article to communicate to the wearer of the pull-on wearable article where to place the crotch region of an absorbent article when placing the absorbent article into the pull-on wearable article. The informational cue triggers a cognitive response in the wearer of the pull-on wearable article and can be an attention attracting graphic, textural feature, or a combination thereof.

As used herein, the term "absorbent article" refers herein to an article which may be placed against or in proximity to the body (i.e., contiguous with the body) of the wearer to absorb and contain various liquid, solid, and semi-solid exudates discharged directly from the body. Such absorbent articles, as described herein, are intended to be discarded after a limited period of use instead of being laundered or otherwise restored for reuse. It is to be understood that the present disclosure is applicable to various disposable absorbent articles, including, but not limited to, feminine pads, incontinence pads, sanitary napkins, panty shields, pantiliners, and the like without departing from the scope of the present disclosure.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No.

4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "complementary" refers to filling in or completing such as by overlapping, matching, or aligning therewith; contextually relating, or highlighting.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "externally visible" refers to the ability of a human viewer to visually discern the informational cue with the unaided eye (excepting standard corrective lenses adapted to compensate for near-sightedness, farsightedness, or astigmatism) in standard lighting conditions from a point of reference viewing the non-body facing surface of the pull-on wearable article while the pull-on wearable article is held in a configuration wherein the non-body facing surface is within the field of view.

As used herein, the term "informational cue" refers to distinctive graphic, textural feature, and combinations thereof associated with a pull-on wearable article to provide a functional attribute. The functional attribute includes communicating to the wearer of the pull-on wearable article where to place the crotch region of an absorbent article when placing the absorbent article into the pull-on wearable article. The informational cue triggers a cognitive response in the wearer of the pull-on wearable article.

As used herein, the term "internally visible" refers to the ability of a human viewer to visually discern the informational cue with the unaided eye (excepting standard corrective lenses adapted to compensate for near-sightedness, farsightedness, or astigmatism) in standard lighting conditions from a point of reference viewing the body facing surface of the pull-on wearable article while the pull-on wearable article is held in a configuration wherein the body facing surface is within the field of view.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120, 125, or 150 gsm.

As used herein, the phrase "pull-on" refers to the method of placing a wearable article with a closed waist configuration on a wearer's lower torso region by threading the wearer's legs through the waist opening and leg openings and pulling the wearable article along the legs and over the hips and buttocks of the wearer.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the term "standard lighting conditions" refers to lighting conditions in which the human vision operates efficiently (e.g., the human eye is able to discern complex patterns, shading, and colors). Specifically, for purposes herein, standard lighting conditions are at least one of the following: a) natural illumination as experienced outdoors during daylight hours; b) the illumination of a standard 100 watt incandescent white light bulb at a distance of 2 meters, or c) as defined by CIE D65 standard illuminate lighting at 800 lux to a 1964 CIE standard observer.

As used herein, the terms "superabsorbent polymer," "superabsorbent," or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

As used herein, the phrase "wearable article" refers to an article configured to be worn about the lower torso of the wearer and having a waist opening and a pair of leg openings. In various embodiments, the wearable article may contain an absorbent material. In various embodiments, the wearable article does not contain an absorbent material.

Figure 2:
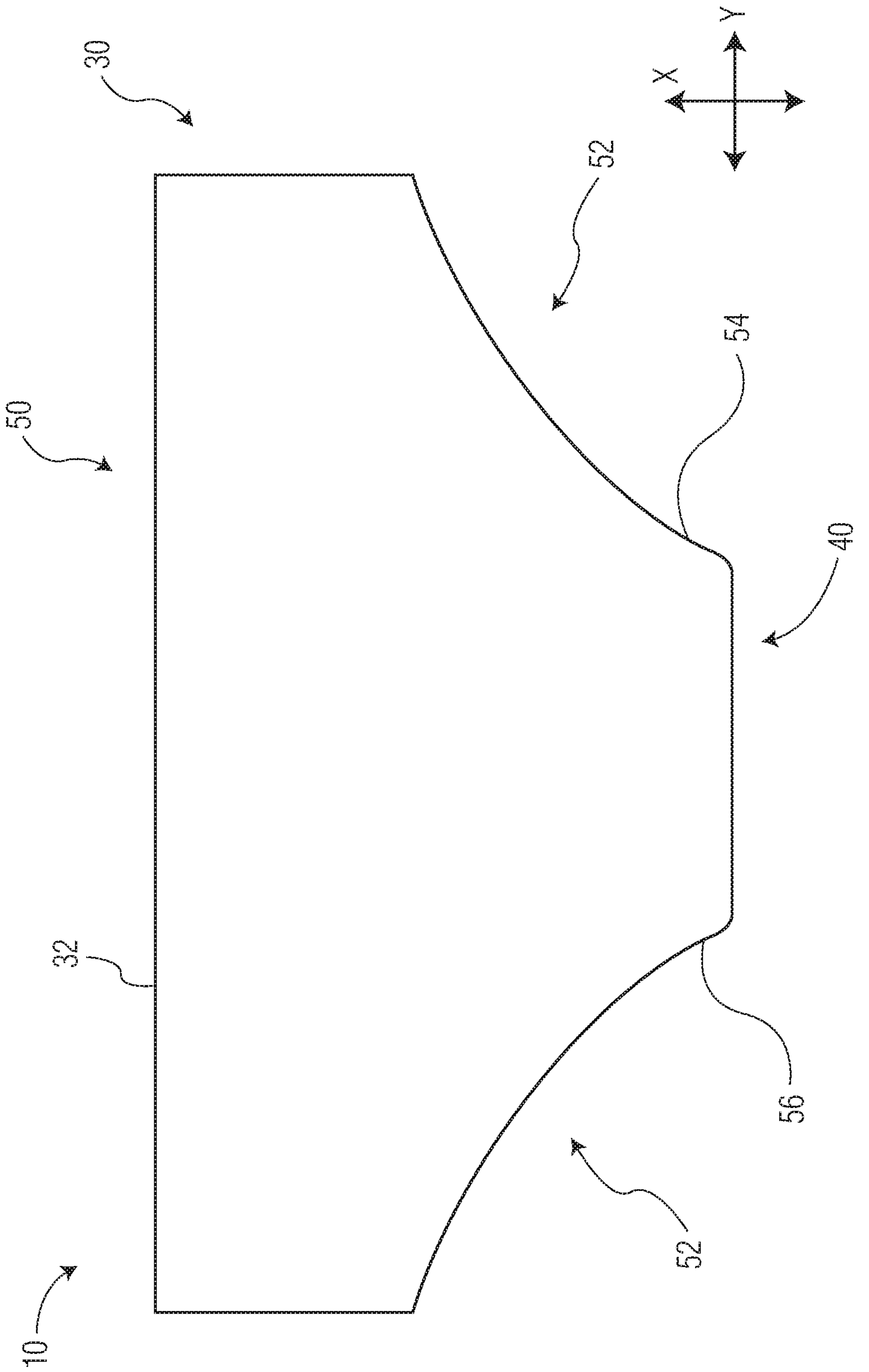
FIG. 2, provides an illustration of a back view of the pull-on wearable article of FIG. 1.
Figure 3:
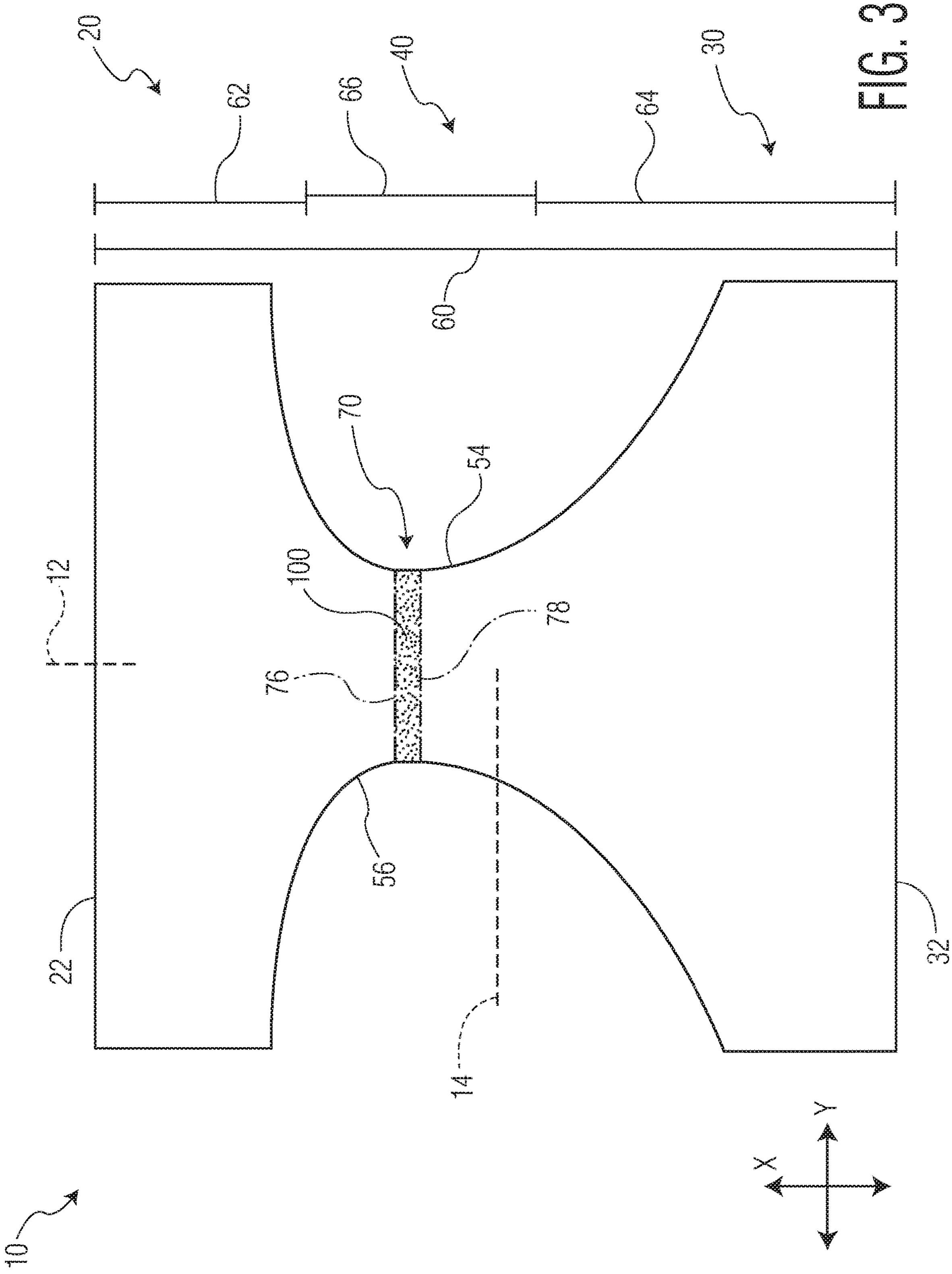
FIG. 3 provides a two-dimensional illustration of a plan view of an embodiment of the pull-on wearable article of FIG. 1 in a longitudinally and transversely stretched and laid-flat configuration with the surface of the pull-on wearable article that faces the wearer when the pull-on wearable article is worn facing the viewer.
Figure 4:
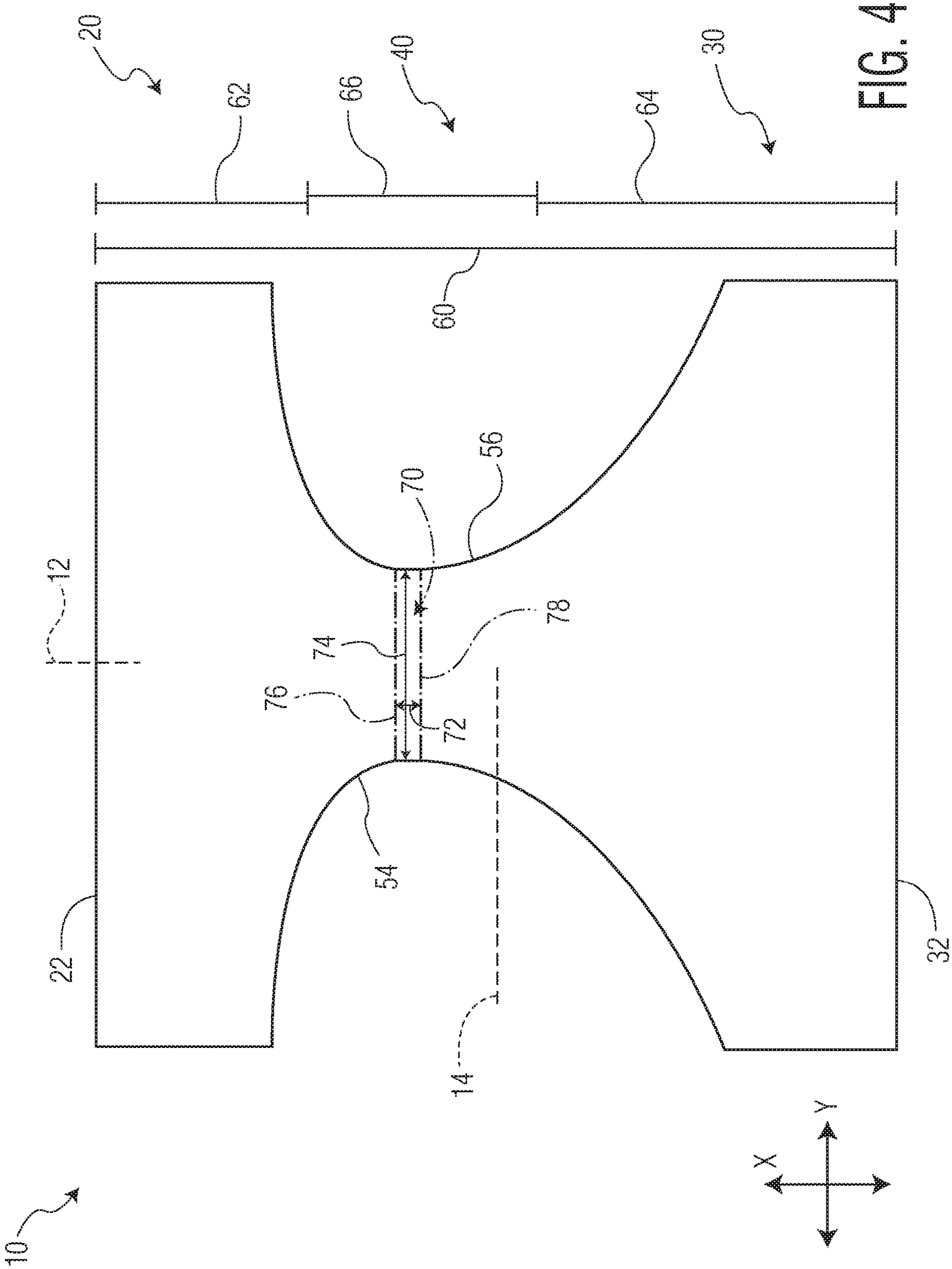
FIG. 4 provides a two-dimensional illustration of a plan view of an embodiment of the pull-on wearable article of FIG. 1 in a longitudinally and transversely stretched and laid-flat configuration with the surface of the pull-on wearable article that faces away from the wearer when the pull-on wearable article is worn facing the viewer.

Referring to FIGS. 1-4, an illustration of an exemplary embodiment of a pull-on wearable article 10 is illustrated. FIG. 1 provides an illustration of an embodiment of a front view of the pull-on wearable article 10 in a closed waist configuration. FIG. 2 provides an illustration of a back view of the pull-on wearable article 10 of FIG. 1 in a closed waist configuration. FIG. 3 provides a two-dimensional schematic of a plan view of an embodiment of the pull-on wearable article 10 of FIG. 1 in a longitudinally and transversely stretched and laid-flat configuration with the surface of the pull-on wearable article 10 that faces the wearer when the pull-on wearable article 10 is worn facing the viewer. FIG. 4 provides a two-dimensional schematic of a plan view of an embodiment of the pull-on wearable article 10 of FIG. 1 in a longitudinally and transversely stretched and laid-flat configuration with the surface of the pull-on wearable article 10 that faces away from the wearer when worn facing the viewer.

The pull-on wearable article 10 has a longitudinal direction (X) and a transverse direction (Y). The pull-on wearable article 10 can have a longitudinal direction axis 12 and a transverse direction axis 14. The pull-on wearable article 10 has a permanent closed waist configuration providing the pull-on wearable article 10 with a waist opening 50 and a pair of leg openings 52. The pull-on wearable article 10 is intended to be worn about the lower torso of a human and has a front region 20, a back region 30, and a crotch region 40 extending between and connecting the front region 20 and the back region 30. The front region 20 and the back region 30 are those regions of the pull-on wearable article 10 that are fitted circumferentially around at least the lower torso of the wearer of the pull-on wearable article 10 including, for example, the wearer's abdomen, lower back, buttock, and hips. The crotch region 40 of the pull-on wearable article 10 is that region of the pull-on wearable article 10 that will be positioned between the wearer's legs when the pull-on wearable article 10 is fitted onto the wearer.

The front region 20 has a front waist edge 22 and the back region 30 has a back waist edge 32. The pull-on wearable article 10 has an article length 60 as measured in the longitudinal direction (X) from the front waist edge 22 to the back waist edge 32 as illustrated in FIG. 3. Each of the front region 20, back region 30, and crotch region 40 can have a length measured in the longitudinal direction (X). The front region 20 can have a front region length 62, as measured from the front waist edge 22 in a direction towards the transverse direction axis 14 and along the longitudinal direction axis 12, that is one-third or less of the article length 60. The back region 30 can have a back region length 64, as measured from the back waist edge 32 in a direction towards the transverse direction axis 14 and along the longitudinal direction axis 12, that is one-third or greater of the article length 60. The crotch region 40 is disposed in the longitudinal direction (X) between and interconnecting the front region 20 and the back region 30. The crotch region 40 can have a crotch region length 66, as measured in the longitudinal direction (X) and along the longitudinal direction axis 12, that is one-third or less of the article length 60. In various embodiments, the front region length 62, the back region length 64, and the crotch region length 66 are the same. In various embodiments, the back region length 64 is greater than each of the front region length 62 and the crotch region length 66 while the crotch region length 66 is the same as the front region length 62. In various embodiments, the back region length 64 is greater than each of the front region length 62 and the crotch region length 66 while the crotch region length 66 is also greater than the front region length 62. In various embodiments, the back region length 64 is greater than each of the front region length 62 and the crotch region length 66 while the front region length 64 is also greater than the crotch region length 66.

The pull-on wearable article 10 can have a narrowest transverse direction region 70 located within the crotch region 40. The narrowest transverse direction region 70 can be defined by a leading transverse direction boundary 76, a trailing transverse direction boundary 78, and a portion of each of the first leg edge 54 and the second leg edge 56. The narrowest transverse direction region 70 can have both a longitudinal direction length dimension 72 and a transverse direction width dimension 74. The transverse direction width dimension 74 is measured in the transverse direction (Y) as the narrowest width measurement in the crotch region 40 between the first leg edge 54 and the second leg edge 56 such as illustrated in FIG. 4. The leading transverse direction boundary 76 is located between the front waist edge 22 and the trailing transverse direction boundary 78 while the trailing transverse direction boundary 78 is located between the back waist edge 32 and the leading transverse direction boundary 76. The leading transverse direction boundary 76 and the trailing transverse direction boundary 78 are each defined when the transverse direction (Y) width measurement between the first leg edge 54 and the second leg edge 56, as measured along the longitudinal direction axis 12, begins to increase over the narrowest transverse direction width dimension 74 as measured between the first leg edge 54 and the second leg edge 56. The leading transverse direction boundary 76 and the trailing transverse direction boundary 78 will each have a transverse direction (Y) width dimension which is the same as the narrowest transverse direction width dimension 74. The longitudinal direction length dimension 72 of the narrowest transverse direction region 70 is measured in the longitudinal direction (X) along the longitudinal direction axis 12 and is measured as the distance between the leading transverse direction boundary 76 and the trailing transverse direction boundary 78 of the narrowest transverse direction region 70. In various embodiments, the narrowest transverse direction region 70 is positioned between the front waist edge 22 and the transverse direction axis 14 of the absorbent article 10. In such embodiments, the narrowest transverse direction region 70 is not in an overlapping alignment with the transverse direction axis 14 of the pull-on wearable article 10. Wearers of pull-on wearable articles 10 have body shapes in a variety of shapes, sizes, and curvature, and are generally not symmetrical. Placing a symmetrical about the transverse direction axis 14 pull-on wearable article 10 on a body which is not symmetrical can result in a reduction in the proper fit of the pull-on wearable article 10 on the body of the wearer. Positioning the narrowest transverse direction region 70 closer to the front waist edge 22, and not in an overlapping alignment with the transverse direction axis 14, can provide for a non-symmetrical about the transverse direction axis 14 pull-on wearable article 10. As a result, when the narrowest transverse direction region 70 is positioned between the legs of the wearer, a greater proportion of the pull-on wearable article 10 is positioned on the posterior side of the wearer's body providing for better coverage of the buttocks of the wearer of the pull-on wearable article 10.

In various embodiments, a single layer of material can form each of the front region 20, back region 30, and crotch region 40 of the pull-on wearable article 10. In various embodiments, a first portion of the pull-on wearable article 10 can have a single layer of material and a second portion of the pull-on wearable article 10 can have at least two layers of material. In various embodiments, a first portion of the pull-on wearable article 10 can have a single layer of material and a second portion of the pull-on wearable article 10 can have at least three layers of material. In various embodiments, a first portion of the pull-on wearable article 10 can have a single layer of material and a second portion of the pull-on wearable article 10 can have at least four layers of material.

In various embodiments, at least two layers of material can form at least portions of each of the front region 20, back region 30, and crotch region 40 of the pull-on wearable article 10. In various embodiments, a first portion of the pull-on wearable article 10 can be formed of two layers of material and a second portion of the pull-on wearable article 10 can be formed of at least three layers of material. In various embodiments, a first portion of the pull-on wearable article 10 can be formed of two layers of material and a second portion of the pull-on wearable article 10 can be formed of at least four layers of material.

In various embodiments, at least three layers of material can form at least portions of each of the front region 20, back region 30, and crotch region 40 of the pull-on wearable article 10. In various embodiments, a first portion of the pull-on wearable article 10 can be formed of three layers of material and a second portion of the pull-on wearable article 10 can be formed of at least four layers of material. In various embodiments, at least four layers of material can form at least portions of each of the front region 20, back region 30, and crotch region 40 of the pull-on wearable article 10.

In various embodiments, the pull-on wearable article 10 is a durable article which is intended to be laundered or otherwise restored or reused as a wearable article. In such embodiments, the materials forming the pull-on wearable article 10 can be selected for their ability to withstand the laundering process including, but not limited to, washing and/or drying.

The material forming any portion of a layer of the pull-on wearable article 10 can be selected from, but not limited to, for example, a cotton material, a cotton blend material, a synthetic material, an elasticized blend material (e.g., elastane or spandex), a thermoplastic or thermoset film (e.g., polyurethane, polyester, polyolefin, or silicone), a foam material, a polyamide material, a polyester material, a polyolefin material, a polyurethane material, a polyacrylonitrile material, a natural cellulose material, a regenerated cellulose material, a regenerated cellulose derivative material (e.g., cellulose acetate and cellulose triacetate), natural protein and regenerated protein materials, and the like, or a blend of such materials. When the pull-on wearable article 10 is formed of a single layer of material, the article body layer of the pull-on wearable article 10 can be selected from, for example, but not limited to, a cotton material, a cotton blend material, a synthetic material, an elasticized blend material (e.g., elastane or spandex), or any other material (e.g., a natural or manmade synthetic material).

When a portion of the pull-on wearable article 10 has more than one layer of material, the outermost layer of material can be as described for a pull-on wearable article 10 formed of only a single layer of material, while each inner (i.e., closer to the body of the wearer) layer of material can perform a specific function for the pull-on wearable article 10 and can be formed of a material specific to that function. In various embodiments, an outer layer of material of a pull-on wearable article 10 can be an article body layer. In various embodiments, an inner layer of material of a pull-on wearable article 10 can be a liquid impermeable barrier layer, an absorbent layer, or a wicking layer.

For example, an inner layer of material of a pull-on wearable article 10 can be a liquid impermeable barrier layer to prevent any body exudate leaking from an absorbent article and onto the pull-on wearable article 10 from escaping the pull-on wearable article 10 and staining the wearer's outer clothes. The liquid impermeable barrier layer can be any material that is heat stable up to at least 190° C. In various embodiments, the liquid impermeable barrier layer can be a lightweight tightly knitted/woven fabric coated with superabsorbent material/hydrogel, or the liquid impermeable barrier layer can be a lightweight tightly knitted/woven fabric made using textile/superabsorbent hybrid fibers, or can be a liquid-proof membrane. In various embodiments, the liquid impermeable barrier layer can be selected from, for example, any wholly or partially liquid-blocking material such as a thermoplastic or thermoset film (e.g., polyurethane, polyester, polyolefin, and silicone). In various embodiments, the liquid impermeable barrier layer can be formed from a thermoplastic polyurethane film.

For example, an inner layer of material of a pull-on wearable article 10 can be an absorbent layer to absorb any body exudate leaking from an absorbent article and onto the pull-on wearable article 10. The absorbent layer can be a material such as, but not limited to, any liquid absorbent material such as, for example, cotton, cotton blend, foam, synthetic material, absorbent polymeric foam, a nanotechnology based or produced material, or any other moisture absorbent material. For example, the absorbent layer can be a polyester:nylon fabric with a microfiber double terry knit. For example, the absorbent layer can be polypropylene or any cellulose-based fabric and their blends including cotton, bamboo, etc. For example, the absorbent layer can be a 100% polyester double terry fabric. For example, the absorbent layer can be made from a blended fiber containing two or more of superabsorbent material, hydrogel, and polyester, or at least a portion of the absorbent layer may be treated with a superabsorbent material or a hydrogel.

For example, an inner layer of material of a pull-on wearable article 10 can be a wicking layer that can draw in any body exudate leaking from an absorbent article and transfer the leaked body exudate to another layer of the pull-on wearable article 10 such as, for example, but not limited to, an absorbent layer. The wicking layer can be formed from a material such as, but not limited to, polyamide, polyester, polyolefin, polyurethane, polyacrylonitrile, natural cellulose, regenerated cellulose, regenerated cellulose derivatives (e.g. cellulose acetate or cellulose triacetate), natural protein, and regenerated protein. The wicking layer can be produced using technologies such as knitting (warp knitting such as raschel Tricot, weft knitting such as circular or flat), weaving, non-woven methods (e.g., blow spinning, staple nonwoven, spunlaid, airlaid, needle punched, thermal bonded, hydro-entangled, chemical bonded, etc.), electro-spinning, force-spinning, etc. In various embodiments, the wicking layer can be treated to include a coating, treatment encapsulation or entrapment, to enhance its liquid and moisture management functionality, such as rate of absorbency/wicking, absorption capacity, rate of spreading and distribution, one-way liquid transport, etc. The wicking layer can be naturally wicking material, may be naturally moisture-wicking and/or be treated to become moisture-wicking. For example, in various embodiments, the wicking layer can be a 100% polyester fabric with French terry knit and a denier differential across the two faces of the fabric that assists in moving the liquid from the body facing side of the fabric to the non-body facing side of the fabric. Additional examples of wicking layer material include, but are not limited to, blends of polyester, polypropylene, and/or cotton. For example, in various embodiments, the wicking layer can be formed of a material that is at least 51% cotton and either or both of the body facing surface and/or the non-body facing surface of the wicking layer may be treated with a hydrophilic composition or material (e.g., polyethylene oxide, polyvinyl alcohol, polyacrylamide, polyacrylic acid, polyvinyl pyrrolidone, hydrophilic silicones, or hydrophilic polyurethanes) and/or a hydrophobic composition or material (e.g., silicones, polyfluoroalkylacrylates, polyacrylates, polyurethanes, or waxes) to create a net hydrophilic gradient over the wicking layer.

In various embodiments, a pull-on wearable article 10 can have an article body layer 80 forming the front region 20, back region 30, and crotch region 40 of the pull-on wearable article 10. In various embodiments, a liquid impermeable barrier layer 82 can be positioned in at least a portion of the crotch region 40, in at least a portion of the back region 30, in at least a portion of the crotch region 40 and at least a portion of the back region 30, or in at least a portion of each of the crotch region 40, back region 30, and the front region 20. In various embodiments, a wicking layer 84 can be positioned in at least a portion of the crotch region 40, in at least a portion of the back region 30, in at least a portion of the crotch region 40 and at least a portion of the back region 30, or in at least a portion of each of the crotch region 40, back region 30, and the front region 20. In various embodiments, an absorbent layer 86 can be positioned in at least a portion of the crotch region 40, in at least a portion of the back region 30, in at least a portion of the crotch region 40 and at least a portion of the back region 30, or in at least a portion of each of the crotch region 40, back region 30, and the front region 20.

In various embodiments wherein the pull-on wearable article 10 has a liquid impermeable layer 82, a wicking layer 84, and/or an absorbent layer 86 forming an inner layer of the pull-on wearable article 10, the liquid impermeable layer 82, the wicking layer 84, and/or the absorbent layer 86 can have any dimension deemed suitable. In various embodiments, when present, a liquid impermeable layer 82, a wicking layer 84, and/or an absorbent layer 86 can have the same dimension as the article body layer 80. In various embodiments, when present, a liquid impermeable layer 82, a wicking layer 84, and/or an absorbent layer 86 can have a dimension smaller than the article body layer 80. In various embodiments, when present in at least a portion of the crotch region 40, a liquid impermeable layer 82, a wicking layer 84, and/or an absorbent layer 86 can have a dimension that is the same as or smaller than the dimension of the portion of the article body layer 80 within the crotch region 40. In various embodiments, when present in at least a portion of the back region 30, a liquid impermeable layer 82, a wicking layer 84, and/or an absorbent layer 86 can have a dimension that is the same as or smaller than the dimension of the portion of the article body layer 80 within the back region 30. In various embodiments, when present in at least a portion of the front region 20, a liquid impermeable layer 82, a wicking layer 84, and/or an absorbent layer 86 can have a dimension that is the same as or smaller than the dimension of the portion of the article body layer 80 within the front region 20. In various embodiments, when present in at least a portion of the crotch region 40 and at least a portion of the back region 30, a liquid impermeable layer 82, a wicking layer 84, and/or an absorbent layer 86 can have a first portion that has a dimension that is the same as or smaller than the dimension of the portion of the article body layer 80 within the crotch region 40 and can have a second portion that has a dimension that is the same as or smaller than the dimension of the portion of the article body layer 80 within the back region 30. In various embodiments, when present in at least a portion of the crotch region 40, a portion of the back region 30, and a portion of the front region 20, a liquid impermeable layer 82, a wicking layer 84, and/or an absorbent layer 86 can have a first portion that has a dimension that is the same as or smaller than the dimension of the portion of the article body layer 80 within the crotch region 40, can have a second portion that has a dimension that is the same as or smaller than the dimension of the portion of the article body layer 80 within the back region 30, and can have a third portion that has a dimension that is the same as or smaller than the dimension of the portion of the article body layer 80 within the front region 20.

Referring to FIGS. 3-26, various illustrations of exemplary embodiments of pull-on wearable articles 10 are shown in which the pull-on wearable article 10 can be formed of a single layer of material or in which at least a portion of the pull-on wearable article 10 can be formed of an outer layer of material and at least 1 inner layer of material.

Figure 10:
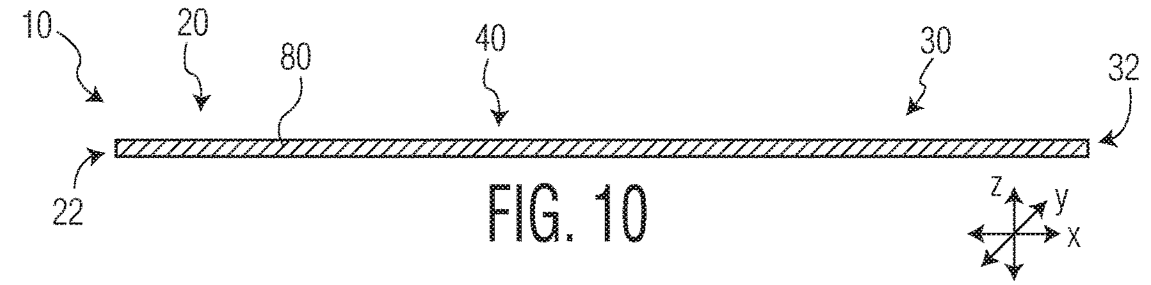
FIGS. 10-26 are cross-sectional illustrations of alternate embodiments of the pull-on wearable article taken along the longitudinal direction axis of the pull-on wearable article.
Figure 23:
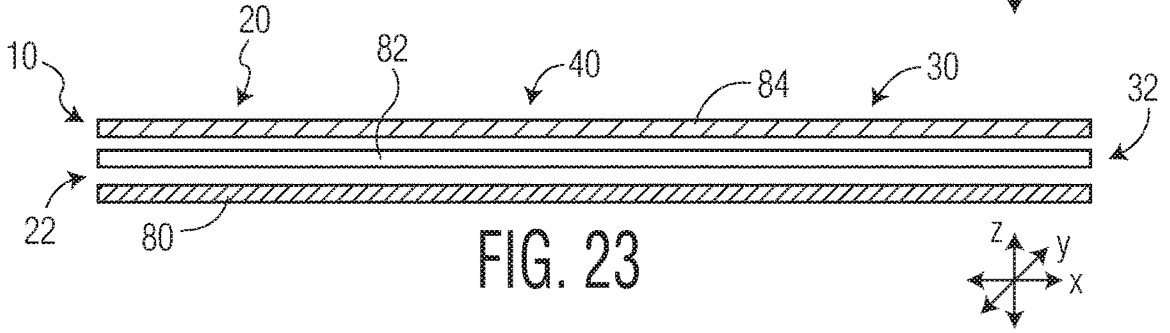
Figure 26:
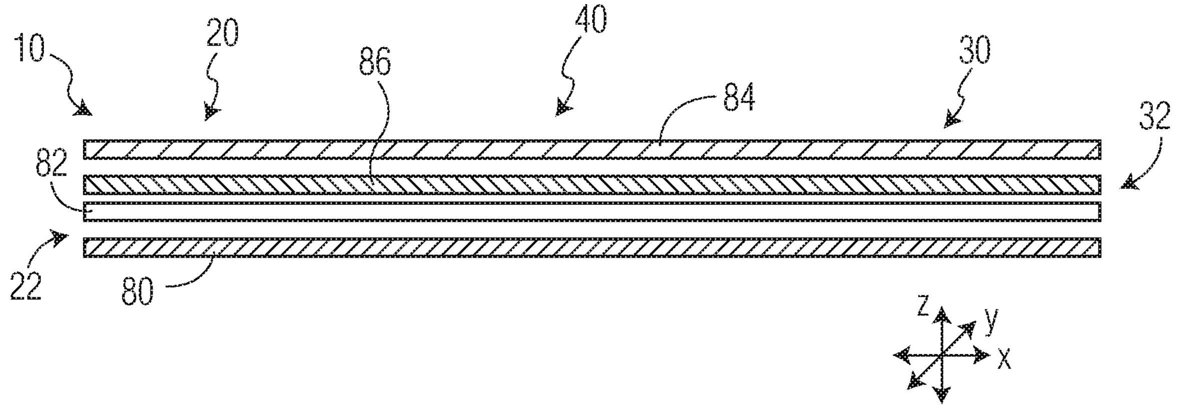

FIG. 3 provides a two-dimensional schematic of a plan view of an embodiment of the pull-on wearable article 10 of FIG. 1 in a longitudinally and transversely stretched and laid-flat configuration with the surface of the pull-on wearable article 10 that faces the wearer when the pull-on wearable article 10 is worn facing the viewer. FIG. 4 provides a two-dimensional schematic of a plan view of an embodiment of the pull-on wearable article 10 of FIG. 1 in a longitudinally and transversely stretched and laid-flat configuration with the surface of the pull-on wearable article 10 that faces away from the wearer when worn facing the viewer. The pull-on wearable article 10 of FIGS. 3 and 4 can be formed of at least 1, 2, 3, or 4 layers of material wherein each layer of material extends from the front waist edge 22 to the back waist edge 32 of the pull-on wearable article 10. Examples of such constructions can be seen in the exemplary embodiments illustrated in FIGS. 10, 23, and 26. FIG. 10 provides a cross-sectional illustration of an exemplary embodiment of the pull-on wearable article 10 of FIG. 3, taken along the longitudinal direction axis 12, wherein the pull-on wearable article 10 is formed of a single layer of material, such as, for example, an article body layer 80. FIG. 23 provides a cross-sectional illustration of another exemplary embodiment of the pull-on wearable article 10 of FIG. 3, taken along the longitudinal direction axis 12, wherein the pull-on wearable article 10 is formed of three layers of material, an article body layer 80, a liquid impermeable barrier layer 82, and a wicking layer 84. FIG. 26 provides a cross-sectional illustration of another exemplary embodiment of the pull-on wearable article 10 of FIG. 3, taken along the longitudinal direction axis 12, wherein the pull-on wearable article 10 is formed of four layers of material, an article body layer 80, a liquid impermeable barrier layer 82, an absorbent layer 86, and a wicking layer 84. Each of the liquid impermeable barrier layer 82, absorbent layer 86, and wicking layer 84, when each layer is present, can have a dimension within each of the front region 20, back region 30, and crotch region 40 that can be equal to or less than the dimension of the article body layer 80 within the each of the front region 20, back region 30, and crotch region 40 of the pull-on wearable article 10. For the exemplary embodiment illustrated in FIGS. 3 and 4, the dimensions of each of the liquid impermeable barrier layer 82, wicking layer 84, and absorbent layer 86, when present, have the same dimension as the article body layer 80 in each of the front region 20, back region 30, and crotch region 40 of the pull-on wearable article 10.

Figure 5:
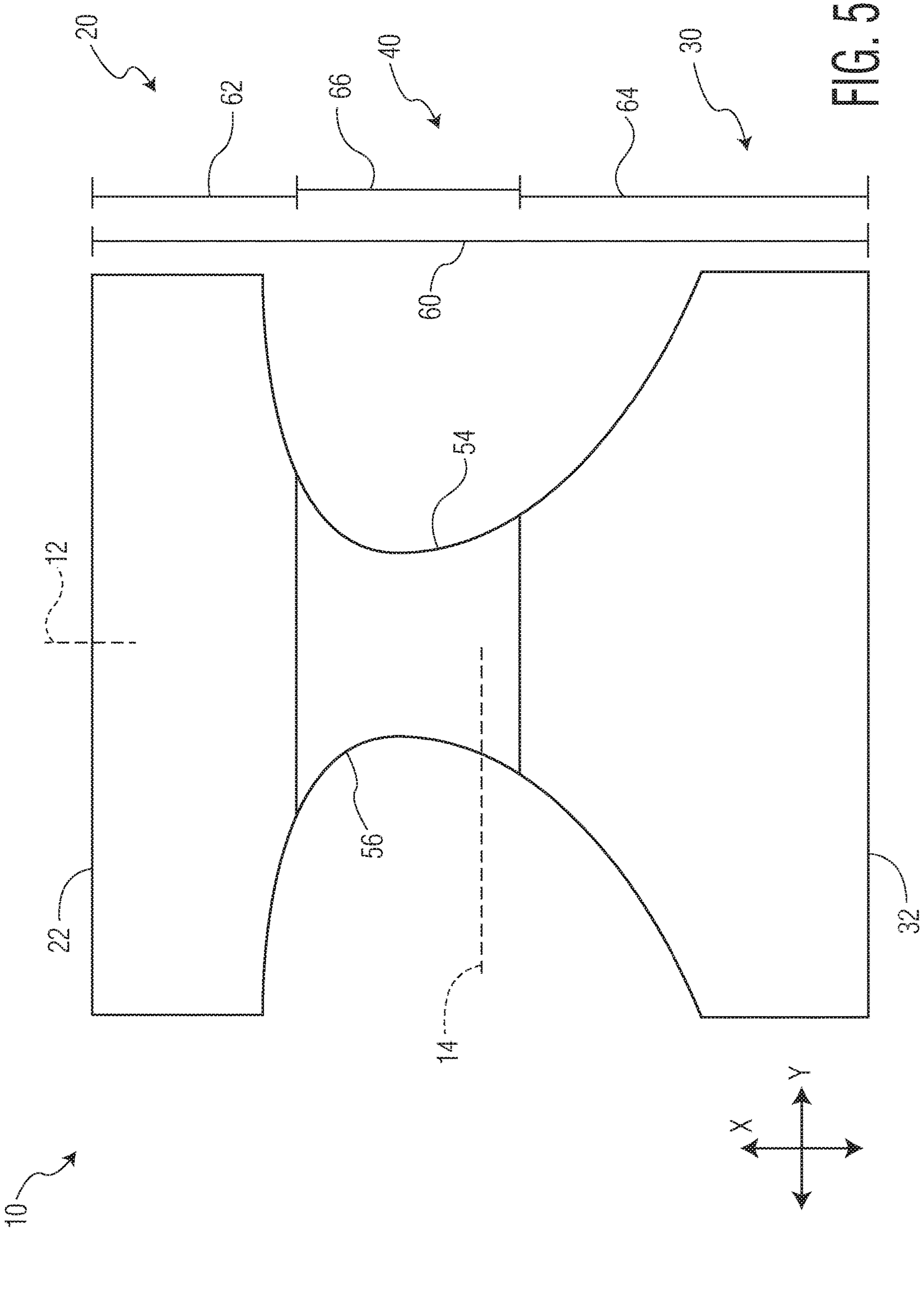
FIGS. 5-9 are two-dimensional illustrations of plan views of alternate embodiments of the pull-on wearable article in a longitudinally and transversely stretched and laid-flat configuration with the surface of the pull-on wearable article that faces the wearer when the pull-on wearable article is worn facing the viewer.
Figure 11:
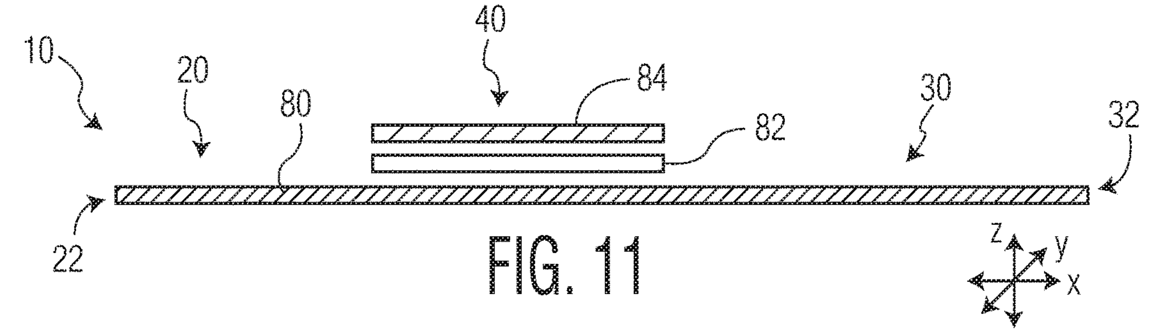
Figure 12:
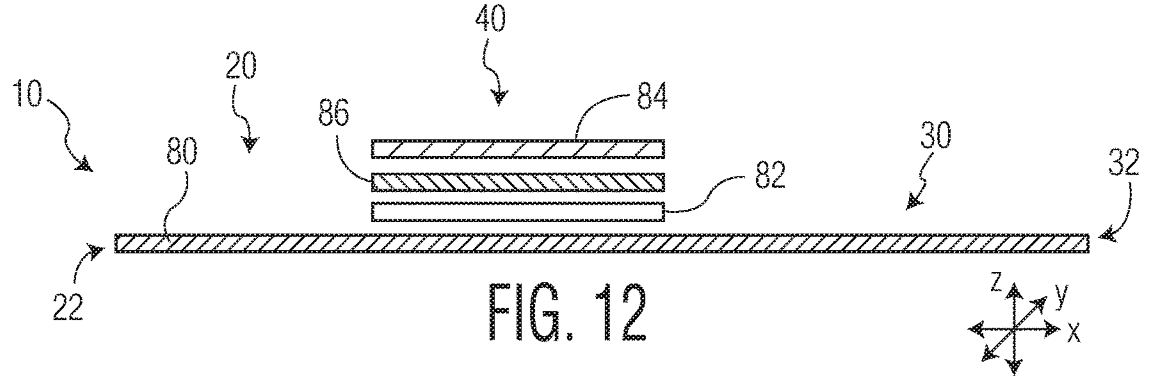

FIG. 5 provides a two-dimensional schematic of a plan view of another embodiment of the pull-on wearable article 10 of FIG. 1 in a longitudinally and transversely stretched and laid-flat configuration with the surface of the pull-on wearable article 10 that faces the wearer when the pull-on wearable article 10 is worn facing the viewer. At least a portion of the crotch region 40 of the pull-on wearable article 10 of FIG. 5 can be formed of at least 2, 3, or 4 layers of material while each of the front region 20 and the back region 30 of the pull-on wearable article 10 of FIG. 5 is formed of a single layer of material. Examples of such constructions can be seen in the exemplary embodiments illustrated in FIGS. 11 and 12. FIG. 11 provides a cross-sectional illustration of an exemplary embodiment of the pull-on wearable article 10 of FIG. 5, taken along the longitudinal direction axis 12, wherein the pull-on wearable article 10 is formed of a single layer of material, an article body layer 80, in each of the front region 20 and the back region 30 and is formed of three layers of material, an article body layer 80, a liquid impermeable barrier layer 82, and a wicking layer 84, in at least a portion of the crotch region 40. FIG. 12 provides a cross-sectional illustration of another exemplary embodiment of the pull-on wearable article 10 of FIG. 5, taken along the longitudinal direction axis 12, wherein the pull-on wearable article 10 is formed of a single layer of material, an article body layer 80, in each of the front region 20 and back region 30 and is formed of four layers of material, an article body layer 80, a liquid impermeable barrier layer 82, an absorbent layer 86, and a wicking layer 84, in at least a portion of the crotch region 40. Each of the liquid impermeable barrier layer 82, absorbent layer 86, and wicking layer 84, when each layer is present, can have a dimension within the crotch region 40 that can be equal to or less than the dimension of the article body layer 80 within the crotch region 40 of the pull-on wearable article 10. For the exemplary embodiment illustrated in FIG. 5, the dimensions of each of the liquid impermeable barrier layer 82, wicking layer 84, and absorbent layer 86, when present, have the same dimension as the article body layer 80 in the crotch region 40 of the pull-on wearable article 10.

Figure 6:
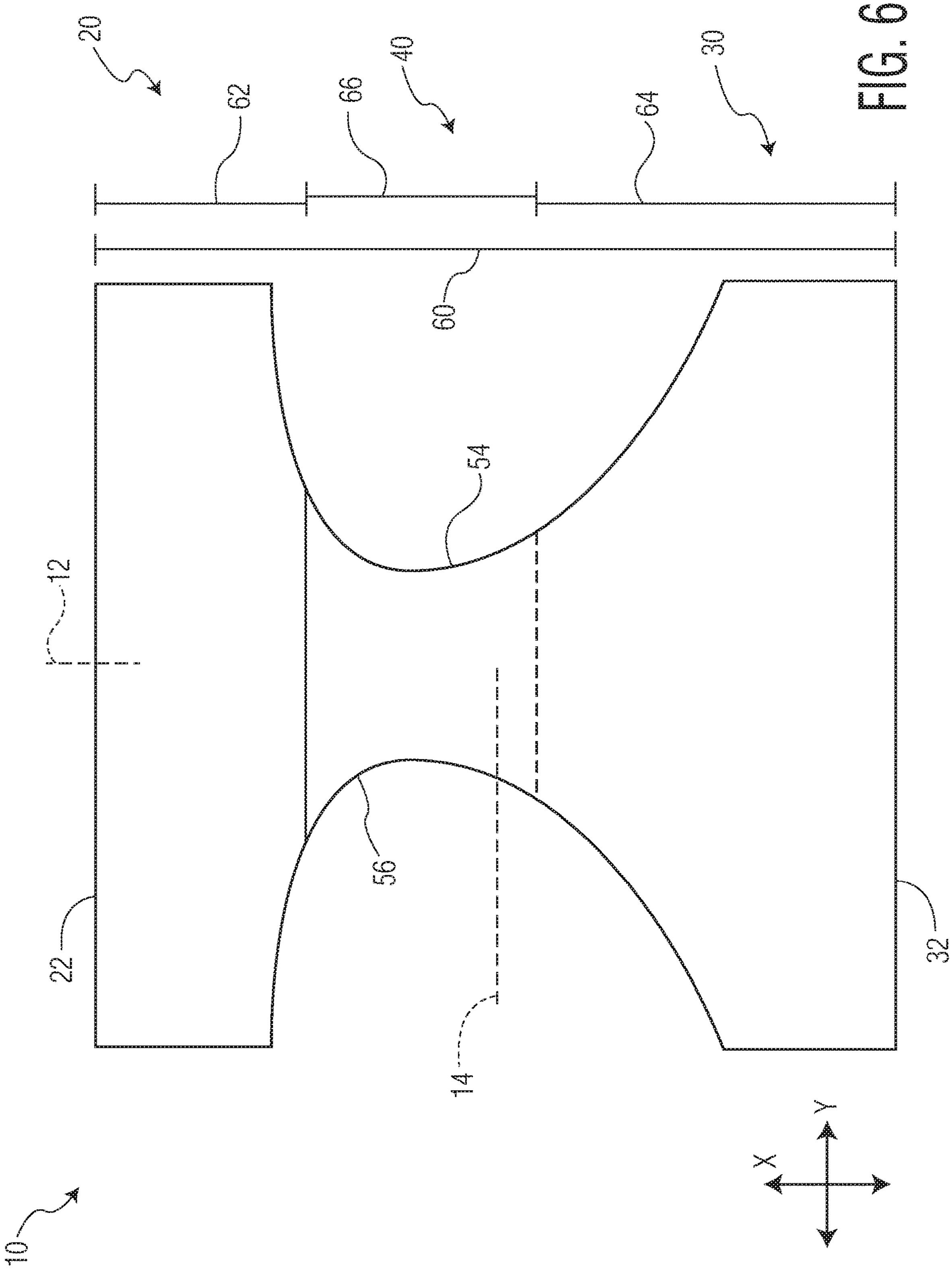
Figure 13:
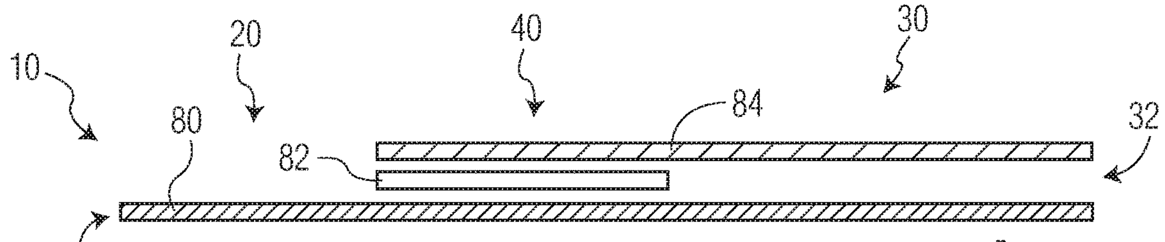
Figure 14:
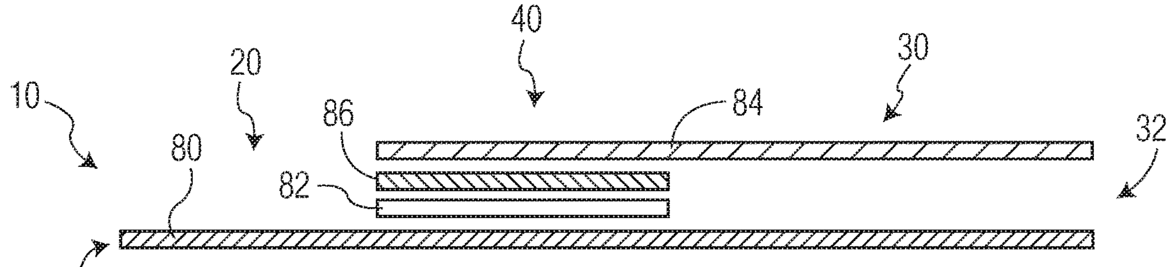
Figure 16:
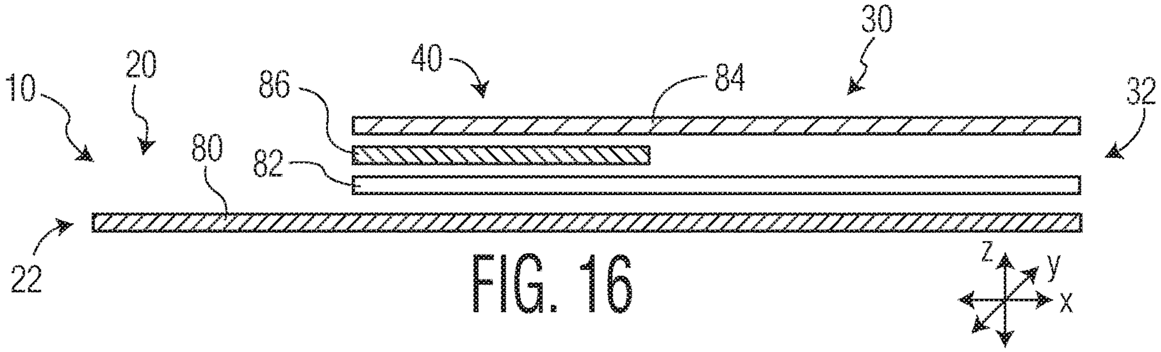

FIG. 6 provides a two-dimensional schematic of a plan view of another embodiment of the pull-on wearable article 10 of FIG. 1 in a longitudinally and transversely stretched and laid-flat configuration with the surface of the pull-on wearable article 10 that faces the wearer when the pull-on wearable article 10 is worn facing the viewer. At least a portion of the crotch region 40 of the pull-on wearable article 10 of FIG. 6 can be formed of at least 3 or 4 layers of material while at least a portion of the back region 30 of the pull-on wearable article 10 of FIG. 6 is formed of 2 or 3 layers of material and the front region 20 of the pull-on wearable article 10 of FIG. 6 is formed of a single layer of material. Examples of such constructions can be seen in the exemplary embodiments illustrated in FIGS. 13, 14, and 16. FIG. 13 provides a cross-sectional illustration of an exemplary embodiment of the pull-on wearable article 10 of FIG. 6, taken along the longitudinal direction axis 12, wherein the pull-on wearable article 10 is formed of a single layer of material, an article body layer 80, in the front region 20, three layers of material, an article body layer 80, a liquid impermeable barrier layer 82, and a wicking layer 84 in at least a portion of the crotch region 40, and two layers of material, an article body layer 80 and a wicking layer 84, in at least a portion of the back region 30 of the pull-on wearable article 10. FIG. 14 provides a cross-sectional illustration of another exemplary embodiment of the pull-on wearable article 10 of FIG. 6, taken along the longitudinal direction axis 12, wherein the pull-on wearable article 10 is formed of a single layer of material, an article body layer 80, in the front region 20, four layers of material, an article body layer 80, a liquid impermeable barrier layer 82, an absorbent layer 86, and a wicking layer 84, in at least a portion of the crotch region 40, and two layers of material, an article body layer 80 and a wicking layer 84 in at least a portion of the back region 30 of the pull-on wearable article 10. FIG. 16 provides a cross-sectional illustration of another exemplary embodiment of the pull-on wearable article 10 of FIG. 6, taken along the longitudinal direction axis 12, wherein the pull-on wearable article 10 is formed of a single layer of material, an article body layer 80, in the front region 20, four layers of material, an article body layer 80, a liquid impermeable barrier layer 82, an absorbent layer 86, and a wicking layer 84, in at least a portion of the crotch region 40, and three layers of material, an article body layer 80, a liquid impermeable barrier layer 82, and a wicking layer 84, in at least a portion of the back region 30 of the pull-on wearable article 10. When the absorbent layer 86 is present, it can have a dimension within the crotch region 40 that can be equal to or less than the dimension of the article body layer 80 within the crotch region 40 of the pull-on wearable article 10. When the liquid impermeable barrier layer 82 is present in only the crotch region 40, it can have a dimension equal to or less than the dimension of the article body layer 80 within the crotch region 40. When the liquid impermeable barrier layer 82 is present in at least a portion of each of the crotch region 40 and the back region 30, it can have a portion within the crotch region 40 that has a dimension which is the same as or less than the dimension of the article body layer 80 within the crotch region 40 and can have a second portion within the back region 30 that has a dimension which is equal to or less than the dimension of the article body layer 80 within the back region 30. When the wicking layer 84 is present in at least a portion of each of the crotch region 40 and the back region 30, it can have a first portion within the crotch region 40 that has a dimension which is the same as or less than the dimension of the article body layer 80 within the crotch region 40 and can have a second portion within the back region 30 that has a dimension which is equal to or less than the dimension of the article body layer 80 within the back region 30.

Figure 7:
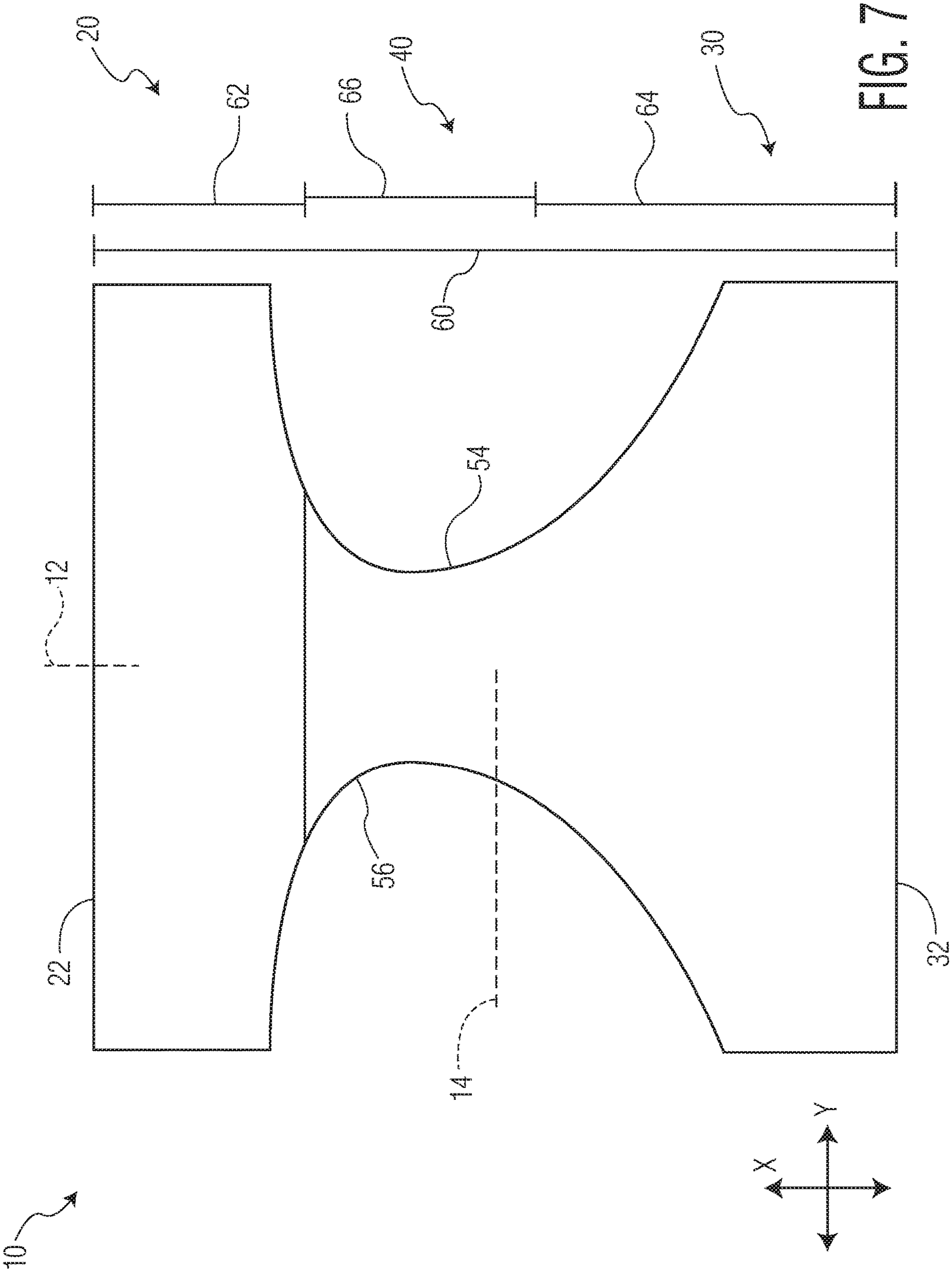
Figure 15:
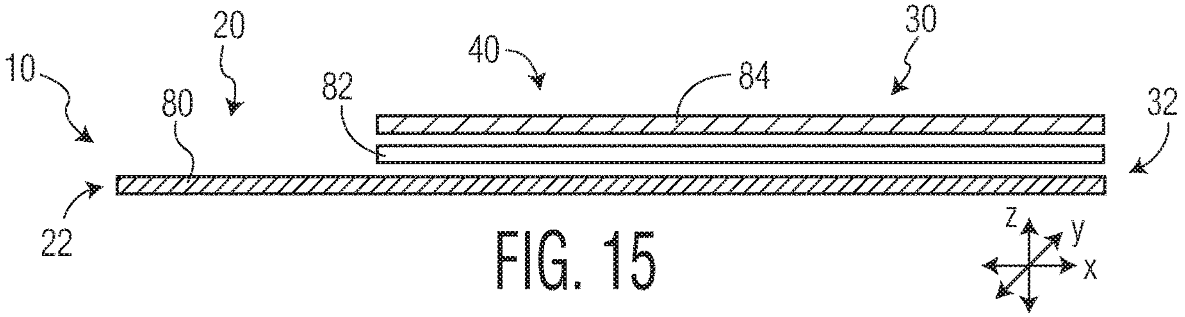
Figure 17:
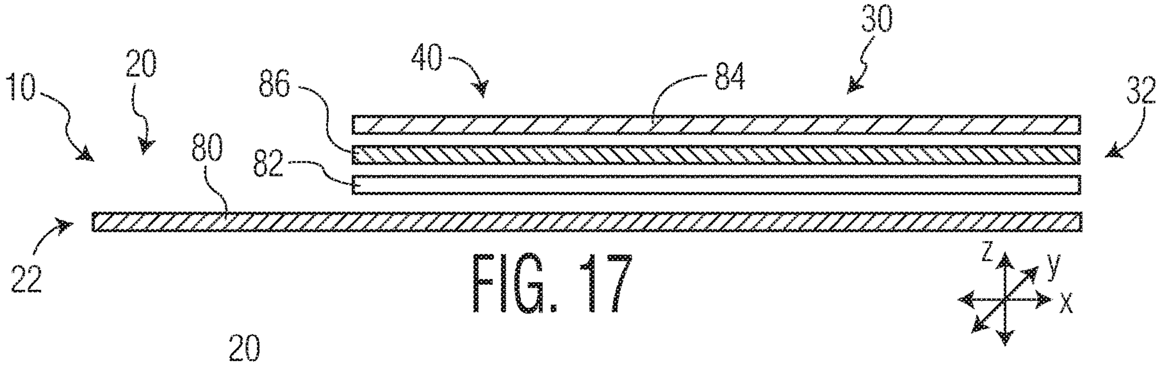

FIG. 7 provides a two-dimensional schematic of a plan view of another embodiment of the pull-on wearable article 10 of FIG. 1 in a longitudinally and transversely stretched and laid-flat configuration with the surface of the pull-on wearable article 10 that faces the wearer when the pull-on wearable article 10 is worn facing the viewer. At least a portion of each of the crotch region 40 and the back region 30 of the pull-on wearable article 10 of FIG. 7 can be formed of at least 3 or 4 layers of material while the front region 20 of the pull-on wearable article 10 of FIG. 7 is formed of a single layer of material. Examples of such constructions can be seen in the exemplary embodiments illustrated in FIGS. 15 and 17. FIG. 15 provides a cross-sectional illustration of an exemplary embodiment of the pull-on wearable article 10 of FIG. 7, taken along the longitudinal direction axis 12, wherein a portion of the front region 20 of the pull-on wearable article 10 is formed of a single layer of material, an article body layer 80, while three layers of material, an article body layer 80, a liquid impermeable barrier layer 82, and a wicking layer 84 form at least a portion of each of the crotch region 40 and the back region 30. FIG. 17 provides a cross-sectional illustration of another exemplary embodiment of the pull-on wearable article 10 of FIG. 7, taken along the longitudinal direction axis 12, wherein at least a portion of the front region 20 of the pull-on wearable article 10 is formed of a single layer of material, an article body layer 80, while four layers of material, an article body layer 80, a liquid impermeable barrier layer 82, an absorbent layer 86, and a wicking layer 84, form at least a portion of each of the crotch region 40 and the back region 30. Each of the liquid impermeable barrier layer 82, absorbent layer 86, and wicking layer 84, when each layer is present, can have a dimension within each of the back region 30 and crotch region 40 that can be equal to or less than the dimension of the article body layer 80 within the each of the back region 30 and crotch region 40 of the pull-on wearable article 10.

Figure 8:
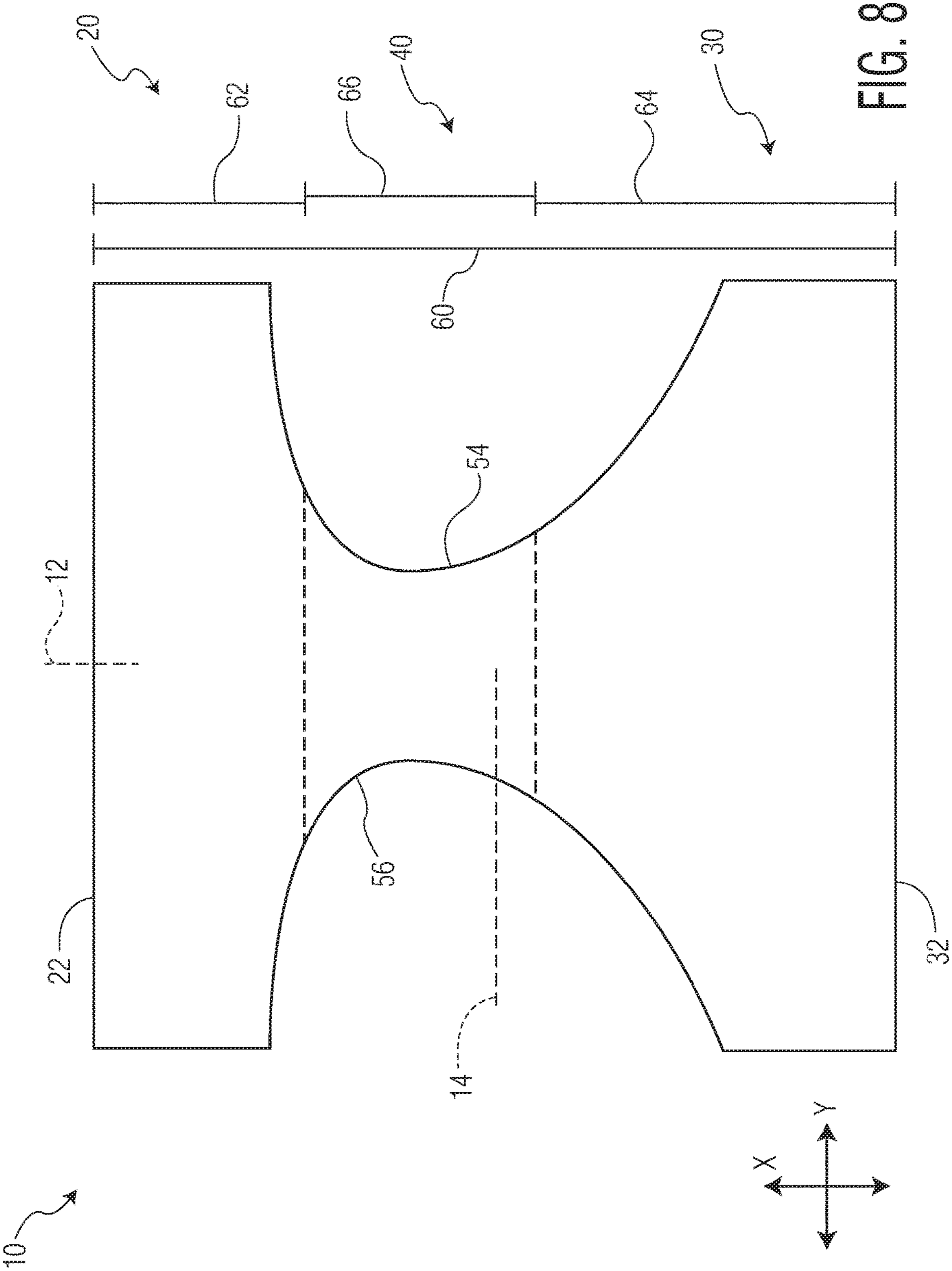
Figure 18:
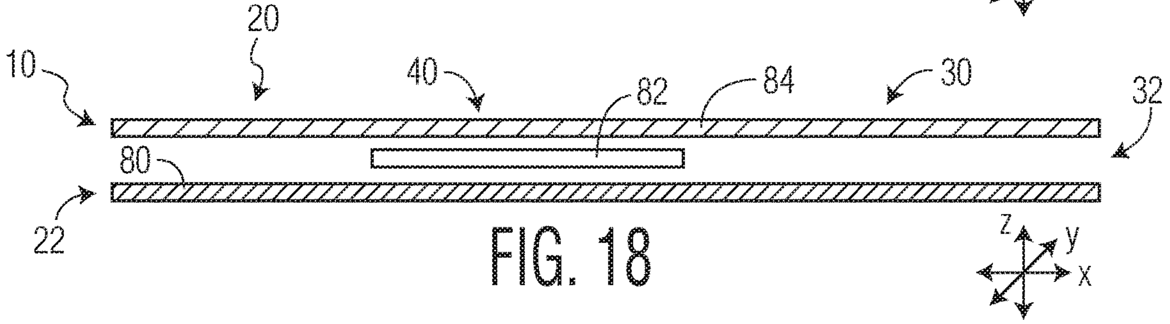
Figure 19:
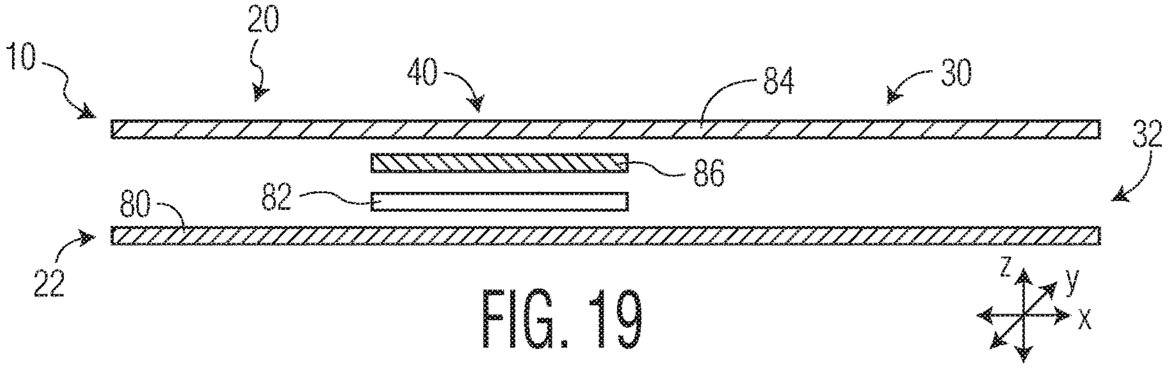
Figure 21:
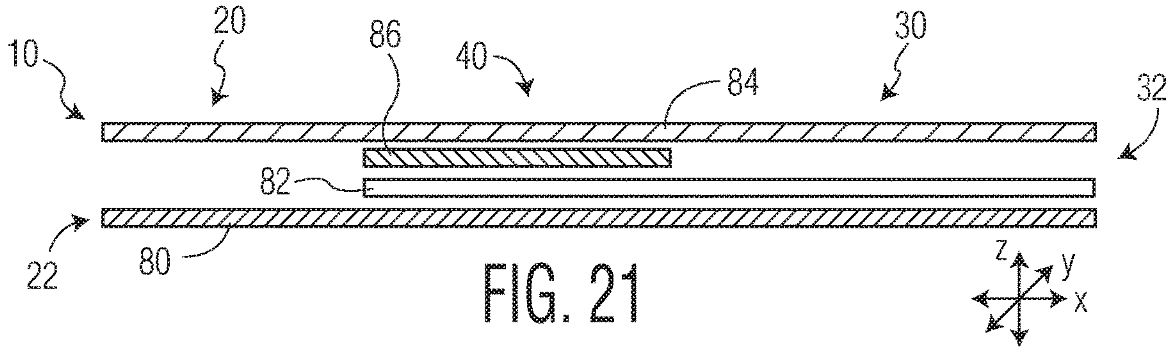
Figure 24:
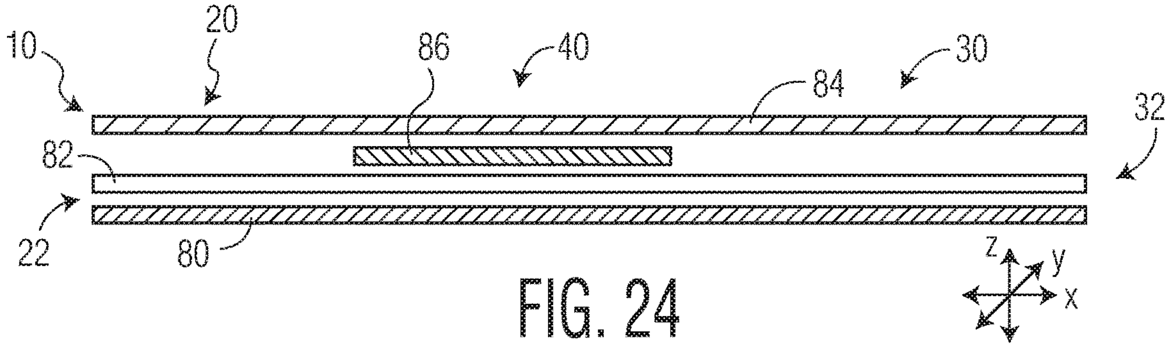

FIG. 8 provides a two-dimensional schematic of a plan view of another embodiment of the pull-on wearable article 10 of FIG. 1 in a longitudinally and transversely stretched and laid-flat configuration with the surface of the pull-on wearable article 10 that faces the wearer when the pull-on wearable article 10 is worn facing the viewer. At least a portion of the crotch region 40 of the pull-on wearable article 10 of FIG. 8 can be formed of at least 3 or 4 layers of material while at least a portion of the front region 20 and at least a portion of the back region 30 of the pull-on wearable article 10 of FIG. 8 can be formed of 2 or 3 layers of material. Examples of such constructions can be seen in the exemplary embodiments illustrated in FIGS. 18, 19, 21, and 24. FIG. 18 provides a cross-sectional illustration of an exemplary embodiment of the pull-on wearable article 10 of FIG. 8, taken along the longitudinal direction axis 12, wherein at least a portion of each of the front region 20 and the back region 30 of the pull-on wearable article 10 is formed of two layers of material, an article body layer 80 and a wicking layer 84, and at least a portion of the crotch region 40 is formed of three layers of material, an article body layer 80, a liquid impermeable barrier layer 82, and a wicking layer 84. FIG. 19 provides a cross-sectional illustration of an exemplary embodiment of the pull-on wearable article 10 of FIG. 8, taken along the longitudinal direction axis 12, wherein at least a portion of each of the front region 20 and the back region 30 of the pull-on wearable article 10 is formed of two layers of material, an article body layer 80 and a wicking layer 84, and at least a portion of the crotch region 40 is formed of four layers of material, an article body layer 80, a liquid impermeable barrier layer 82, an absorbent layer 86, and a wicking layer 84. FIG. 21 provides a cross-sectional illustration of another exemplary embodiment of the pull-on wearable article 10 of FIG. 8, taken along the longitudinal direction axis 12, wherein at least a portion of the front region 20 of the pull-on wearable article 10 is formed of two layers of material, an article body layer 80 and a wicking layer 84, while at least a portion of the crotch region 40 is formed of four layers of material, an article body layer 80, a liquid impermeable barrier layer 82, an absorbent layer 86, and a wicking layer 84, and three layers of material, an article body layer 80, a liquid impermeable barrier layer 82, and a wicking layer 84, form at least a portion of the back region 30 of the pull-on wearable article 10. FIG. 24 provides a cross-sectional illustration of another exemplary embodiment of the pull-on wearable article 10 of FIG. 8, taken along the longitudinal direction axis 12, wherein at least a portion of each of the front region 20 and back region 30 can be formed of three layers of material, an article body layer 80, a liquid impermeable barrier layer 82, and a wicking layer 84, while at least a portion of the crotch region 40 can be formed of four layers of material, an article body layer 80, a liquid impermeable barrier layer 82, a wicking layer 84, and an absorbent layer 86. When the absorbent layer 86 is present, it can have a dimension within the crotch region 40 that can be equal to or less than the dimension of the article body layer 80 within the crotch region 40 of the pull-on wearable article 10. When the liquid impermeable barrier layer 82 is present in only the crotch region 40, it can have a dimension equal to or less than the dimension of the article body layer 80 within the crotch region 40. When the liquid impermeable barrier layer 82 is present in at least a portion of each of the crotch region 40 and the back region 30, it can have a first portion within the crotch region 40 that has a dimension which is the same as or less than the dimension of the article body layer 80 within the crotch region 40 and can have a second portion within the back region 30 that has a dimension which is equal to or less than the dimension of the article body layer 80 within the back region 30. When the liquid impermeable barrier layer 82 is present in at least a portion of each of the front region 20, back region 30, and crotch region 40, it can have a first portion within the front region 20 that has a dimension which is the same as or less than the dimension of the article body layer 80 within the front region 20, a second portion within the back region 30 that has a dimension that is the same as or less than the dimension of the article body layer 80 that is within the back region 30, and a third portion within the crotch region 40 that has a dimension that is the same as or less than the dimension of the article body layer 80 within the crotch region 40 of the pull-on wearable article 10. When the wicking layer 84 is present in at least a portion of each of the front region 20, the crotch region 40, and the back region 30, it can have a first portion within the front region 20 that has a dimension which is the same as or less than the dimension of the article body layer 80 within the front region 20, a second portion within the crotch region 40 that can have a dimension that is the same as or less than the dimension of the article body layer 80 within the crotch region 40, and can have a third portion within the back region 30 that has a dimension which is equal to or less than the dimension of the article body layer 80 within the back region 30.

Figure 9:
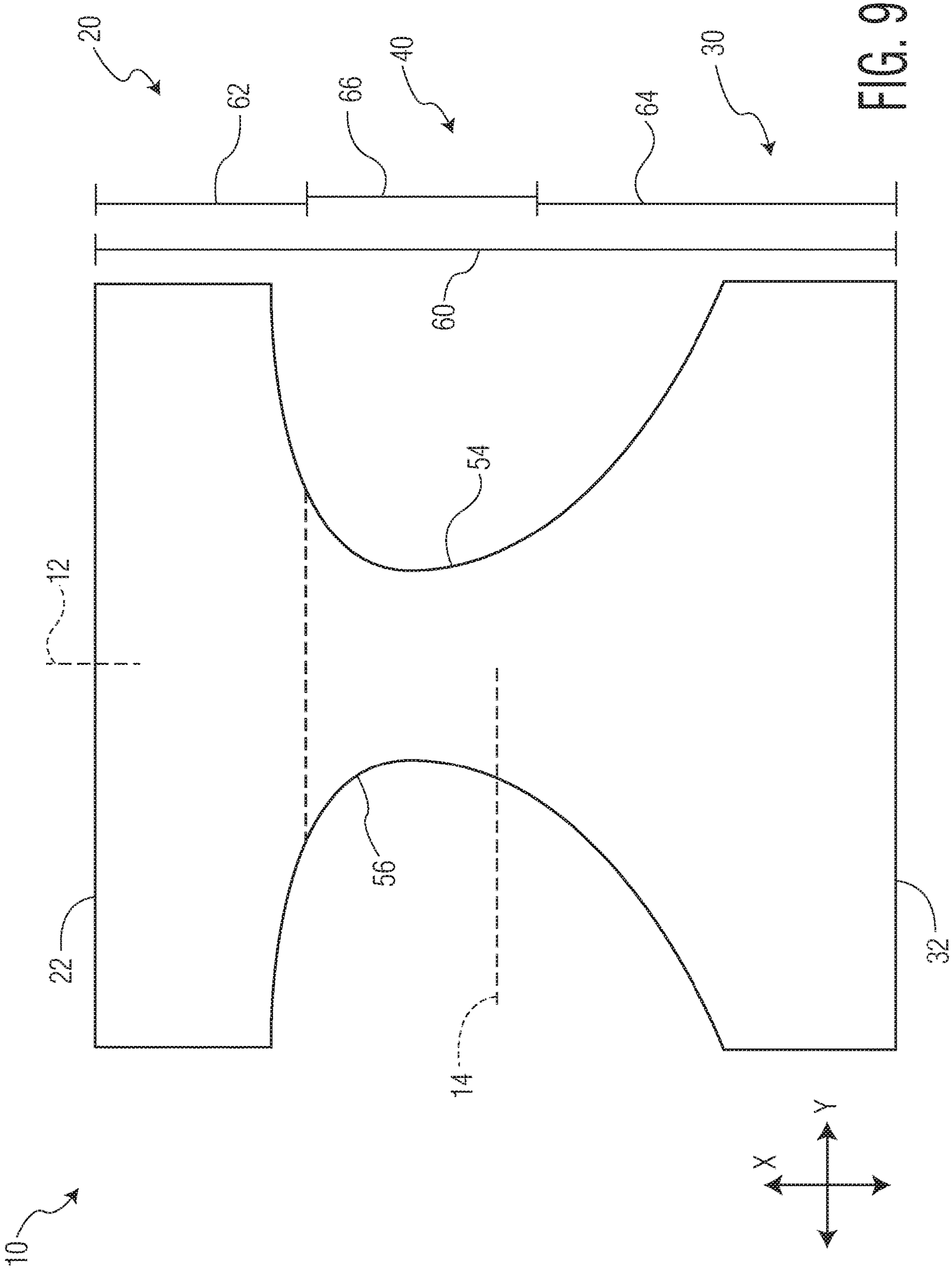
Figure 20:
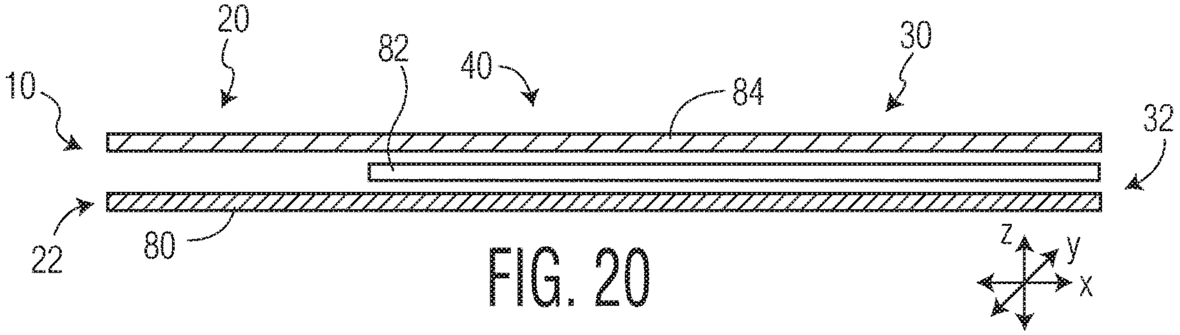
Figure 22:
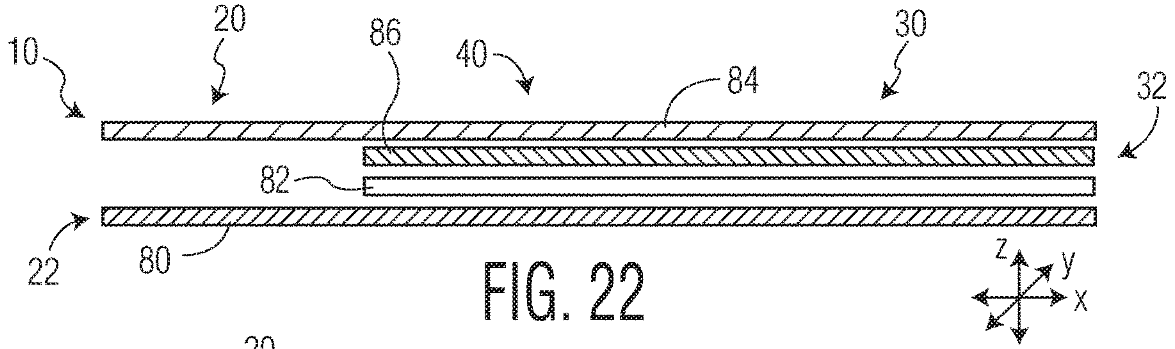
Figure 25:
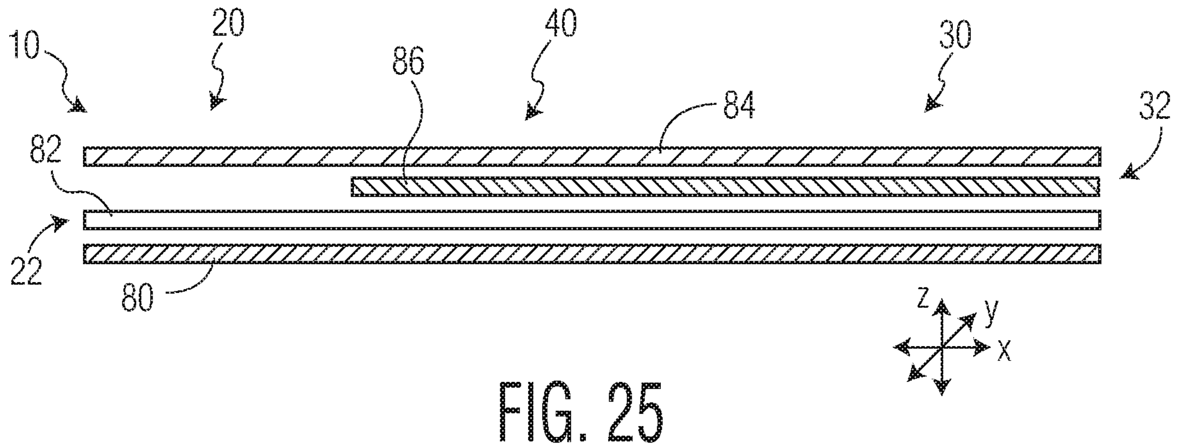

FIG. 9 provides a two-dimensional schematic of a plan view of another embodiment of the pull-on wearable article 10 of FIG. 1 in a longitudinally and transversely stretched and laid-flat configuration with the surface of the pull-on wearable article 10 that faces the wearer when the pull-on wearable article 10 is worn facing the viewer. At least a portion of each of the crotch region 40 and the back region 30 of the pull-on wearable article 10 of FIG. 9 can be formed of at least 3 or 4 layers of material while at least a portion of the front region 20 of the pull-on wearable article 10 of FIG. 9 is formed of 2 or 3 layers of material. Examples of such constructions can be seen in the exemplary embodiments illustrated in FIGS. 20, 22, and 25. FIG. 20 provides a cross-sectional illustration of an exemplary embodiment of the pull-on wearable article 10 of FIG. 9, taken along the longitudinal direction axis 12, wherein at least a portion of each of the crotch region 40 and back region 30 of the pull-on wearable article 10 are formed of 3 layers of material, an article body layer 80, a liquid impermeable barrier layer 82, and a wicking layer 84, while at least a portion of the front region 20 of the pull-on wearable article 10 is formed of 2 layers of material, an article body layer 80 and a wicking layer 84. FIG. 22 provides a cross-sectional illustration of an exemplary embodiment of the pull-on wearable article 10 of FIG. 9, taken along the longitudinal direction axis 12, wherein at least a portion of each of the crotch region 40 and back region 30 of the pull-on wearable article 10 are formed of 4 layers of material, an article body layer 80, a liquid impermeable barrier layer 82, an absorbent layer 86, and a wicking layer 84, while at least a portion of the front region 20 of the pull-on wearable article 10 is formed of 2 layers of material, an article body layer 80 and a wicking layer 84. FIG. 25 provides a cross-sectional illustration of an exemplary embodiment of the pull-on wearable article 10 of FIG. 9, taken along the longitudinal direction axis 12, wherein at least a portion of each of the crotch region 40 and back region 30 of the pull-on wearable article 10 are formed of 4 layers of material, an article body layer 80, a liquid impermeable barrier layer 82, an absorbent layer 86, and a wicking layer 84, while at least a portion of the front region 20 of the pull-on wearable article 10 is formed of 3 layers of material, an article body layer 80, a liquid impermeable barrier layer 82, and a wicking layer 84. Each of the liquid impermeable barrier layer 82, absorbent layer 86, and wicking layer 84, when each layer is present, can have a dimension within each of the back region 30 and crotch region 40 that can be equal to or less than the dimension of the article body layer 80 within the each of the back region 30 and crotch region 40 of the pull-on wearable article 10. Each of the wicking layer 84 and liquid impermeable barrier layer 82, when present in the front region 20, can have a dimension that is the same as or less than the dimension of the article body layer 80 within the front region 20.

An informational cue can be associated with the pull-on wearable article 10 to communicate to the wearer of the pull-on wearable article where to place the crotch region of an absorbent article when placing the absorbent article into the pull-on wearable article. The informational cue triggers a cognitive response in the wearer of the pull-on wearable article and can be an attention attracting graphic, textural feature, or a combination thereof. In various embodiments, the pull-on wearable article 10 can be associated with at least one internally visible informational cue. In various embodiments, the pull-on wearable article 10 can be associated with at least one externally visible informational cue. In various embodiments, the pull-on wearable article 10 can be associated with at least one internally visible informational cue and at least one externally visible informational cue. In various embodiments in which the pull-on wearable article 10 can be associated with at least one internally visible informational cue and at least one externally visible informational cue, at least one of the internally visible informational cue and at least one of the externally visible informational cue are aligned with each other.

In various embodiments, the pull-on wearable article 10 can be associated with at least one internally visible informational cue. In various embodiments, the internally visible informational cue can be located within the crotch region 40 of the pull-on wearable article 10. In various embodiments, the pull-on wearable article 10 can have an internally visible informational cue wherein a first portion of the internally visible informational cue is located within a portion of the crotch region 40 and a second portion of the internally visible informational cue is located within a portion of the front region 20 of the pull-on wearable article 10. In various embodiments, the pull-on wearable article 10 can have an internally visible informational cue wherein a first portion of the internally visible informational cue is located within a portion of the crotch region 40, a second portion of the internally visible informational cue is located within a portion of the front region 20, and a third portion of the internally visible informational cue is located within a portion of the back region 30 of the pull-on wearable article 10. In various embodiments, the pull-on wearable article 10 can have multiple internally visible informational cues wherein a first internally visible informational cue is located within the crotch region 40 and a second internally visible informational cue is located within the front region 20 wherein the first internally visible informational cue is separate from and spaced apart from the second internally visible informational cue. In various embodiments, the pull-on wearable article 10 can have multiple internally visible informational cues wherein a first internally visible informational cue is located in the crotch region 40, a second internally visible informational cue is located within the front region 20, and a third internally visible informational cue is located within the back region 30 wherein the first internally visible informational cue, the second internally visible informational cue, and the third internally visible informational cue are separate from and spaced apart from each other.

In various embodiments in which at least a portion of an internally visible informational cue is located within the crotch region 40 of the pull-on wearable article 10, at least a portion of the internally visible informational cue can be in an overlapping configuration with at least a portion of the narrowest transverse direction region 70 of the pull-on wearable article 10. Regarding the female genital anatomy, the vulvar region is where each of the vaginal opening and the urethral opening are located and each of the vaginal opening and the urethral opening are located anterior to the mid-coronal plane of the body. When the pull-on wearable article 10 is worn by the wearer, as the narrowest transverse direction region 70 of the pull-on wearable article 10 is located anterior to the transverse direction axis 14 of the pull-on wearable article 10, the narrowest transverse direction region 70 of the pull-on wearable article 10 will align with vulvar region of the wearer of the pull-on wearable article 10. The purpose of the internally visible informational cue positioned within the crotch region 40 of the pull-on wearable article 10 is to communicate to the wearer of the pull-on wearable article 10 where to place the crotch region of an absorbent article when placing the absorbent article into the pull-on wearable article 10 for capturing body exudates from the wearer of the pull-on wearable article 10. Positioning at least one internally visible informational cue within the crotch region 40 of the pull-on wearable article 10 wherein at least a portion of the internally visible informational cue is in an overlapping configuration with the narrowest transverse direction region 70 communicates to the wearer of the pull-on wearable article 10 that the crotch region of the absorbent article will be in the proper placement to capture their body exudates as the crotch region of the absorbent article will be aligned with the vulvar region of the wearer of the pull-on wearable article 10. It is to be understood that in various embodiments in which at least a portion of an internally visible informational cue is in an overlapping configuration with the narrowest transverse direction region 70, the overlapping portion of the internally visible informational cue can have a size dimension equal to, greater than, or smaller than the size dimension of the narrowest transverse direction region 70.

In various embodiments in which the pull-on wearable article 10 has an internally visible informational cue located within the front region 20 of the pull-on wearable article 10, such an internally visible informational cue can communicate to the wearer of the pull-on wearable article 10 where to position an anterior region of an absorbent article. In various embodiments in which the pull-on wearable article 10 has an internally visible informational cue located within the front region 20 of the pull-on wearable article 10, such an internally visible informational cue can communicate to the wearer of the pull-on wearable article 10 where to position an anterior edge of an absorbent article. In various embodiments in which the pull-on wearable article 10 has an internally visible informational cue located within the back region 30 of the pull-on wearable article 10, such an internally visible informational cue can communicate to the wearer of the pull-on wearable article 10 where to position a posterior region of an absorbent article. In various embodiments in which the pull-on wearable article 10 has an internally visible informational cue located within the back region 30 of the pull-on wearable article 10, such an internally visible informational cue can communicate to the wearer of the pull-on wearable article 10 where to position a posterior edge of an absorbent article.

In various embodiments in which the internally visible informational cue is a graphic, the graphic can be provided in the form of a shape and/or image. For example, the graphic can be formed of one or more dots, one or more lines, one or more arrows, one or more regular or irregular shapes (such as circles, ovals, triangles, rectangles, squares, ellipses, diamonds, etc), or combinations thereof. In various embodiments, the graphic can have a color wherein the color can either be uniform or variable from either one hue to another or variable from light to dark. In various embodiments, the graphic can include an image of an object readily recognizable by a human viewer.

In various embodiments in which the internally visible informational cue is a textural feature, the textural feature can alter the feel of a portion of a layer of the pull-on wearable article 10. For example, a textural feature may alter the smoothness, may alter the roughness, may vary the reflectivity, may enhance a color, may replace a portion of the material forming the layer with a different type of material, may vary the functionality of a portion of the layer, or combinations thereof, of a portion of layer of the pull-on wearable article 10.

In various embodiments, the pull-on wearable article 10 can have at least 1, 2, 3, or 4 internally visible informational cues. In various embodiments in which the pull-on wearable article 10 has more than 1 internally visible informational cue, each of the internally visible informational cues can be the same. In various embodiments in which the pull-on wearable article 10 has more than 1 internally visible informational cue, each of the internally visible informational cues can be different. In various embodiments in which the pull-on wearable article 10 has at least 3 internally visible informational cues, each of the internally visible informational cues can be the same. In various embodiments in which the pull-on wearable article 10 has at least 3 internally visible informational cues, each of the internally visible informational cues can be different. In various embodiments in which the pull-on wearable article 10 has at least 3 internally visible informational cues, at least two the internally visible informational cues can be the same and at least two of the internally visible informational cues can be different. A difference between two internally visible informational cues can be the result of for example, but not limited to, a different color, different graphic, different shape, different size, different textural feature, etc. between the two different internally visible informational cues.

FIG. 3 and FIGS. 27-33 provide two-dimensional schematic illustrations of plan views of exemplary embodiments of the pull-on wearable article 10 of FIG. 1 in a longitudinally and transversely stretched and laid-flat configuration with the surface of the pull-on wearable article 10 that faces the wearer when the pull-on wearable article 10 is worn facing the viewer and wherein the pull-on wearable article 10 has at least one internally visible informational cue in the form of a graphic. While the at least one internally visible informational cue illustrated in each of FIGS. 3 and 27-33 is illustrated in the form of a graphic, it is to be understood that the at least one internally visible informational cue could be a textural feature or a combination of a graphic and textural feature.

Figure 27:
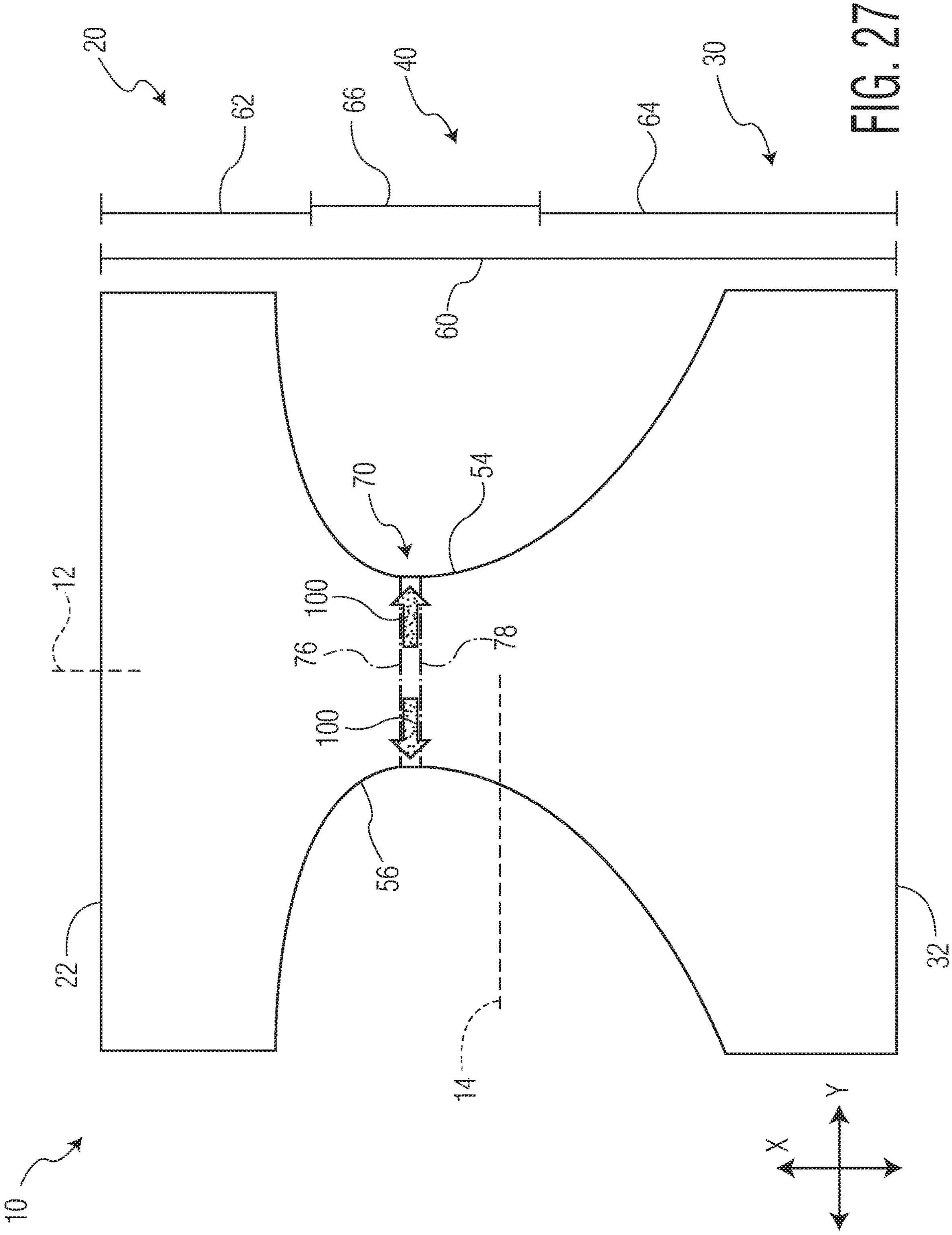
FIGS. 27-33 are two-dimensional illustrations of plan views of alternate embodiments of the pull-on wearable article in a longitudinally and transversely stretched and laid-flat configuration with the surface of the pull-on wearable article that faces the wearer when the pull-on wearable article is worn facing the viewer and wherein the pull-on wearable article has at least one internally visible informational cue in the form of a graphic.
Figure 28:
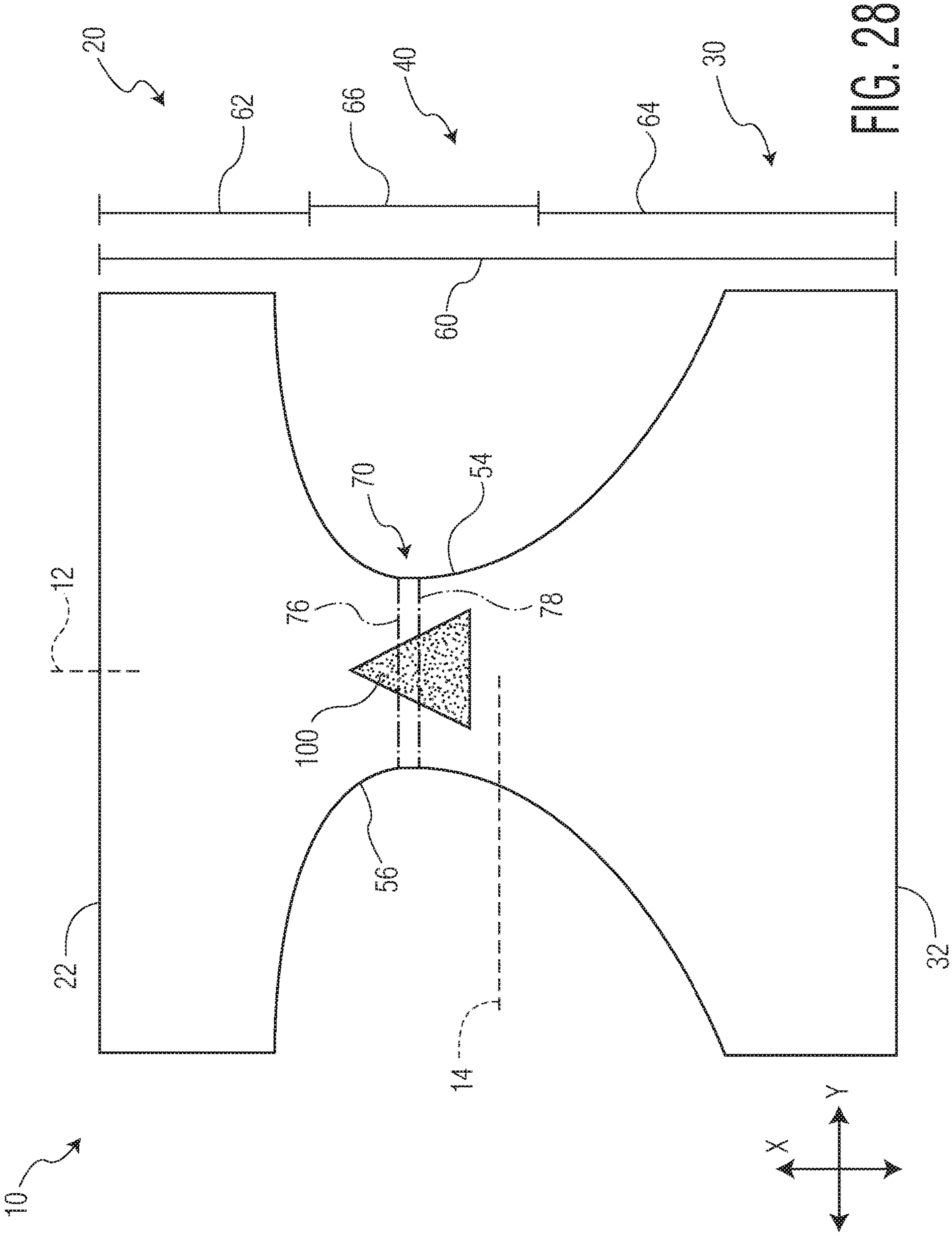

FIG. 3 provides an exemplary illustration of a pull-on wearable article 10 which has an internally visible informational cue 100. The internally visible informational cue 100 can be a graphic such as a line. In the exemplary embodiment illustrated in FIG. 3, the internally visible informational cue 100 is located entirely within the crotch region 40 of the pull-on wearable article 10 and at least a portion of the internally visible informational cue 100 is in an overlapping configuration with the narrowest transverse direction region 70 of the pull-on wearable article 10. In the exemplary embodiment illustrated in FIG. 3, the overlapping portion of the internally visible informational cue 100 is illustrated as having a size dimension which is the same as the size dimension of the narrowest transverse direction region 70 of the pull-on wearable article 10. FIG. 27 provides an exemplary illustration of a pull-on wearable article 10 which has an internally visible informational cue 100. The internally visible informational cue 100 can be a graphic such as a pair of arrows. In the exemplary embodiment illustrated in FIG. 27, the internally visible informational cue 100 is located entirely within the crotch region 40 of the pull-on wearable article 10 and at least a portion of the internally visible informational cue 100 is in an overlapping configuration with the narrowest transverse direction region 70 of the pull-on wearable article 10. In the exemplary embodiment illustrated in FIG. 27, the overlapping portion of the internally visible informational cue 100 is illustrated as having a size dimension which is smaller than the size dimension of the narrowest transverse direction region 70 of the pull-on wearable article 10. FIG. 28 provides an exemplary illustration of a pull-on wearable article 10 which has an internally visible informational cue 100. The internally visible informational cue 100 can be a graphic such as a triangle. In the exemplary embodiment illustrated in FIG. 28, the internally visible informational cue 100 is located entirely within the crotch region 40 of the pull-on wearable article 10 and at least a portion of the internally visible informational cue 100 is in an overlapping configuration with the narrowest transverse direction region 70 of the pull-on wearable article 10. In the exemplary embodiment illustrated in FIG. 28, the overlapping portion of the internally visible informational cue 100 is illustrated as having a size dimension which is smaller than the size dimension of the narrowest transverse direction region 70 of the pull-on wearable article 10.

Figure 29:
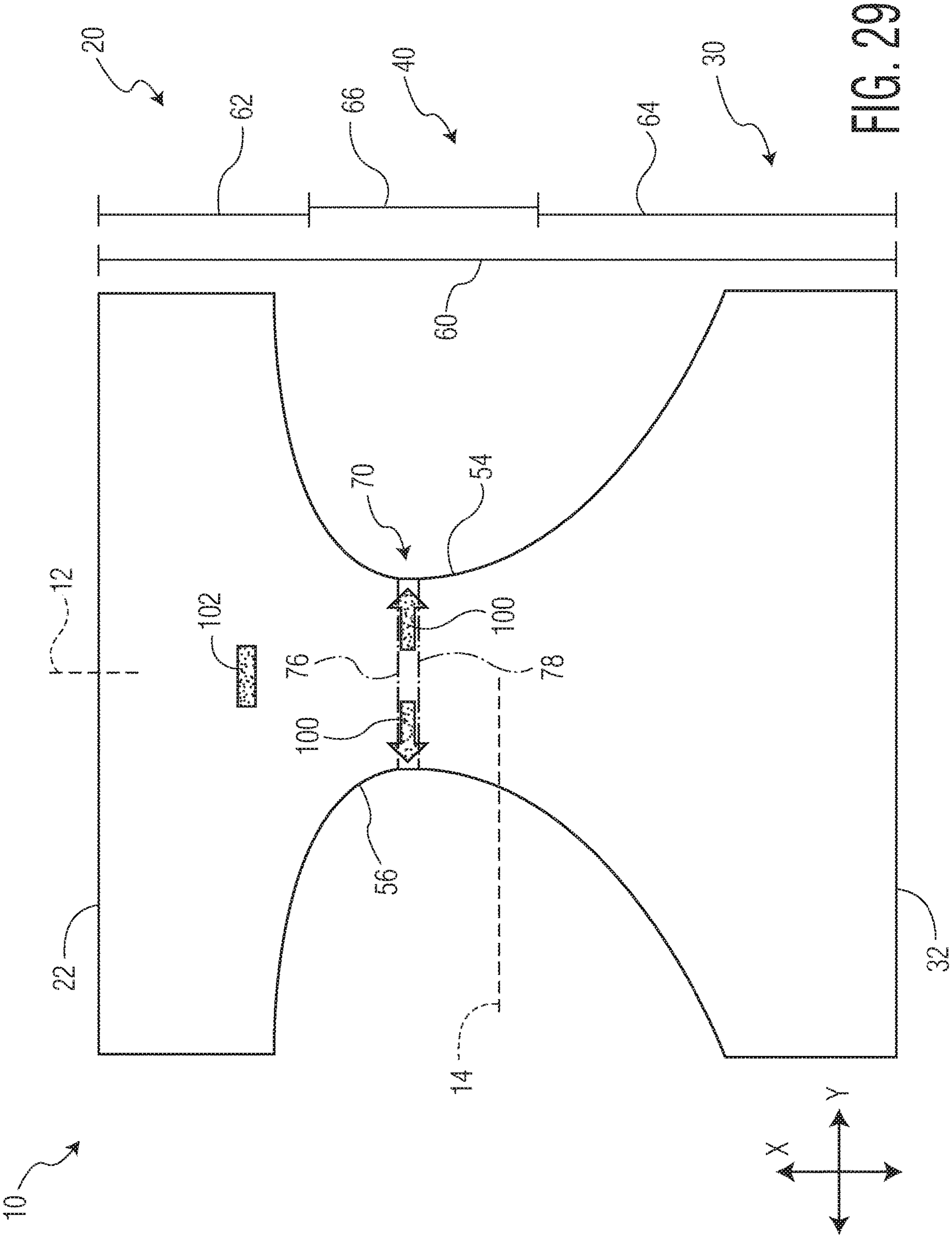

FIG. 29 provides an exemplary illustration of a pull-on wearable article 10 which has two internally visible informational cues, a first internally visible informational cue 100 and a second internally visible informational cue 102. The first internally visible informational cue 100 can be a graphic such as a pair of arrows. In the exemplary embodiment illustrated in FIG. 29, the first internally visible informational cue 100 is located entirely within the crotch region 40 of the pull-on wearable article 10 and at least a portion of the first internally visible informational cue 100 is in an overlapping configuration with the narrowest transverse direction region 70 of the pull-on wearable article 10. In the exemplary embodiment illustrated in FIG. 29, the overlapping portion of the first internally visible informational cue 100 is illustrated as having a size dimension which is smaller than the size dimension of the narrowest transverse direction region 70 of the pull-on wearable article 10. The second internally visible informational cue 102 is located entirely within the front region 20 of the pull-on wearable article 10 and is separate and spaced apart from the first internally visible informational cue 100. The second internally visible informational cue 102 is a graphic and generally in the shape of a rectangle. While the first internally visible informational cue 100 can communicate to the wearer of the pull-on wearable article 10 the location to place the crotch region of an absorbent article, the second internally visible informational cue 102 can be placed in such a location of the front region 20 so that it can communicate to the wearer of the pull-on wearable article 10 where to place the anterior edge of the absorbent article when placing the absorbent article into the pull-on wearable article 10.

Figure 30:
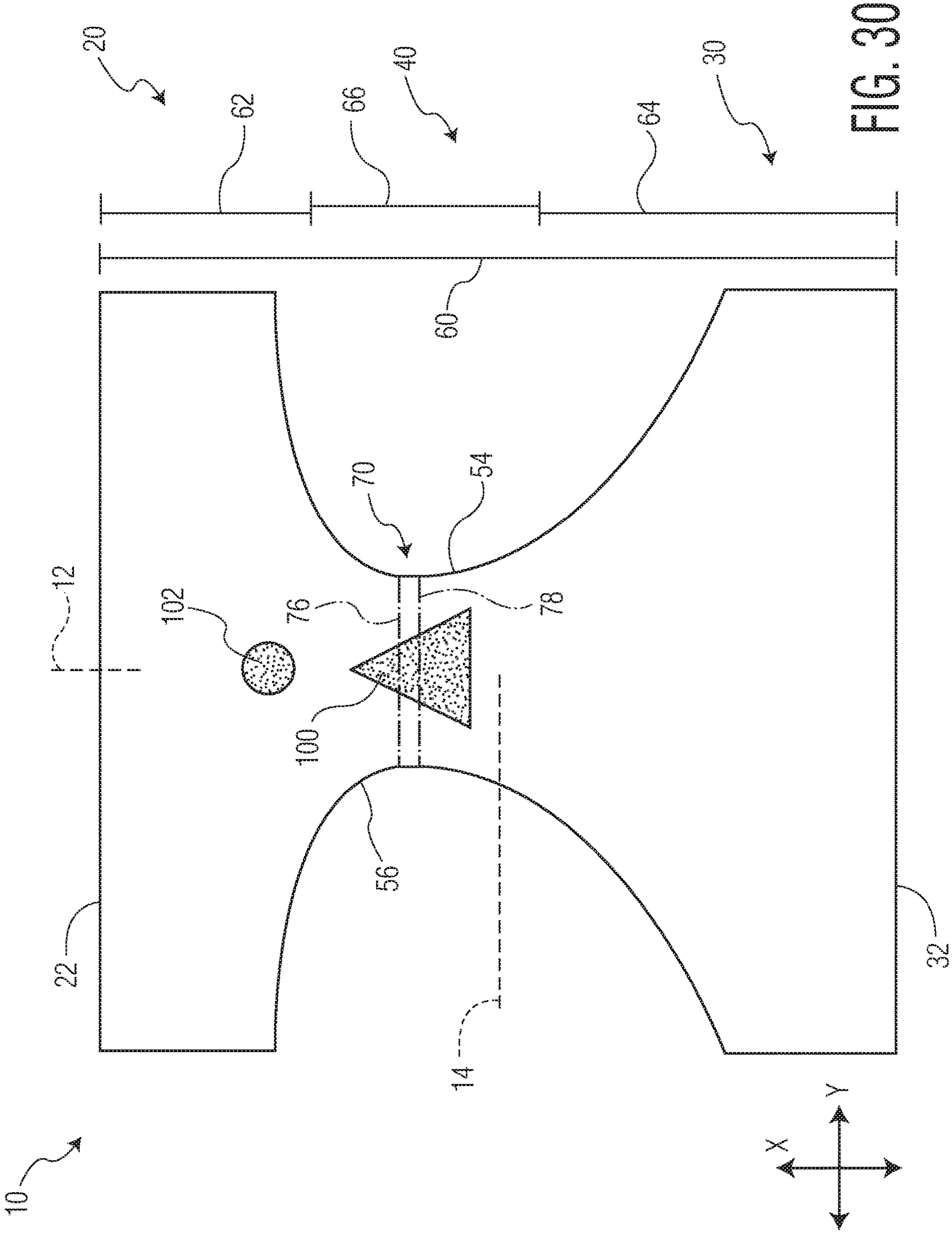

FIG. 30 provides an exemplary illustration of a pull-on wearable article 10 which has two internally visible informational cues, a first internally visible informational cue 100 and a second internally visible informational cue 102. The first internally visible informational cue 100 can be a graphic such as a triangle. In the exemplary embodiment illustrated in FIG. 30, the first internally visible informational cue 100 is located entirely within the crotch region 40 of the pull-on wearable article 10 and at least a portion of the first internally visible informational cue 100 is in an overlapping configuration with the narrowest transverse direction region 70 of the pull-on wearable article 10. In the exemplary embodiment illustrated in FIG. 30, the overlapping portion of the first internally visible informational cue 100 is illustrated as having a size dimension which is smaller than the size dimension of the narrowest transverse direction region 70 of the pull-on wearable article 10. The second internally visible informational cue 102 is located entirely within the front region 20 of the pull-on wearable article 10 and is separate and spaced apart from the first internally visible informational cue 100. The second internally visible informational cue 102 is a graphic and in the shape of a circle. While the first internally visible informational cue 100 can communicate to the wearer of the pull-on wearable article 10 the location to place the crotch region of an absorbent article, the second internally visible informational cue 102 can be placed in such a location of the front region 20 so that it can communicate to the wearer of the pull-on wearable article 10 the location to place the anterior region of an absorbent article when placing the absorbent article into the pull-on wearable article 10.

Figure 31:
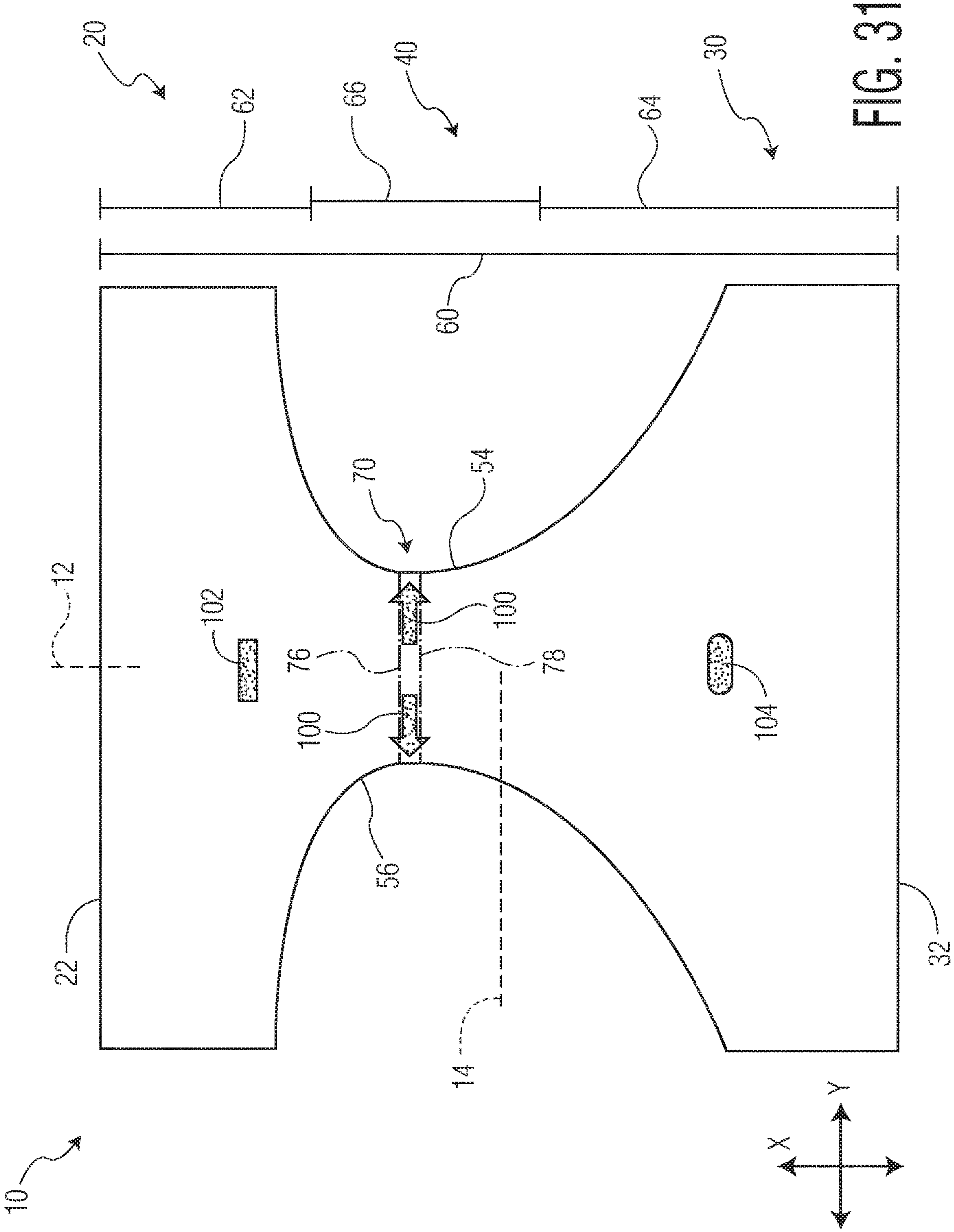

FIG. 31 provides an exemplary illustration of a pull-on wearable article 10 which has three internally visible informational cues, a first internally visible informational cue 100, a second internally visible informational cue 102, and a third internally visible informational cue 104. The first internally visible informational cue 100 can be a graphic such as a pair of arrows. In the exemplary embodiment illustrated in FIG. 31, the first internally visible informational cue 100 is located entirely within the crotch region 40 of the pull-on wearable article 10 and at least a portion of the first internally visible informational cue 100 is in an overlapping configuration with the narrowest transverse direction region 70 of the pull-on wearable article 10. In the exemplary embodiment illustrated in FIG. 31, the overlapping portion of the first internally visible informational cue 100 is illustrated as having a size dimension which is smaller than the size dimension of the narrowest transverse direction region 70 of the pull-on wearable article 10. The second internally visible informational cue 102 is located entirely within the front region 20 of the pull-on wearable article 10 and is separate and spaced apart from the first internally visible informational cue 100. The second internally visible informational cue 102 is a graphic and generally in the shape of a rectangle. While the first internally visible informational cue 100 can communicate to the wearer of the pull-on wearable article 10 the location to place the crotch region of an absorbent article, the second internally visible informational cue 102 can be placed in such a location of the front region 20 so that it can communicate to the wearer of the pull-on wearable article where to place the anterior edge of the absorbent article when placing the absorbent article into the pull-on wearable article 10. The third internally visible informational cue 104 is located entirely within the back region 30 of the pull-on wearable article 10 and is separate and spaced apart from each of the first internally visible informational cue 100 and the second internally visible informational cue 102. The third internally visible informational cue 104 is a graphic and generally in the shape of an oval. While the first internally visible informational cue 100 can communicate to the wearer of the pull-on wearable article 10 the location to place the crotch region of an absorbent article and the second internally visible informational cue 102 can be placed in such a location of the front region 20 so that it can communicate to the wearer of the pull-on wearable article 10 where to place the anterior edge of the absorbent article, the third internally visible informational cue 104 can be placed in such a location of the back region 30 so that it can communicate to the wearer of the pull-on wearable article 10 where to place the posterior edge of the absorbent article when placing the absorbent article into the pull-on wearable article 10.

Figure 32:
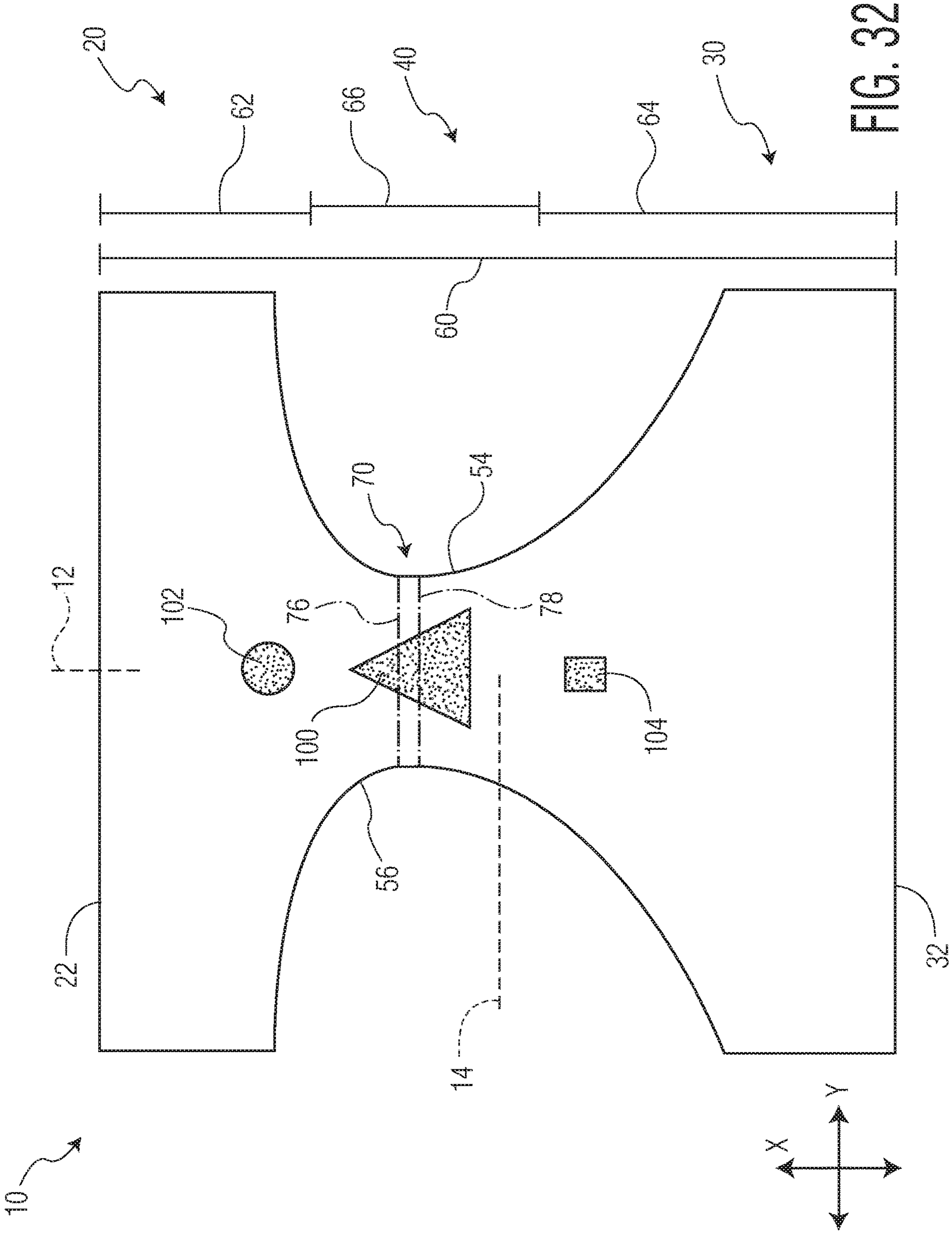

FIG. 32 provides an exemplary illustration of a pull-on wearable article 10 which has three internally visible informational cues, a first internally visible informational cue 100, a second internally visible informational cue 102, and a third internally visible informational cue 104. The first internally visible informational cue 100 can be a graphic such as a triangle. In the exemplary embodiment illustrated in FIG. 32, the first internally visible informational cue 100 is located entirely within the crotch region 40 of the pull-on wearable article 10 and at least a portion of the first internally visible informational cue 100 is in an overlapping configuration with the narrowest transverse direction region 70 of the pull-on wearable article 10. In the exemplary embodiment illustrated in FIG. 32, the overlapping portion of the first internally visible informational cue 100 is illustrated as having a size dimension which is smaller than the size dimension of the narrowest transverse direction region 70 of the pull-on wearable article 10. The second internally visible informational cue 102 is located entirely within the front region 20 of the pull-on wearable article 10 and is separate and spaced apart from the first internally visible informational cue 100. The second internally visible informational cue 102 is a graphic and in the shape of a circle. While the first internally visible informational cue 100 can communicate to the wearer of the pull-on wearable article 10 the location to place the crotch region of an absorbent article, the second internally visible informational cue 102 can be placed in such a location of the front region 20 so that it can communicate to the wearer of the pull-on wearable article 10 the location to place the anterior region of an absorbent article when placing the absorbent article into the pull-on wearable article 10. The third internally visible informational cue 104 is located entirely within the back region 30 of the pull-on wearable article 10 and is separate and spaced apart from each of the first internally visible informational cue 100 and the second internally visible informational cue 102. The third internally visible informational cue 104 is a graphic and generally in the shape of a square. While the first internally visible informational cue 100 can communicate to the wearer of the pull-on wearable article 10 the location to place the crotch region of an absorbent article and the second internally visible informational cue 102 can be placed in such a location of the front region 20 so that it can communicate to the wearer of the pull-on wearable article 10 where to place the anterior region of the absorbent article, the third internally visible informational cue 104 can be placed in such a location of the back region 30 so that it can communicate to the wearer of the pull-on wearable article 10 where to place the posterior region of the absorbent article when placing the absorbent article into the pull-on wearable article 10.

Figure 33:
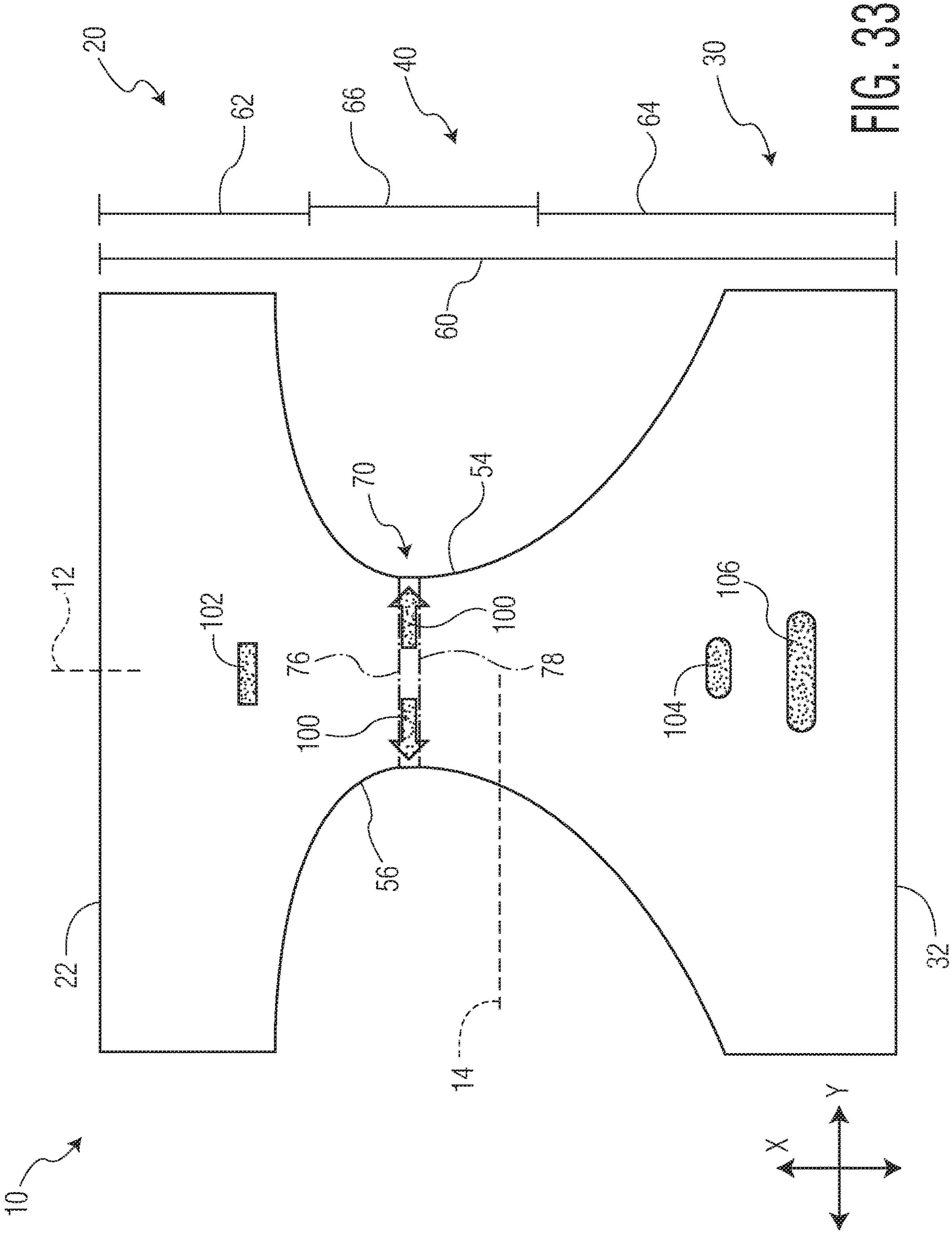

FIG. 33 provides an exemplary illustration of a pull-on wearable article 10 which has four internally visible informational cues, a first internally visible informational cue 100, a second internally visible informational cue 102, a third internally visible informational cue 104, and a fourth internally visible informational cue 106. The first internally visible informational cue 100 can be a graphic such as a pair of arrows. In the exemplary embodiment illustrated in FIG. 33, the first internally visible informational cue 100 is located entirely within the crotch region 40 of the pull-on wearable article 10 and at least a portion of the first internally visible informational cue 100 is in an overlapping configuration with the narrowest transverse direction region 70 of the pull-on wearable article 10. In the exemplary embodiment illustrated in FIG. 33, the overlapping portion of the first internally visible informational cue 100 is illustrated as having a size dimension which is smaller than the size dimension of the narrowest transverse direction region 70 of the pull-on wearable article 10. The second internally visible informational cue 102 is located entirely within the front region 20 of the pull-on wearable article 10 and is separate and spaced apart from the first internally visible informational cue 100. The second internally visible informational cue 102 is a graphic and generally in the shape of a rectangle. While the first internally visible informational cue 100 can communicate to the wearer of the pull-on wearable article 10 the location to place the crotch region of an absorbent article, the second internally visible informational cue 102 can be placed in such a location of the front region 20 so that it can communicate to the wearer of the pull-on wearable article where to place the anterior edge of the absorbent article when placing the absorbent article into the pull-on wearable article 10. The third internally visible informational cue 104 is located entirely within the back region 30 of the pull-on wearable article 10 and is separate and spaced apart from each of the first internally visible informational cue 100 and the second internally visible informational cue 102. The third internally visible informational cue 104 is a graphic and generally in the shape of an oval. While the first internally visible informational cue 100 can communicate to the wearer of the pull-on wearable article 10 the location to place the crotch region of an absorbent article and the second internally visible informational cue 102 can be placed in such a location of the front region 20 so that it can communicate to the wearer of the pull-on wearable article 10 where to place the anterior edge of the absorbent article, the third internally visible informational cue 104 can be placed in such a location of the back region 30 so that it can communicate to the wearer of the pull-on wearable article 10 where to place the posterior edge of the absorbent article when placing the absorbent article into the pull-on wearable article 10. Similar to the third internally visible informational cue 104, the fourth internally visible informational cue 106 is also located entirely within the back region 30 of the pull-on wearable article 10 and is separate and spaced apart from each of the first internally visible informational cue 100, the second internally visible informational cue 102, and the third internally visible informational cue 104. The fourth internally visible informational cue 106 is a graphic and generally in the shape of an oval. Absorbent articles can have variable lengths, such as, for example, an absorbent article intended for overnight usage or for accommodating a heavy menstrual flow and may have a longer total longitudinal direction length between the anterior edge and the posterior edge than the total longitudinal direction length between the anterior edge and the posterior edge of an absorbent article intended for regular or moderate menstrual flow. For example, an absorbent article intended for a heavy menstrual flow or overnight usage of the absorbent article, may have an anterior region and a crotch region which may have a similar longitudinal direction length when compared with an absorbent article for moderate or regular menstrual flow, however, the posterior region of the absorbent article intended for a heavy menstrual flow or overnight usage may be extended in longitudinal length greater than that of the posterior region of a regular or moderate absorbent article in order to accommodate the intended usage needs. While the third internally visible informational cue 104 can be placed in such a location of the back region 30 so that it can communicate to the wearer of the pull-on wearable article 10 where to place the posterior edge of an absorbent article when placing the absorbent article into the pull-on wearable article 10, the fourth internally visible informational cue 106 can be placed in such a location of the back region 30 so that it can communicate to the wearer of the pull-on wearable article 10 where to place the posterior edge of a longer absorbent article such as, for example, an absorbent article that is intended for heavier usage or an overnight usage.

In various embodiments, the pull-on wearable article 10 can be associated with at least one externally visible informational cue. In various embodiments, the externally visible informational cue can be located within the crotch region 40 of the pull-on wearable article 10. In various embodiments in which at least a portion of an externally visible informational cue is located within the crotch region 40 of the pull-on wearable article 10, at least a portion of the externally visible informational cue can be in an overlapping configuration with at least a portion of the narrowest transverse direction region 70 of the pull-on wearable article 10. The purpose of the externally visible informational cue positioned within the crotch region 40 of the pull-on wearable article 10 is to communicate to the wearer of the pull-on wearable article 10 where to place the crotch region of an absorbent article when placing the absorbent article into the pull-on wearable article 10. In various embodiments, an absorbent article can have a pair of wings extending transversely outward from the absorbent article. The wings can be located within the crotch region of the absorbent article and can, when present, facilitate attachment of the absorbent article to the pull-on wearable article 10. An externally visible informational cue can communicate to the wearer of the pull-on wearable article 10 where to place the crotch region of the absorbent article on the body-facing surface of the pull-on wearable article 10 and, when present, where to place the wings on the non-body facing surface of the pull-on wearable article 10 as the wings of the absorbent article will wrap around the material forming the crotch region 40 of the pull-on wearable article 10 and can be secured to the non-body facing surface of the pull-on wearable article 10. In various embodiments in which the externally visible informational cue is a graphic, the graphic can be provided in the form of a shape and/or image. For example, the graphic can be formed of one or more dots, one or more lines, one or more arrows, one or more regular or irregular shapes (such as circles, semi-circles, ovals, triangles, rectangles, squares, ellipses, diamonds, etc), or combinations thereof. In various embodiments, the graphic can have a color wherein the color can either be uniform or variable from either one hue to another or variable from light to dark. In various embodiments, the graphic can include an image of an object readily recognizable by a human viewer. In various embodiments, the graphic can be presented in the exemplary image of an absorbent article wing. In embodiments in which the graphic is presented in an exemplary image of an absorbent article wing, it need not be identical to the wing shape, when present, of an absorbent article being placed into the pull-on wearable article 10 by the wearer. In various embodiments in which the externally visible informational cue is a textural feature, the textural feature can alter the feel of a portion of the layer, such as the article body layer 80, of the pull-on wearable article 10. For example, a textural feature may alter the smoothness, may alter the roughness, may vary the reflectivity, may enhance a color, may replace a portion of the material forming the layer with a different type of layer, may vary the functionality of a portion of the layer, or combinations thereof, of a portion of the layer, such as the article body layer 80, of the pull-on wearable article 10.

Figure 34:
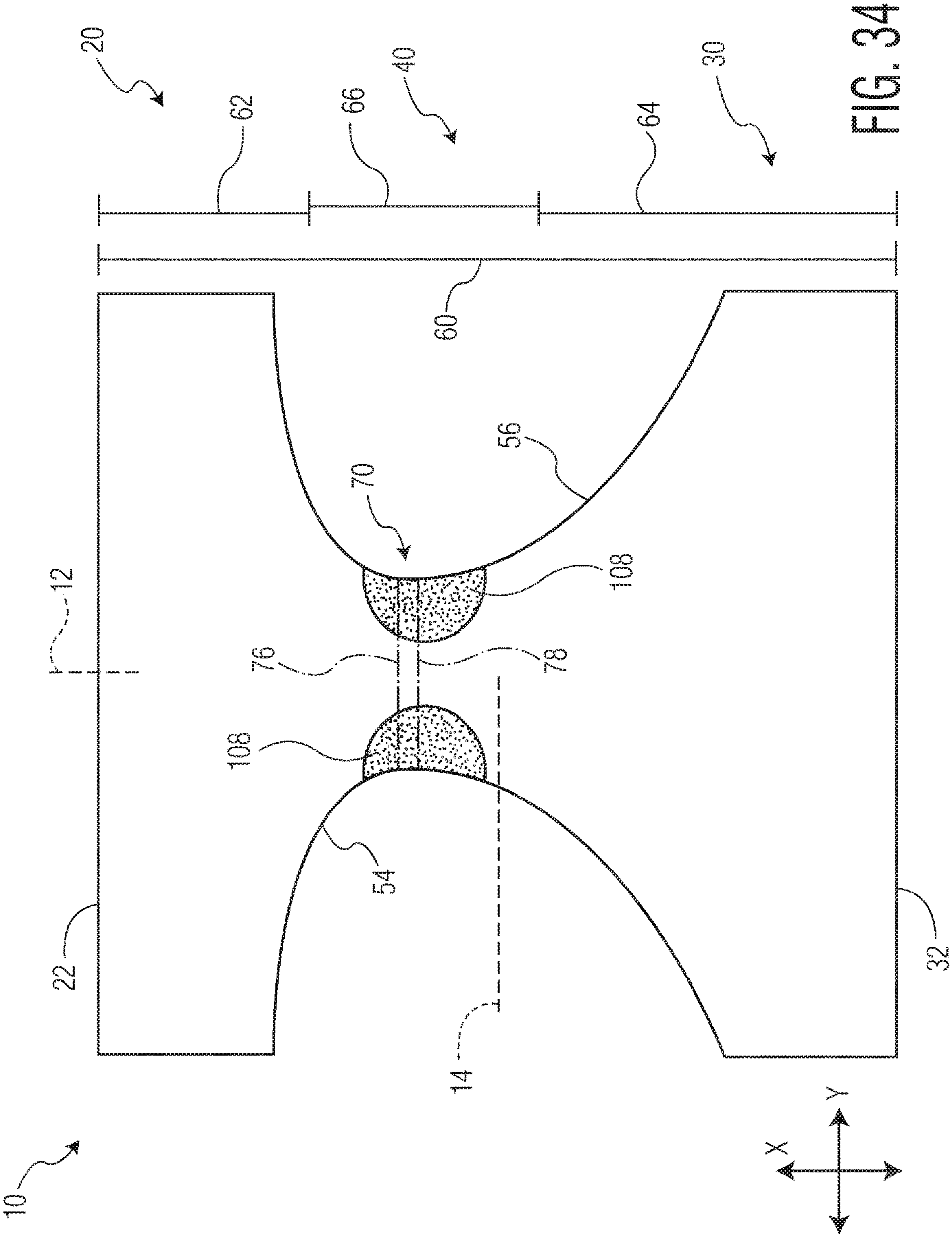
FIG. 34 is a two-dimensional illustration of a plan view of an alternate embodiment of the pull-on wearable article in a longitudinally and transversely stretched and laid-flat configuration with the surface of the pull-on wearable article that faces away from the wearer when the pull-on wearable article is worn facing the viewer and wherein the pull-on wearable article has at least one externally visible informational cue in the form of a graphic.

FIG. 34 provides a two-dimensional schematic illustration of a plan view of an exemplary embodiment of the pull-on wearable article 10 of FIG. 1 in a longitudinally and transversely stretched and laid-flat configuration with the surface of the pull-on wearable article 10 that faces away from the wearer when the pull-on wearable article 10 is worn facing the viewer and wherein the pull-on wearable article 10 has at least one externally visible informational cue 108 in the form of a graphic. While the at least one externally visible informational cue of FIG. 34 is illustrated in the form of a graphic, it is to be understood that the at least one externally visible information cue could be a textural feature or a combination of a graphic and textural feature. The externally visible informational cue 108 can be a graphic such as a pair of semi-circles to illustrate absorbent article wings. In the exemplary embodiment illustrated in FIG. 34, the externally visible informational cue 108 is located entirely within the crotch region 40 of the pull-on wearable article 10 and at least a portion of the externally visible informational cue 108 is in an overlapping configuration with the narrowest transverse direction region 70 of the pull-on wearable article 10. In the exemplary embodiment illustrated in FIG. 34, the overlapping portion of the externally visible informational cue 108 is illustrated as having a size dimension smaller than the size dimension of the narrowest transverse direction region 70. While the graphic illustrated in FIG. 34 is a pair of semi-circles to illustrate absorbent article wings, the absorbent article wings could be illustrated by other shapes as deemed suitable such as, for example, rectangles, semi-heart shapes, multi-domed shapes, etc.

Figure 35:
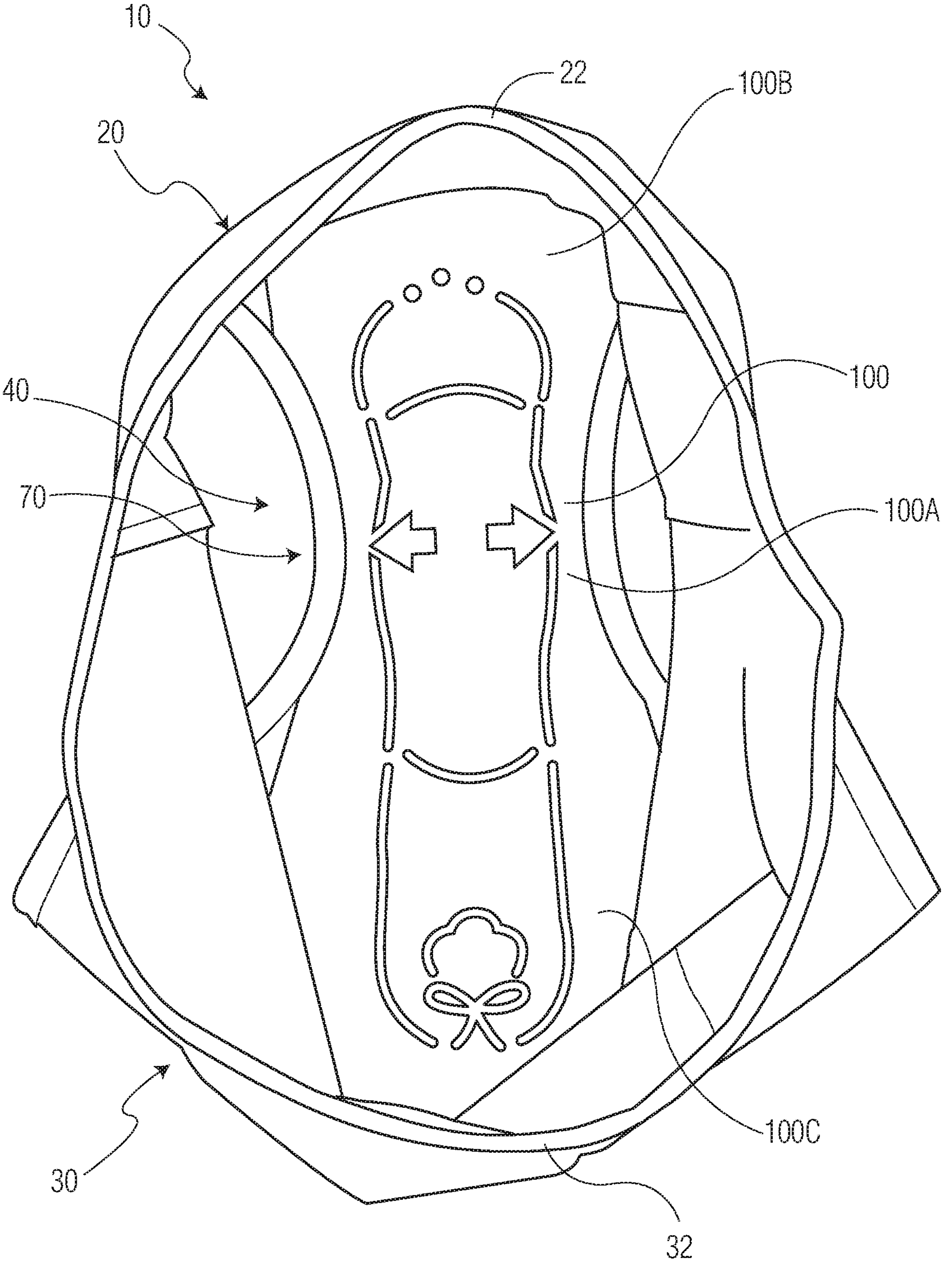
FIG. 35 is a top down view of a pull-on wearable article wherein the pull-on wearable article has an internally visible informational cue in the form of a graphic.
Figure 36:
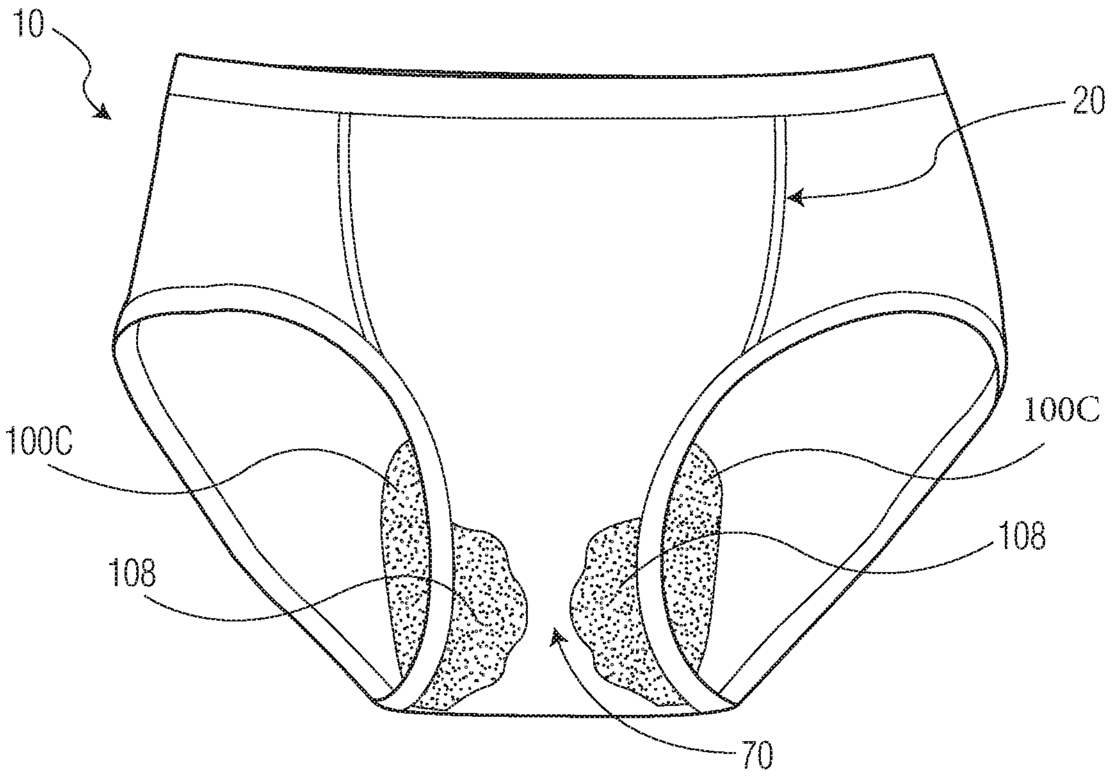
FIG. 36 is a front view of the pull-on wearable article of FIG. 35 wherein the pull-on wearable article has an externally visible informational cue.
Figure 37:
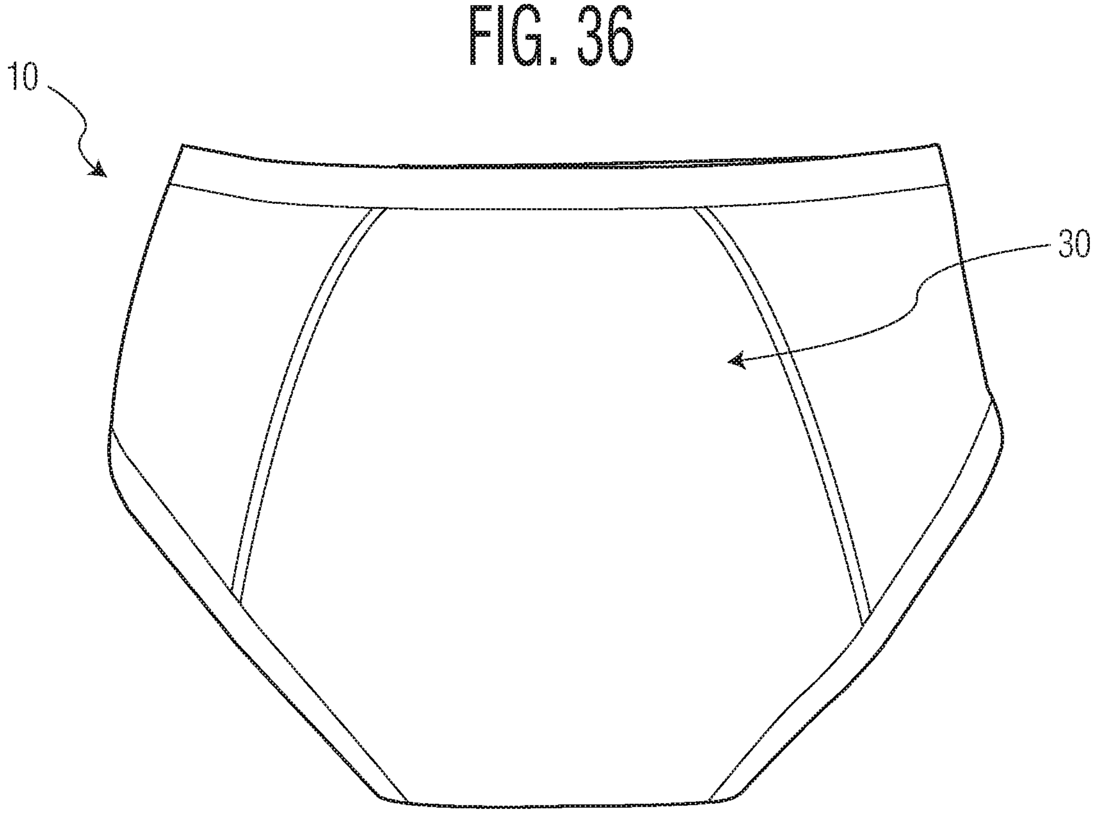
FIG. 37 is a back view of the pull-on wearable article of FIG. 35

In various embodiments, a pull-on wearable article 10 can be associated with at least one internally visible informational cue and at least one externally visible informational cue. FIGS. 35-37 provide an exemplary illustration of an embodiment of a pull-on wearable article 10 associated with at least one internally visible informational cue and at least one externally visible informational cue. FIG. 35 is a top down view of a pull-on wearable article 10, FIG. 36 is a front view of the pull-on wearable article 10 of FIG. 35, and FIG. 37 is a back view of the pull-on wearable article 10 of FIG. 35. As is visible in FIG. 35, the pull-on wearable article 10 has an internally visible informational cue 100 in the form of a graphic which is an illustrative schematic of an absorbent article in a top down view. The internally visible informational cue 100 has a first portion 100A located within the crotch region 40, a second portion 100B located within a portion of the front region 20, and a third portion 100C located within a portion of the back region 30 of the pull-on wearable article 10. The first portion 100A of the internally visible informational cue 100 schematically illustrates where the crotch region 40 of an absorbent article should be positioned while each of the second portion 100B of the internally visible informational cue 100 and the third portion 100C of the internally visible informational cue 100 schematically illustrate where the anterior region and posterior region, respectively, of an absorbent article should be positioned. As is visible in FIG. 36, the externally visible informational cue 108 is in the form of a pair of multi-domed shapes to schematically represent absorbent article wings and the location within the crotch region 40 of the pull-on wearable article 10 where absorbent article wings should be placed in embodiments wherein an absorbent article being placed into the pull-on wearable article 10 has wings.

Figure 38:
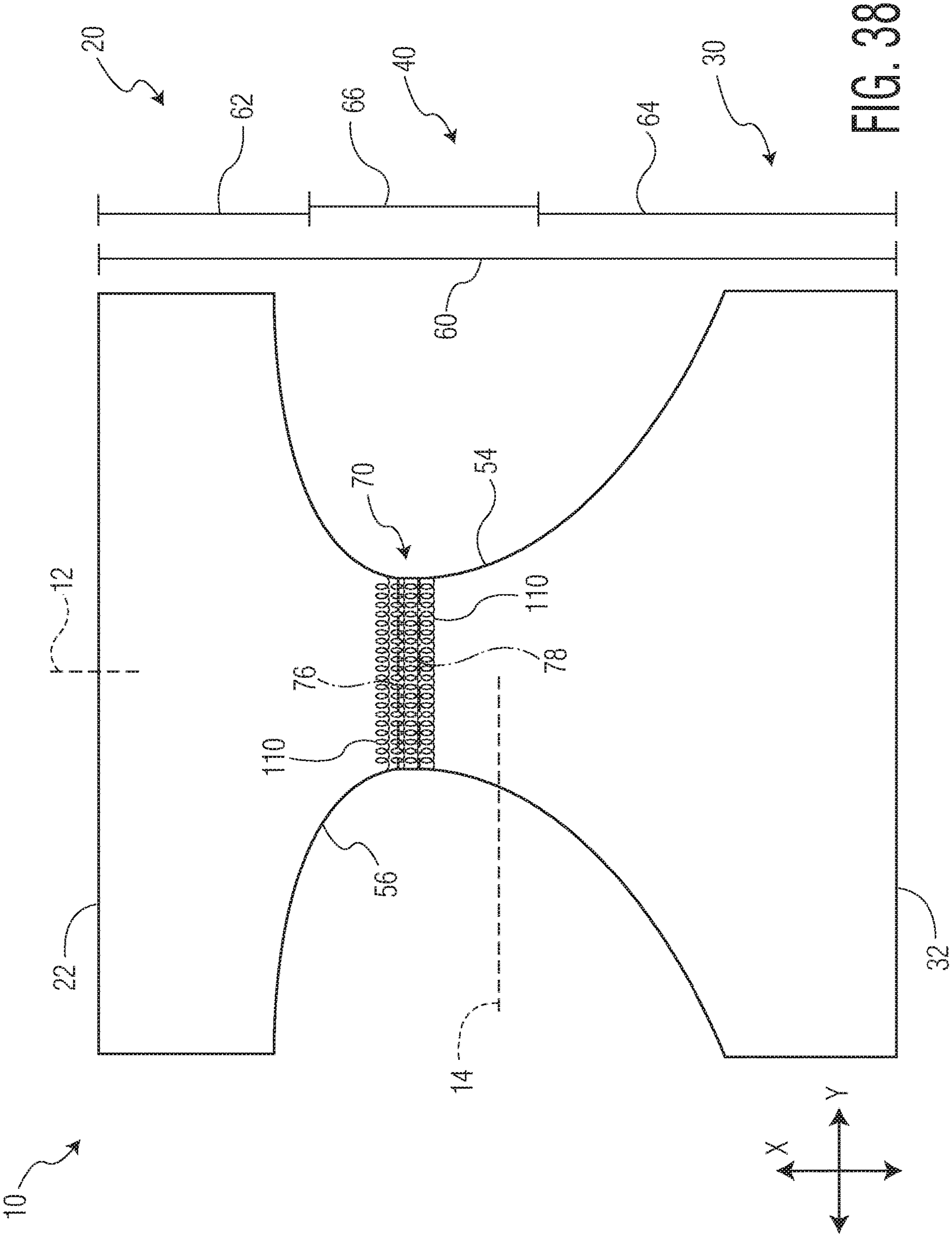
FIGS. 38 and 39 are two-dimensional illustrations of plan views of alternate embodiments of the pull-on wearable article in a longitudinally and transversely stretched and laid-flat configuration with the surface of the pull-on wearable article that faces the wearer when the pull-on wearable article is worn facing the viewer and wherein the pull-on wearable article has at least one internally visible informational cue in the form of a textural feature.
Figure 39:
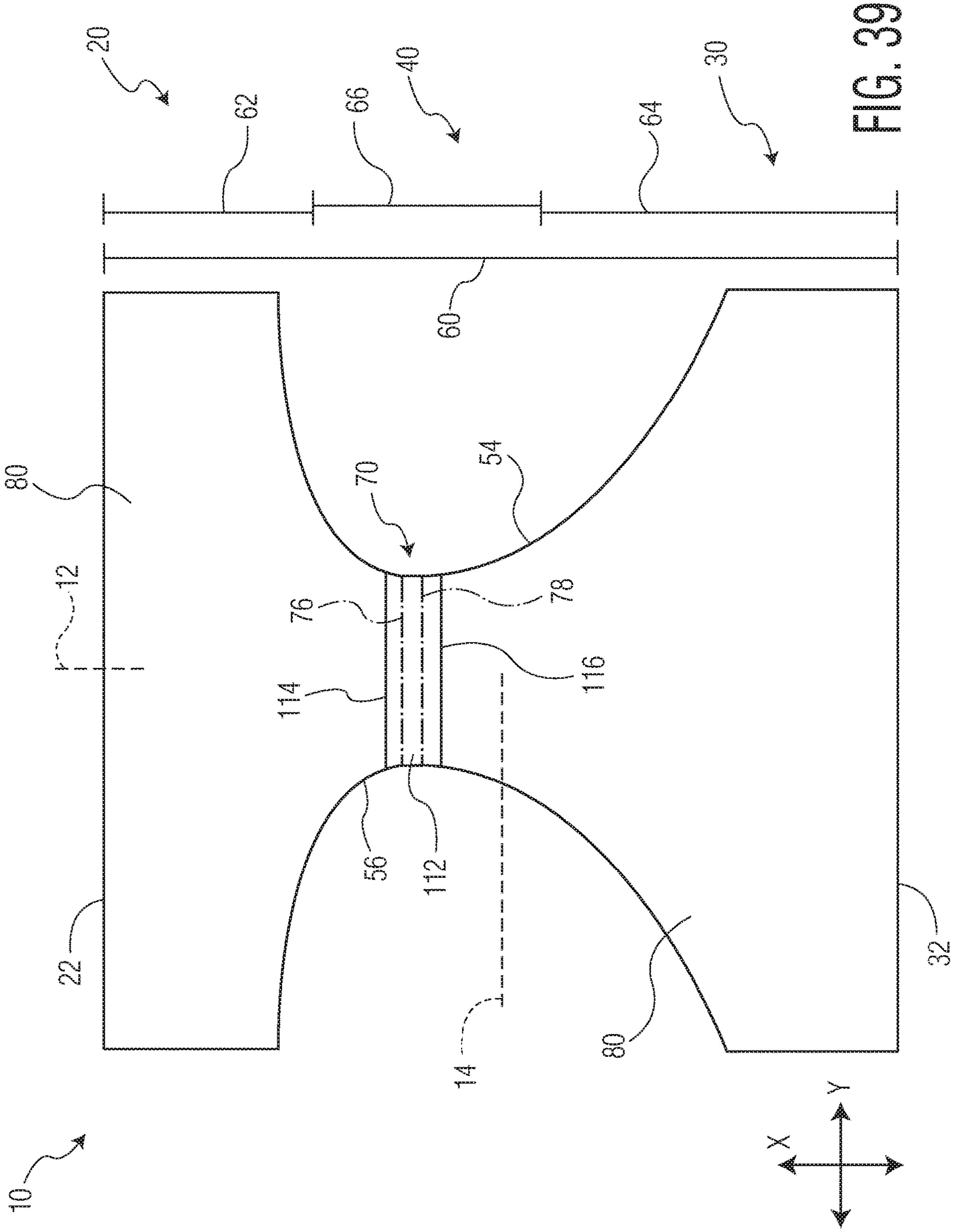

FIGS. 38 and 39 provide two-dimensional schematic illustrations of plan view of exemplary embodiments of the pull-on wearable article 10 of FIG. 1 in a longitudinally and transversely stretched and laid-flat configuration with the surface of the pull-on wearable article 10 that faces the wearer when the pull-on wearable article 10 is worn facing the viewer and wherein the pull-on wearable article 10 has at least one internally visible informational cue in the form of a textural feature. While the at least one internally visible informational cue illustrated in each of FIGS. 38 and 39 is illustrated in the form of a textural feature, it is to be understood that the at least one internally visible cue could be a graphic or a combination of a textural feature and a graphic.

FIG. 38 provides an exemplary illustration of a pull-on wearable article 10 which has an internally visible informational cue 110. The internally visible informational cue 110 can be a textural feature such as the loop portion of a hook-and-loop mating system. While the loop portion of a hook-and-loop mating system is illustrated in FIG. 38 it is to be understood that the hook portion of a hook-and-loop mating system could be the textural feature. The internally visible informational cue 110 is illustrated as being located entirely within the crotch region 40 of the pull-on wearable article 10 and at least a portion of the internally visible informational cue 110 is in an overlapping configuration with the narrowest transverse direction region 70 of the pull-on wearable article 10. In the exemplary embodiment illustrated in FIG. 38, the overlapping portion of the internally visible informational cue 110 is illustrated as having a dimension larger than the dimension of the narrowest transverse direction region 70. FIG. 39 provides an exemplary illustration of a pull-on wearable article 10 which has an internally visible informational cue 112. The internally visible informational cue 112 can be a textural feature such as the utilization of a material in the layer of the pull-on wearable article 10 that is a different type of material than the remainder of the material forming the same layer of the pull-on wearable article 10. For example, the pull-on wearable article 10 may be formed of a single layer of material, an article body layer 80, such as an elasticized blend material (e.g., elastane or spandex) and the textural feature may be formed of a cotton material. The internally visible informational cue 112, the cotton material, can be bonded to the article body layer 80 at seams 114 and 116. The internally visible informational cue 112 is illustrated as being located entirely within the crotch region 40 of the pull-on wearable article 10 and at least a portion of the internally visible informational cue 112 is in an overlapping configuration with the narrowest transverse direction region 70 of the pull-on wearable article 10. In the exemplary embodiment illustrated in FIG. 39, the overlapping portion of the internally visible informational cue 112 is illustrated as having a dimension larger than the dimension of the narrowest transverse direction region 70. Utilizing a textural feature such as the loop portion of a hook-and-loop mating system or utilizing a textural feature such as a different type of material can alter the smoothness and/or roughness of the layer of the pull-on wearable article 10, as well as vary the functionality of a portion of the layer of the pull-on wearable article 10. The use of a graphic as an informational cue may provide little benefit for a wearer of the pull-on wearable article 10 who has diminished eyesight. Providing a textural feature to the pull-on wearable article 10 can communicate to such a wearer the location of the narrowest transverse direction region 70 of the pull-on wearable article 10 and enable proper placement of the crotch region of an absorbent article into the pull-on wearable article 10. In various embodiments, the textural feature itself may assist in securing the absorbent article to the pull-on wearable article 10.

As described herein, the present disclosure is directed towards a pull-on wearable article which has a front region, a back region, and a crotch region located between the front region and the back region. The pull-on wearable article has a permanent closed waist configuration providing the pull-on wearable article with a waist opening and two leg openings. An informational cue can be associated with the pull-on wearable article to communicate to the wearer of the pull-on wearable article where to place the crotch region of an absorbent article when placing the absorbent article into the pull-on wearable article. The informational cue triggers a cognitive response in the wearer of the pull-on wearable article and can be an attention attracting graphic, textural feature, or a combination thereof.

Figure 40:
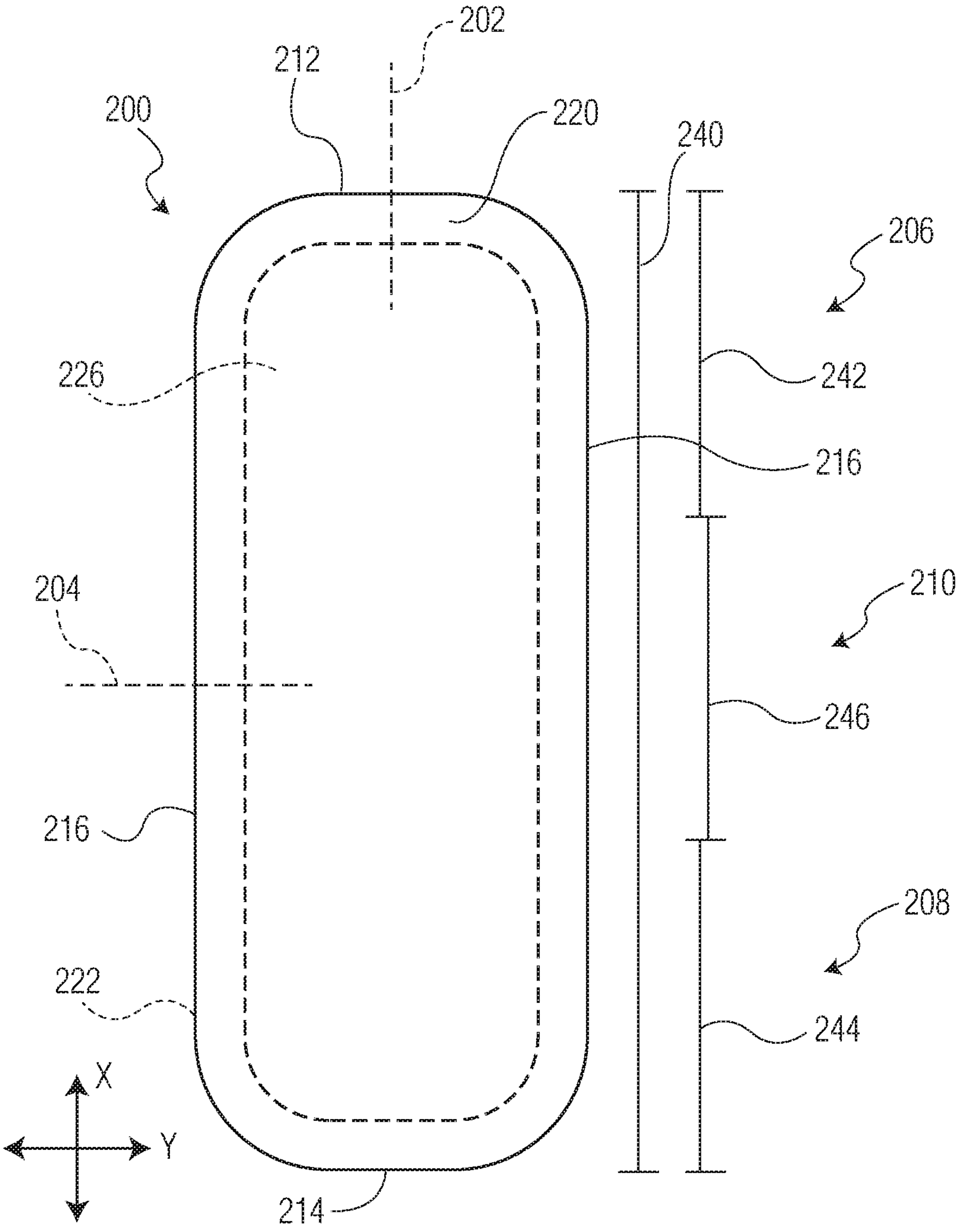
FIG. 40 is a top view of an embodiment of an absorbent article.

Referring to FIGS. 40-44, an absorbent article 200 is exemplified in the form of a feminine hygiene product such as a menstrual pad or sanitary napkin. FIG. 40 provides a top down view of the exemplary embodiment of the absorbent article 200 and FIGS. 41-44 provide exemplary embodiments of bottom views of the absorbent article 200 of FIG. 40. The absorbent article 200 can have a longitudinal direction (X) and a transverse direction (Y). The absorbent article 200 can have a longitudinal axis 202 and a transverse axis 204. The absorbent article 200 can have an anterior region 206, a posterior region 208, and a crotch region 210 positioned between the anterior region 206 and the posterior region 208. When the absorbent article 200 is in use, the crotch region 210 can be positioned at the primary location of exudate discharge from the wearer of the absorbent article 200.

The absorbent article 200 can have an anterior edge 212, a posterior edge 214 opposed to the anterior edge 212, and a pair of opposing longitudinal direction side edges 216 extending between and connecting the anterior edge 212 and the posterior edge 214. The absorbent article 200 can have a wearer facing, liquid permeable topsheet layer 220 and a garment facing, liquid impermeable backsheet layer 222. An absorbent core 226 can be positioned between the topsheet layer 220 and the backsheet layer 222. The topsheet layer 220 and the backsheet layer 222 can both extend beyond the outermost perimeter edge of the absorbent core 226 and can be peripherally bonded together using known bonding techniques to form a sealed peripheral region. For example, the topsheet layer 220 and the backsheet layer 222 can be bonded together by adhesive bonding, ultrasonic bonding, or any other suitable bonding technique known in the art.

The topsheet layer 220 defines a body facing surface of the absorbent article 200 that may directly contact the body of the wearer and is liquid permeable to receive body exudates. The topsheet layer 220 is desirably provided for comfort and functions to direct body exudates away from the body of the wearer, through its own structure, and towards the absorbent core 226. The topsheet layer 220 desirably retains little to no liquid in its structure, so that it provides a relatively comfortable and non-irritating surface next to the skin of the wearer of the absorbent article 200.

The topsheet layer 220 can be a single layer of material, or alternatively, can be multiple layers that have been laminated together. The topsheet layer 220 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 220.

In various embodiments the topsheet layer 220 can be constructed from various nonwoven webs such as meltblown webs, spunbond webs, hydroentangled spunlace webs, or through air bonded carded webs. Examples of suitable topsheet layer 220 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 220 can be a bonded carded web made of polypropylene and polyethylene such as that obtainable from Sandler Corp., Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 220, each of which is hereby incorporated by reference thereto in its entirety. Additional topsheet layer 220 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 220 may contain a plurality of apertures formed therethrough to permit body exudates to pass more readily into the absorbent core 226. The apertures may be randomly or uniformly arranged throughout the topsheet layer 220. The size, shape, diameter, and number of apertures may be varied to suit an absorbent article's 200 particular needs.

In various embodiments, the topsheet layer 220 can have a basis weight ranging from about 5, 10, 15, 20, or 25 gsm to about 50, 100, 120, 125, or 150 gsm. For example, in an embodiment, a topsheet layer 220 can be constructed from a through air bonded carded web having a basis weight ranging from about 15 gsm to about 100 gsm. In another example, a topsheet layer 220 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics, and others.

In various embodiments, the topsheet layer 220 can be at least partially hydrophilic. In various embodiments, a portion of the topsheet layer 220 can be hydrophilic and a portion of the topsheet layer 220 can be hydrophobic. In various embodiments, the portions of the topsheet layer 220 which can be hydrophobic can be either an inherently hydrophobic material or can be a material treated with a hydrophobic coating.

In various embodiments, the topsheet layer 220 can be a multicomponent topsheet layer 220 such as by having two or more different nonwoven or film materials, with the different materials placed in separate locations in the transverse direction (Y) of the absorbent article 200. For example, the topsheet layer 220 can be a two layer or multicomponent material having a central portion positioned along and straddling a longitudinal axis 202 of an absorbent article 200, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 220 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In various embodiments, a central portion of a topsheet layer 220 can be positioned symmetrically about the absorbent article 200 longitudinal axis 202. Such central longitudinally directed central portion can be a through air bonded carded web ("TABCW") having a basis weight between about 15 and about 100 gsm. Previously described nonwoven, woven, and aperture film topsheet layer materials may also be used as the central portion of a topsheet layer 220. In various embodiments, the central portion can be constructed from a TABCW material having a basis weight from about 20 gsm to about 50 gsm such as is available from Xiamen Yanjan Industry, Beijing, DaYuan Nonwoven Fabrics, and others. Alternatively, aperture films, such as those available from such film suppliers as Texol, Italy and Tredegar, U.S.A. may be utilized. Different nonwoven, woven, or film sheet materials may be utilized as the side portions of the topsheet layer 220. The selection of such topsheet layer 220 materials can vary based upon the overall desired attributes of the topsheet layer 220. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 40 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 200 side edges when viewed from above the topsheet layer 220. The film layer may also serve as a barrier layer to prevent rewet of the topsheet layer 220 as well as to prevent the flow of fluid off the side edges of the absorbent article 200. In various embodiments, the side portions can be laminates such as a spunbond-meltblown-meltblown-spunbond layer ("SMMS") laminate, spunbond-film laminate, or alternatively, other nonwoven laminate combinations.

The absorbent article 200 can have an absorbent core 226 positioned between the topsheet layer 220 and the backsheet layer 222. The absorbent core 226 is designed to absorb body exudates, including menstrual fluid, blood, urine, and other bodily fluids such as sweat and vaginal discharge. The absorbent core 226 can generally be any single layer structure which can demonstrate some level of compressibility, conformability, be non-irritating to a wearer's skin, and capable of absorbing and retaining liquids and other body exudates.

In various embodiments, the absorbent core 226 can be formed from a variety of different materials. For example, the absorbent core 226 can include a layer of absorbent material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In various embodiments, the absorbent material can include a matrix of cellulosic fluff. In various embodiments, the absorbent material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 226 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 226 in any amount as desired.

The absorbent core 226 can be provided in any shape as deemed suitable for the absorbent article 200 such as, but not limited to, oblong, oval, rectangular, tear-dropped, dog-bone, hourglass, racetrack, triangular, and elliptical as well as any other geometric shape as deemed suitable for the absorbent article 200. In various embodiments, the shape of the absorbent core 226 can have a shape which provides symmetry about at least one axis, longitudinal 202 and/or transverse 204, of the absorbent article 200. In various embodiments, the shape of the absorbent core 226 can have a shape which provides symmetry about each axis, longitudinal 202 and transverse 204, of the absorbent article 200. In various embodiments, the shape of the absorbent core 226 can be one in which there is no symmetry of the absorbent core 226 about either of the axes, longitudinal 202 or transverse 204 of the absorbent article 200.

Regardless of the combination of absorbent materials used in the absorbent core 226, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

By way of example, suitable materials and/or structures for the absorbent core 226 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al. each of which is hereby incorporated by reference thereto in its entirety.

In various embodiments, an absorbent core 226 can be a single layer structure and can include, for example, a matrix of cellulosic fluff and superabsorbent material. In various embodiments, an absorbent core 226 can have at least two layers of material, such as, for example, a body facing layer and a non-body facing layer. In various embodiments, the two layers can be identical to each other. In various embodiments, the two layers can be different from each other. In such embodiments, the two layers can provide the absorbent article 200 with different absorption properties as deemed suitable. In various embodiments, the body facing layer of the absorbent core 226 may be constructed of an airlaid material and the non-body facing layer of the absorbent core 226 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

The backsheet layer 222 is generally liquid impermeable and is the portion of the absorbent article 200 which faces the garments of the wearer. The backsheet layer 222 can permit the passage of air or vapor out of the absorbent article 200 while still blocking the passage of liquids. Any liquid impermeable material may generally be utilized to form the backsheet layer 222. The liquid impermeable layer 222 can be composed of a single layer or multiple layers, and these one or more layers can themselves comprise similar or different materials. Suitable material that may be utilized can be a microporous polymeric film, such as a polyolefin film or polyethylene or polypropylene, nonwovens, and nonwoven laminates, and film/nonwoven laminates. The particular structure and composition of the backsheet layer 222 can be selected from various known films and/or fabrics with the particular material being selected as appropriate to provide the desired level of liquid barrier, strength, abrasion resistance, tactile properties, aesthetics, and so forth. In various embodiments, a polyethylene film can be utilized that can have a thickness in the range of from about 0.2 or 0.5 mils to about 3.0 or 5.0 mils. An example of a backsheet layer 222 can be a polyethylene film such as that obtainable from Pliant Corp., Schaumburg, IL, USA. Another example can include calcium carbonate-filled polypropylene film. In still another embodiment, the backsheet layer 222 can be a hydrophobic nonwoven material with water barrier properties such as a nonwoven laminate, an example of which can be a spunbond, meltblown, meltblown, spunbond, four-layered laminate.

The backsheet layer 222 can, therefore, be of a single or multiple layer construction, such as of multiple film layers or laminates of film and nonwoven fibrous layers. Suitable backsheet layers 44 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

The backsheet layer 222 of the absorbent article 200 can be provided with a garment attachment adhesive 228 which can be located on the non-body facing surface 224 of the backsheet layer 222 for attachment of the absorbent article 200 to a wearer's undergarment. The garment attachment adhesive 228 can be provided in any suitable arrangement and/or pattern on the non-body facing surface 224 of the backsheet layer 222 as deemed suitable. In various embodiments, the garment attachment adhesive 228 can be provided in any amount suitable on the non-body facing surface 224 of the backsheet layer 222. In various embodiments, the garment attachment adhesive 228 can be provided in any pattern as deemed suitable, such as, but not limited to, stripes, swirls, dots, or the like, or combinations thereof. The garment attachment adhesive 228 can be provided in any location on the non-body facing surface 224 of the backsheet layer 222 as deemed suitable.

In various embodiments, the backsheet layer 222 of the absorbent article 200 can be associated with at least one complementary informational cue. A complementary informational cue can be associated with the backsheet layer 222 of the absorbent article 200 to communicate to the wearer of the absorbent article 200 where to place at least the crotch region 210 of the absorbent article 200 when placing the absorbent article 200 into the pull-on wearable article 10. The complementary informational cue triggers a cognitive response in the wearer of the absorbent article 200 and can be an attention attracting graphic, textural feature, or a combination thereof.

In various embodiments, the absorbent article 200 can be associated with at least one complementary informational cue. In various embodiments, the complementary informational cue can be located within the crotch region 210 of the absorbent article 200. In various embodiments, the absorbent article 200 can have multiple complementary informational cues wherein a first complementary informational cue is located within the crotch region 210 and a second complementary informational cue is located within the front region 206 wherein the first complementary informational cue is separate from and spaced apart from the second complementary informational cue. In various embodiments, the absorbent article 200 can have multiple complementary informational cues wherein a first complementary informational cue is located in the crotch region 210, a second complementary informational cue is located within the front region 206, and a third complementary informational cue is located within the back region 208 wherein the first complementary informational cue, the second complementary informational cue, and the third complementary informational cue are separate from and spaced apart from each other.

In various embodiments in which the complementary informational cue is a graphic, the graphic can be provided in the form of a shape and/or image. For example, the graphic can be formed of one or more dots, one or more lines, one or more arrows, one or more regular or irregular shapes (such as circles, ovals, triangles, rectangles, squares, ellipses, diamonds, etc), or combinations thereof. In various embodiments, the graphic can have a color wherein the color can either be uniform or variable from either one hue to another or variable from light to dark. In various embodiments, the graphic can include an image of an object readily recognizable by a human viewer. In various embodiments in which the complementary informational cue is a graphic, the graphic may be printed on the interior facing surface of the backsheet layer 222 of the absorbent article 200, the exterior facing surface of the backsheet layer 222 of the absorbent article 200, or both the interior and the exterior facing surfaces of the backsheet layer 222 of the absorbent article 200.

In various embodiments in which the complementary informational cue is a textural feature, the textural feature can alter the feel of a portion of the backsheet 222 of the absorbent article 200. For example, a textural feature may alter the smoothness, may alter the roughness, may vary the reflectivity, may enhance a color, may replace a portion of the material forming the layer with a different type of material, may vary the functionality of a portion of the backsheet layer 222, or combinations thereof, of a portion of layer of the absorbent article 200. In various embodiments, the textural feature may assist in securing the absorbent article 200 to the pull-on wearable article 10.

Absorbent articles 200 can have variable lengths, such as, for example, an absorbent article 200 intended for overnight usage or for accommodating a heavy menstrual flow may have a longer total longitudinal direction length 240 between the anterior edge 212 and the posterior edge 214 than the total longitudinal direction length 240 between the anterior edge 212 and the posterior edge 214 of an absorbent article 200 intended for regular or moderate menstrual flow. For example, an absorbent article 200 intended for a heavy menstrual flow or overnight usage of the absorbent article 200, may have an anterior region 206 and a crotch region 210 which may have a similar longitudinal direction length when compared with an absorbent article 200 for moderate or regular menstrual flow, however, the posterior region 208 of the absorbent article 200 intended for a heavy menstrual flow or overnight usage may be extended in longitudinal length greater than that of the posterior region 208 of a regular or moderate absorbent article 200 in order to accommodate the intended usage needs.

Figure 45:
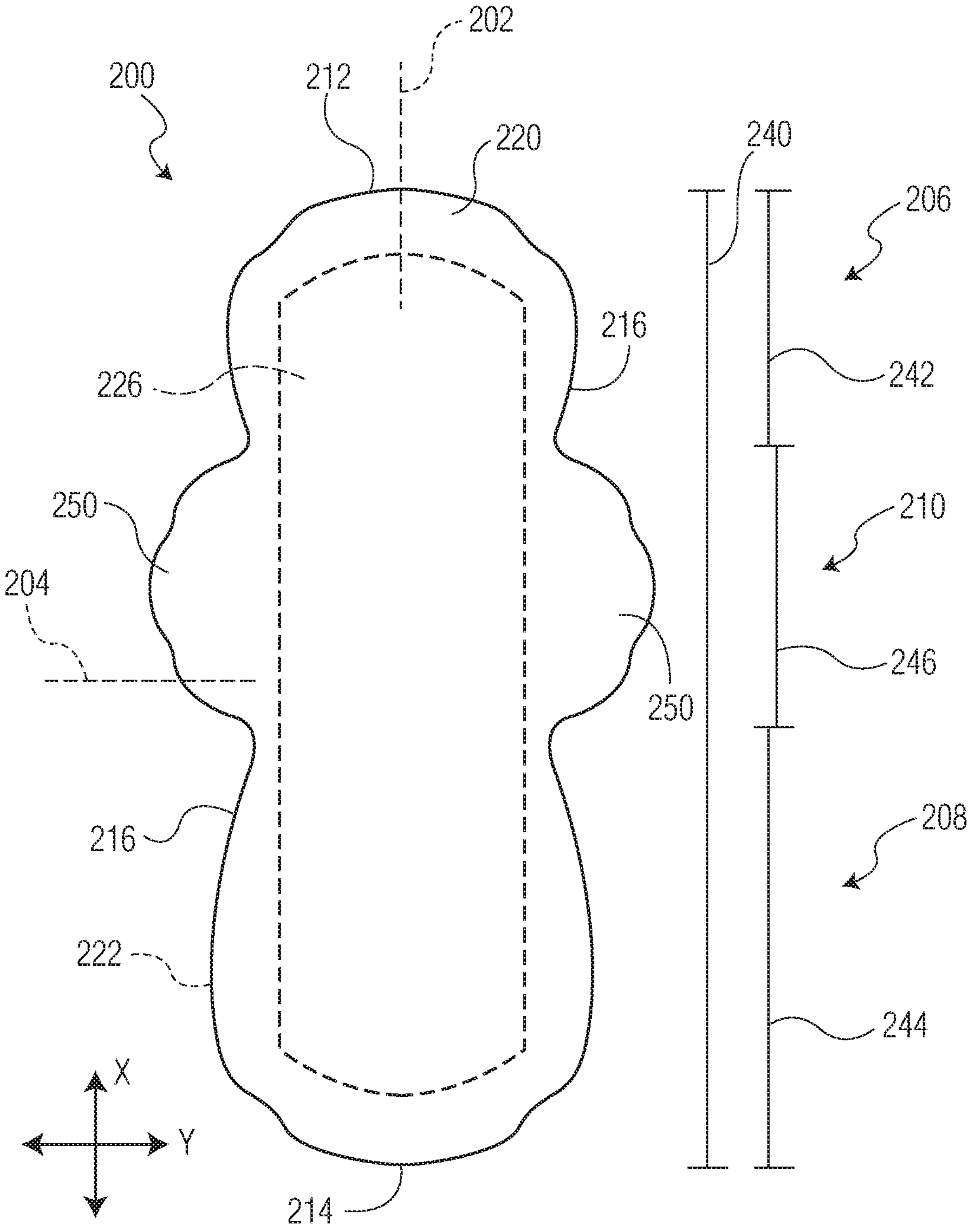
FIG. 45 is a top view of an alternate embodiment of an absorbent article.

As the total longitudinal direction length 240 can vary among absorbent articles 200, the mid-point of the crotch region 210 of an absorbent article 200 will not always be located at the intersection of the longitudinal axis 202 and the transverse axis 204 of the absorbent article 200. FIG. 40 is a top down view of an illustration of an embodiment of an absorbent article 200. The absorbent article 200 illustrated in FIG. 40 has a total longitudinal direction length 240 from the anterior edge 212 to the posterior edge 214 wherein the anterior region length 242, posterior region length 244, and crotch region length 246 are evenly apportioned along the longitudinal direction axis 202 and each of the anterior region length 242, posterior region length 244, and crotch region length 246 are each approximately one-third of the total longitudinal direction length 240 of the absorbent article 200. In the embodiment illustrated in FIG. 40, the mid-point of the crotch region 210 is located at the intersection of the longitudinal direction axis 202 and the transverse direction axis 204. FIG. 45 is a top down view of an illustration of another embodiment of an absorbent article 200. The absorbent article 200 illustrated in FIG. 45 has a total longitudinal direction length 240 from the anterior edge 212 to the posterior edge 214 wherein the anterior region length 242, posterior region length 244, and crotch region length 246 are not evenly apportioned along the longitudinal direction axis 202. In the embodiment illustrated in FIG. 45, the posterior region length 244 is longer than each of the anterior region length 242 and the crotch region length 246. In the exemplary embodiment illustrated in FIG. 45, the mid-point of the crotch region 210 is not located at the intersection of the longitudinal direction axis 202 and the transverse direction axis 204. Rather the mid-point of the crotch region 210 is located between the transverse direction axis 204 and the anterior edge 212 of the absorbent article 200. In various embodiments, due to the variation in total lengths available for an absorbent article 200 based on intended usage of the absorbent article 200, the mid-point of the crotch region 210 of the absorbent article 20 can be located at a distance, as measured from the anterior edge 212, from about 30% to about 50% of the total longitudinal direction length 240, measured as the distance from the anterior edge 212 to the posterior edge 214, of the absorbent article 200. In various embodiments, a complementary informational cue can be positioned at the mid-point of the crotch region 210 of the absorbent article 200. Such a placement of the complementary informational cue can assist the wearer of the absorbent article 200 with identifying the crotch region 210 of the absorbent article 200 and can assist with placing the crotch region 210 of the absorbent article 200 within the crotch region 40 of the pull-on wearable article 10.

As described herein, the informational cue associated with the pull-on wearable article 10 can communicate to the wearer of the pull-on wearable article 10 where to place the crotch region of an absorbent article 200 when placing the absorbent article 200 into the pull-on wearable article 10. The complementary informational cue associated with the backsheet 222 of the absorbent article 200 can communicate to the wearer of the absorbent article 200 the location of the crotch region 210 of the absorbent article 200. The informational cue of the pull-on wearable article 10 and the complementary informational cue of the absorbent article 200 can create a system of a pull-on wearable article 10 and an absorbent article 200 for the wearer. The system of the pull-on wearable article 10 and the absorbent article 200 can assist the wearer with appropriate placement of the absorbent article 200 into the pull-on wearable article 10 resulting in an increased peace of mind for the wearer while wearing the absorbent article 200. The complementary informational cue of the absorbent article 200 can align, match, overlap, complete, fill-in, contextually relate to, highlight, etc. the informational cue of the pull-on wearable article 10. In various embodiments in which the complementary informational cue 230 is a textural feature, the complementary informational cue 230 can further assist in securing the absorbent article 200 to the pull-on wearable article 10.

Referring to FIGS. 40-44, an embodiment of an absorbent article 200 is illustrated in the form of a sanitary napkin or menstrual pad. FIG. 40 is a top down view of an illustration of an embodiment of an absorbent article 200. FIGS. 41-44 are bottom views of alternate embodiments, of the absorbent article 200 of FIG. 40. The absorbent article 200 illustrated in FIG. 40 has a total longitudinal direction length 240 from the anterior edge 212 to the posterior edge 214 wherein the anterior region length 242, posterior region length 244, and crotch region length 246 are evenly apportioned along the longitudinal direction axis 202 and each of the anterior region length 242, posterior region length 244, and crotch region length 246 are each approximately one-third of the total longitudinal direction length 240 of the absorbent article 200. In the embodiment illustrated in FIG. 40, the mid-point of the crotch region 210 is located at the intersection of the longitudinal direction axis 202 and the transverse direction axis 204.

Figure 41:
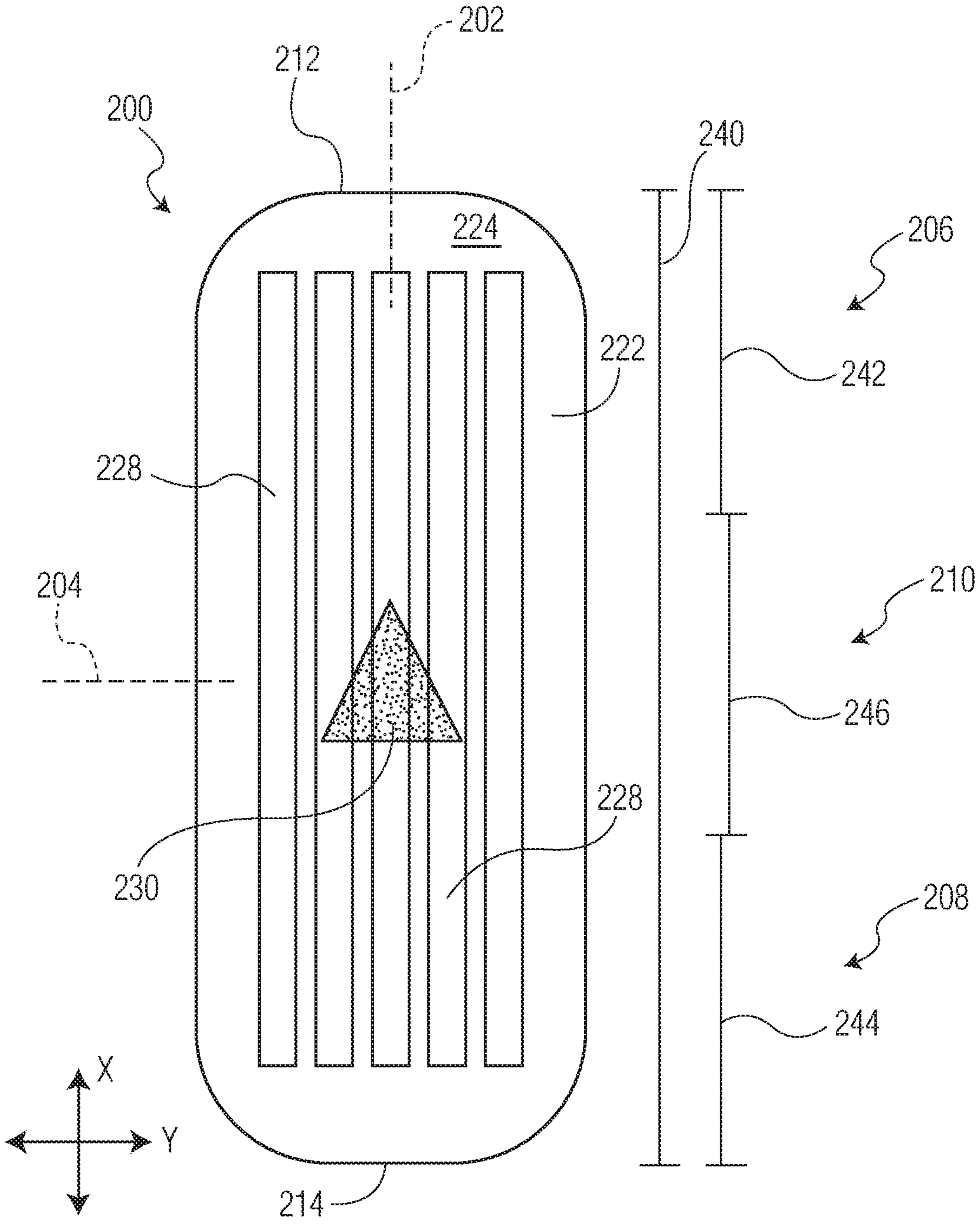
FIGS. 41-44 are bottom views of alternate embodiments of the absorbent article of FIG. 40.

FIG. 41 provides an exemplary illustration of a complementary informational cue 230 located within the crotch region 210 and positioned at the mid-point of the crotch region 210. The complementary informational cue 230 is illustrated in the form of a graphic such as a triangle, however, it is to be understood that the complementary informational cue 230 could be a textural feature or a combination of a graphic and a textural feature. The complementary informational cue 230 can communicate with the wearer of the absorbent article 200 the location of the mid-point of the crotch region 210 of the absorbent article 200 and can also align with an internally visible informational cue, such as internally visible informational cue 100 illustrated in FIG. 28. The wearer of the absorbent article 200 can match the complementary informational cue 230 of the absorbent article 200 to the internally visible informational cue 100 of the pull-on wearable article 10 for proper placement of the absorbent article 200 into the pull-on wearable article 10.

Figure 42:
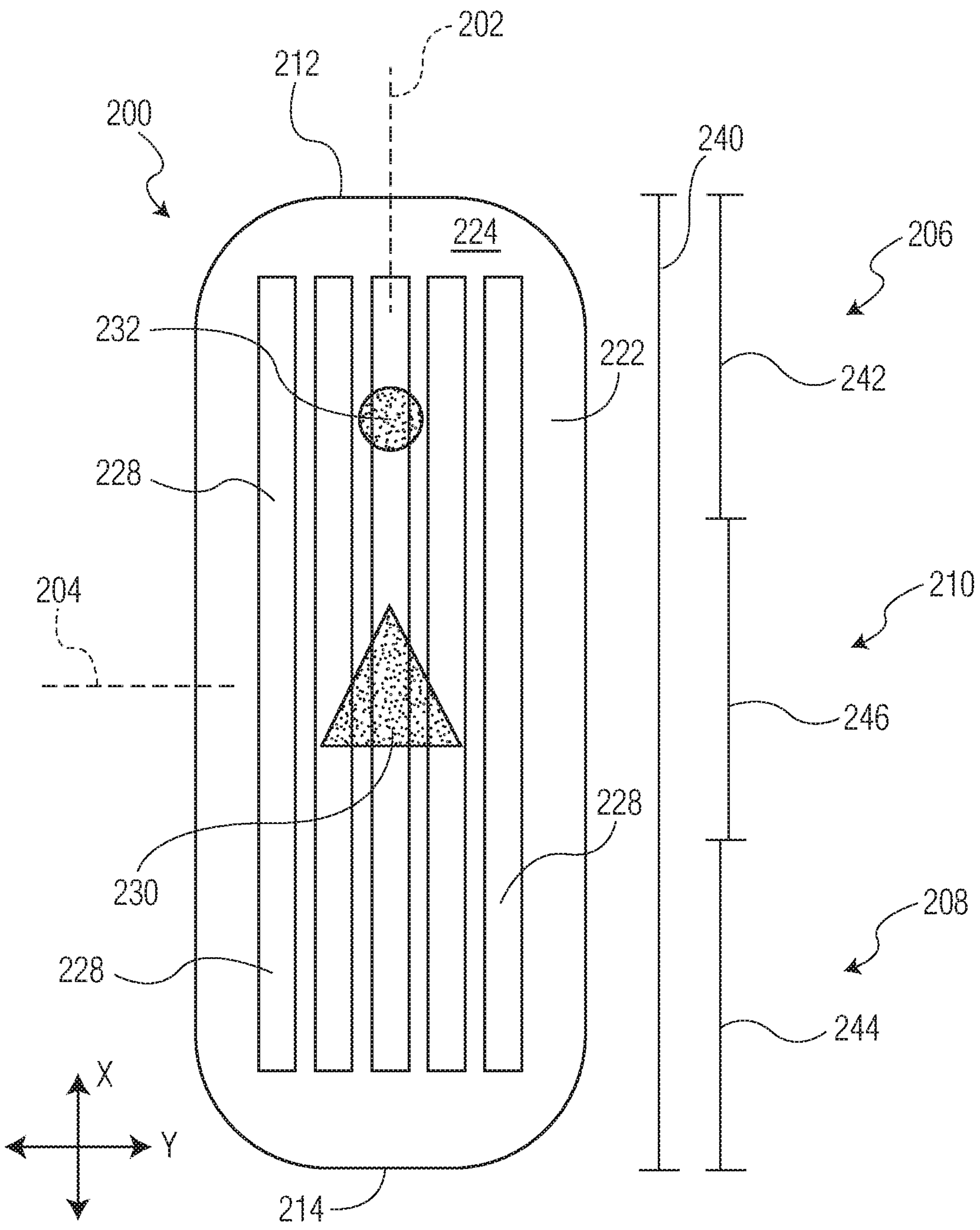

FIG. 42 provides an exemplary illustration of an absorbent article 200 which has two complementary informational cues, a first complementary informational cue 230 and a second complementary informational cue 232. The first complementary informational cue 230 is illustrated in the form of a graphic such as a triangle and is located at the mid-point of the crotch region 210 of the absorbent article 200. The second complementary information cue 232 is illustrated in the form of a graphic such as a circle and is located in the anterior region 206 of the absorbent article 200. It is to be understood that the first complementary informational cue 230 and the second complementary informational cue 232 could be textural features or a combination of a graphic and a textural feature. The first complementary informational cue 230 can communicate with the wearer of the absorbent article 200 the location of the mid-point of the crotch region 210 of the absorbent article 200 and can also align with an internally visible informational cue, such as internally visible informational cue 100 illustrated in FIG. 30. The second complementary informational cue 232 can communicate with the wearer of the absorbent article 200 the location of the anterior region 206 of the absorbent article 200 and can also align with an internally visible informational cue, such as internally visible informational cue 102 illustrated in FIG. 30. The wearer of the absorbent article 200 can match the first complementary informational cue 230 of the absorbent article 200 to the internally visible informational cue 100 of the pull-on wearable article 10 and the second complement informational cue 232 to the internally visible informational cue 102 of the pull-on wearable article 10 for proper placement of the absorbent article 200 into the pull-on wearable article 10.

Figure 43:
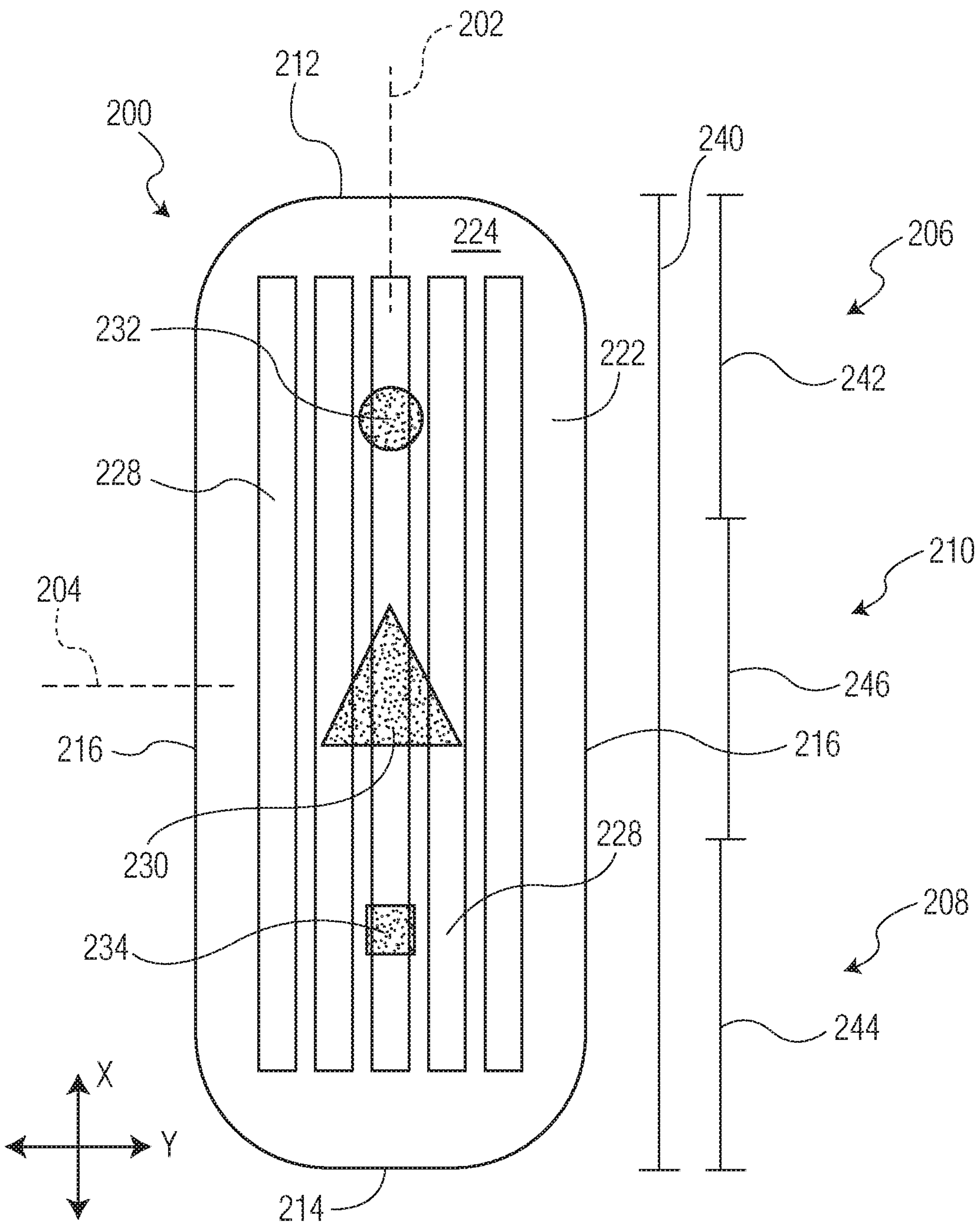

FIG. 43 provides an exemplary illustration of an absorbent article 200 which has three complementary informational cues, a first complementary informational cue 230, a second complementary informational cue 232, and a third complementary informational cue 234. The first complementary informational cue 230 is illustrated in the form of a graphic such as a triangle and is located at the mid-point of the crotch region 210 of the absorbent article 200. The second complementary information cue 232 is illustrated in the form of a graphic such as a circle and is located in the anterior region 206 of the absorbent article 200. The third complementary information cue 234 is illustrated in the form of a graphic such as a square and is located in the posterior region 208 of the absorbent article 200. It is to be understood that the first complementary informational cue 230, the second complementary informational cue 232, and the third complementary cue 234 could be textural features or a combination of a graphic and a textural feature. The first complementary informational cue 230 can communicate with the wearer of the absorbent article 200 the location of the mid-point of the crotch region 210 of the absorbent article 200 and can also align with an internally visible informational cue, such as internally visible informational cue 100 illustrated in FIG. 32. The second complementary informational cue 232 can communicate with the wearer of the absorbent article 200 the location of the anterior region 206 of the absorbent article 200 and can also align with an internally visible informational cue, such as internally visible informational cue 102 illustrated in FIG. 32. The third complementary informational cue 234 can communicate with the wearer of the absorbent article 200 the location of the posterior region 208 of the absorbent article 200 and can also align with an internally visible informational cue, such as internally visible informational cue 104 illustrated in FIG. 32. The wearer of the absorbent article 200 can match the first complementary informational cue 230 of the absorbent article 200 to the internally visible informational cue 100 of the pull-on wearable article 10, the second complement informational cue 232 to the internally visible informational cue 102 of the pull-on wearable article 10, and the third complementary informational cue 234 to the third internally visible informational cue 104 for proper placement of the absorbent article 200 into the pull-on wearable article 10.

Figure 44:
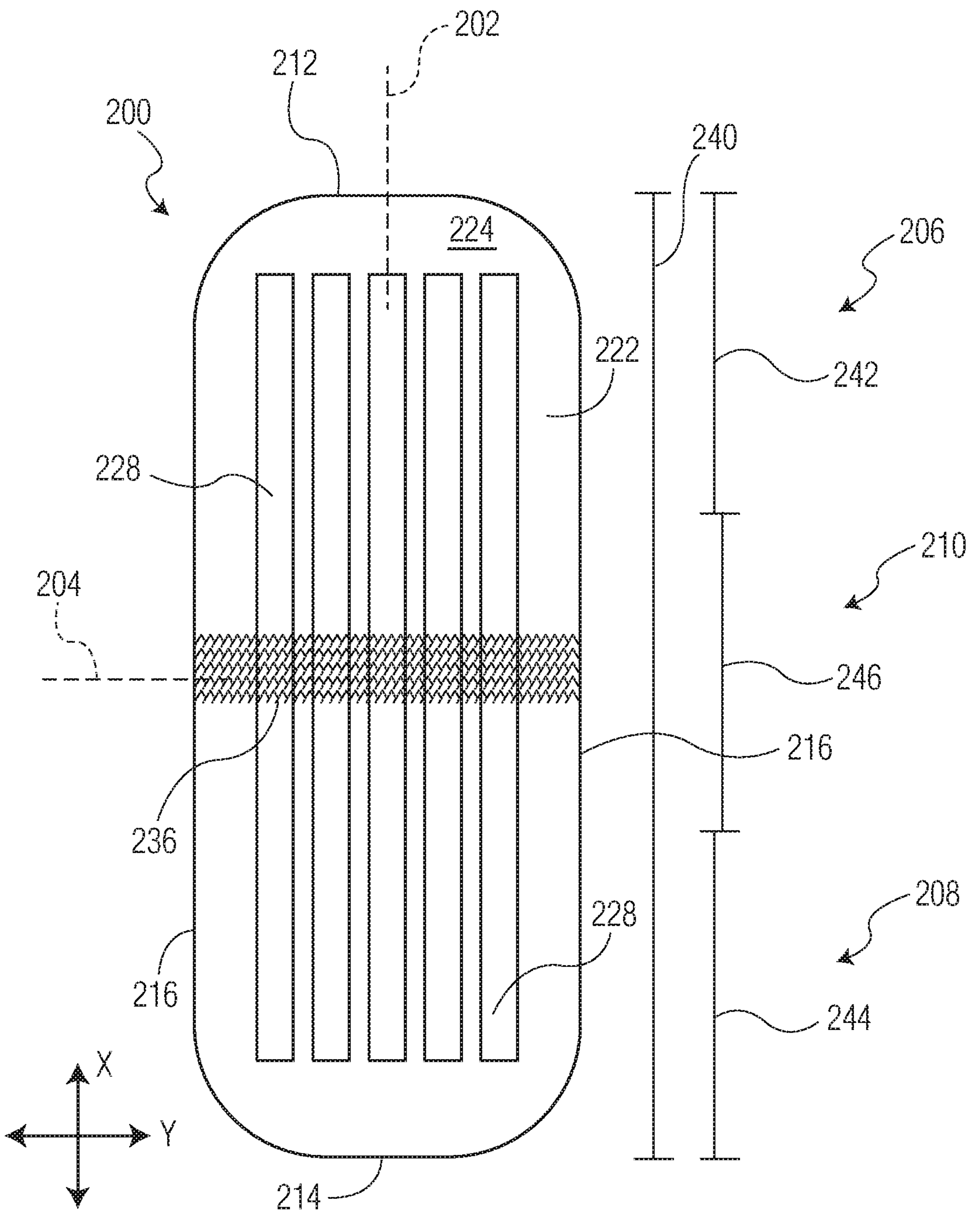

FIG. 44 provides an exemplary illustration of a complementary informational cue 236 located within the crotch region 210 and positioned at the mid-point of the crotch region 210. The complementary informational cue 236 is illustrated in the form of a textural feature, such as, for example, the hooks of a hook-and-loop mating system, however, it is to be understood that the complementary informational cue 236 could be a graphic or a combination of a graphic and a textural feature. The complementary informational cue 236 can communicate with the wearer of the absorbent article 200 the location of the mid-point of the crotch region 210 of the absorbent article 200 and can also align with an internally visible informational cue, such as internally visible informational cue 110 illustrated in FIG. 38. The wearer of the absorbent article 200 can match the complementary informational cue 236 of the absorbent article 200 to the internally visible informational cue 110 of the pull-on wearable article 10 for proper placement of the absorbent article 200 into the pull-on wearable article 10. In various embodiments in which the complementary informational cue 236 is a textural feature, the textural feature can assist in securing the absorbent article 200 to the pull-on wearable article 10. For example, the informational cue 110 and the complementary informational cue 236 can be a hook-and-loop mating system, a snap mating system, a button-and-button hole mating system, etc. For example, the informational cue 110 illustrated in FIG. 38 is a loop portion of a hook-and-loop mating system and the complementary informational cue 236 illustrated in FIG. 44 is the hook portion of a hook-and-loop mating system wherein the two portions, the loop and the hook, can mate to assist in securing the absorbent article 200 to the pull-on wearable article 10.

Referring to FIGS. 45-49, an embodiment of an absorbent article 200 is illustrated in the form of a sanitary napkin or menstrual pad. FIG. 45 is a top down view of an illustration of an embodiment of an absorbent article 200. FIGS. 46-49 are bottom views of alternate embodiments, of the absorbent article 200 of FIG. 45. The absorbent article 200 illustrated in FIG. 45 has a total longitudinal direction length 240 from the anterior edge 212 to the posterior edge 214 wherein the anterior region length 242, posterior region length 244, and crotch region length 246 are not evenly apportioned along the longitudinal direction axis 202. In the embodiment illustrated in FIG. 45, the posterior region length 244 is longer than each of the anterior region length 242 and the crotch region length 246. In the exemplary embodiment illustrated in FIG. 45, the mid-point of the crotch region 210 is not located at the intersection of the longitudinal direction axis 202 and the transverse direction axis 204. Rather the mid-point of the crotch region 210 is located between the transverse direction axis 204 and the anterior edge 212 of the absorbent article 200. In various embodiments, due to the variation in total lengths available for an absorbent article 200 based on intended usage of the absorbent article 200, the mid-point of the crotch region 210 of the absorbent article 20 can be located at a distance, as measured from the anterior edge 212, from about 30% to about 50% of the total longitudinal direction length 240, measured as the distance from the anterior edge 212 to the posterior edge 214, of the absorbent article 200.

Figure 46:
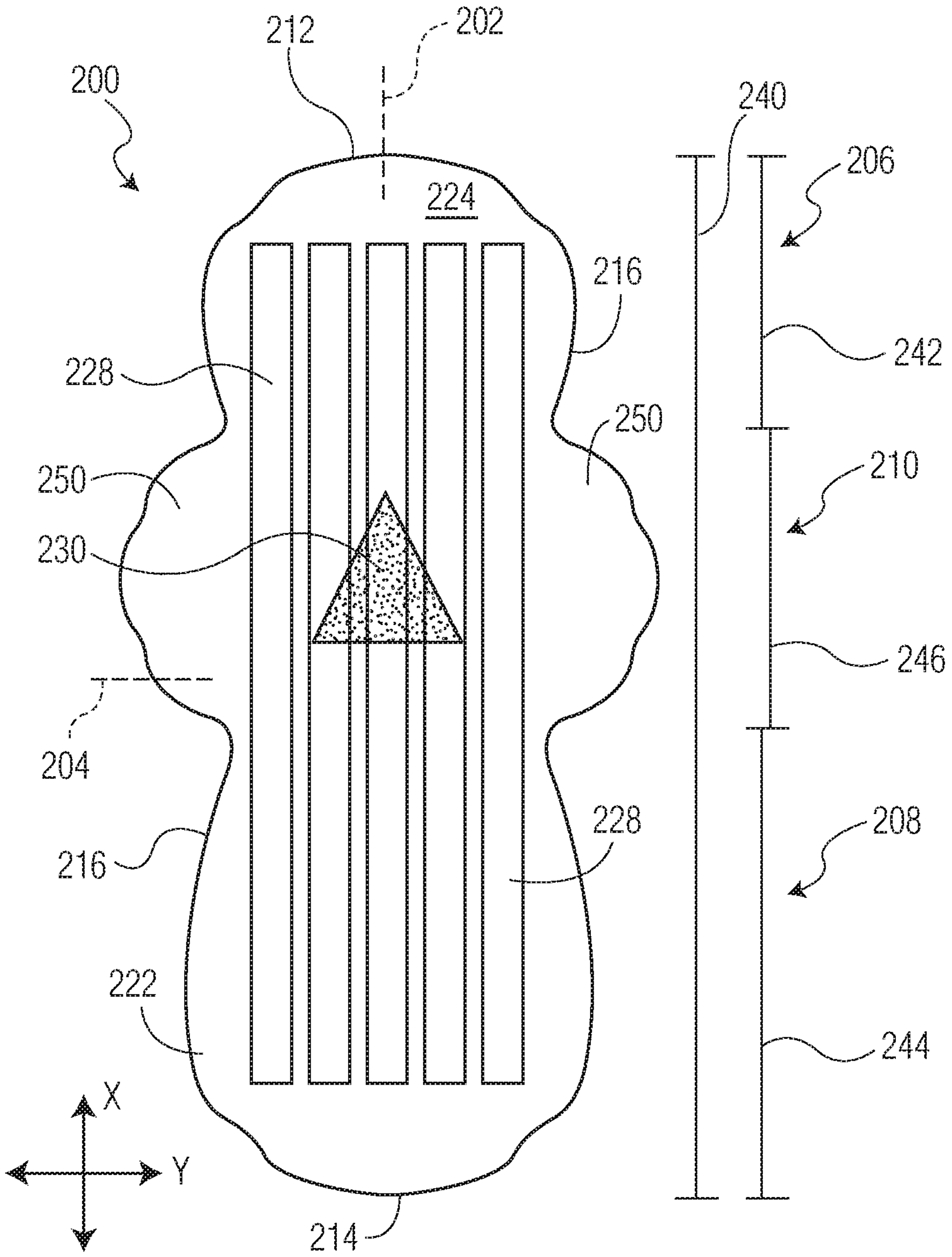
FIGS. 46-49 are bottom views of alternate embodiments of the absorbent article of FIG. 45.

FIG. 46 provides an exemplary illustration of a complementary informational cue 230 located within the crotch region 210 and positioned at the mid-point of the crotch region 210. The complementary informational cue 230 is illustrated in the form of a graphic such as a triangle, however, it is to be understood that the complementary informational cue 230 could be a textural feature or a combination of a graphic and a textural feature. The complementary informational cue 230 can communicate with the wearer of the absorbent article 200 the location of the mid-point of the crotch region 210 of the absorbent article 200 and can also align with an internally visible informational cue, such as internally visible informational cue 100 illustrated in FIG. 28. The wearer of the absorbent article 200 can match the complementary informational cue 230 of the absorbent article 200 to the internally visible informational cue 100 of the pull-on wearable article 10 for proper placement of the absorbent article 200 into the pull-on wearable article 10.

Figure 47:
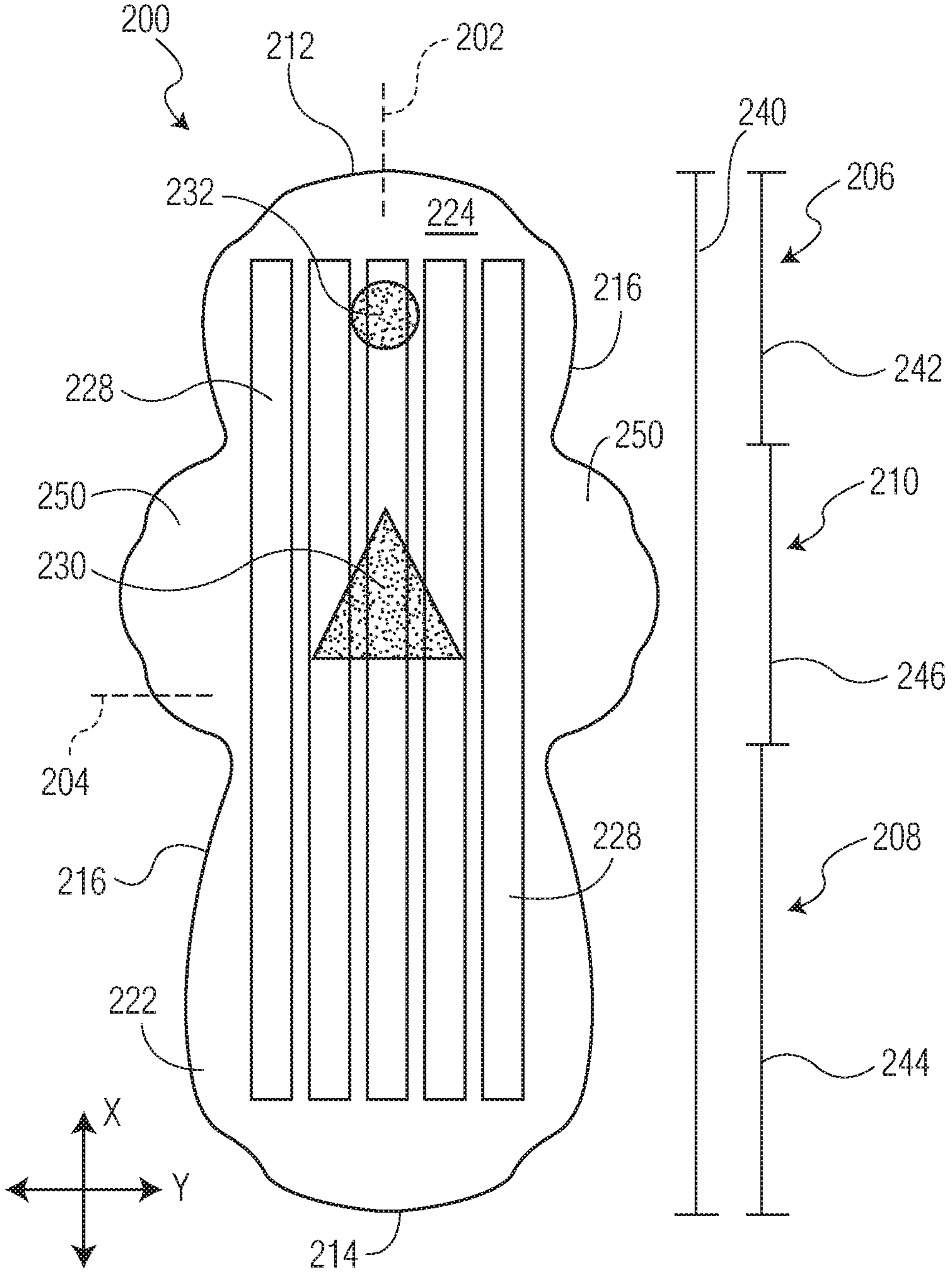

FIG. 47 provides an exemplary illustration of an absorbent article 200 which has two complementary informational cues, a first complementary informational cue 230 and a second complementary informational cue 232. The first complementary informational cue 230 is illustrated in the form of a graphic such as a triangle and is located at the mid-point of the crotch region 210 of the absorbent article 200. The second complementary information cue 232 is illustrated in the form of a graphic such as a circle and is located in the anterior region 206 of the absorbent article 200. It is to be understood that the first complementary informational cue 230 and the second complementary informational cue 232 could be textural features or a combination of a graphic and a textural feature. The first complementary informational cue 230 can communicate with the wearer of the absorbent article 200 the location of the mid-point of the crotch region 210 of the absorbent article 200 and can also align with an internally visible informational cue, such as internally visible informational cue 100 illustrated in FIG. 30. The second complementary informational cue 232 can communicate with the wearer of the absorbent article 200 the location of the anterior region 206 of the absorbent article 200 and can also align with an internally visible informational cue, such as internally visible informational cue 102 illustrated in FIG. 30. The wearer of the absorbent article 200 can match the first complementary informational cue 230 of the absorbent article 200 to the internally visible informational cue 100 of the pull-on wearable article 10 and the second complement informational cue 232 to the internally visible informational cue 102 of the pull-on wearable article 10 for proper placement of the absorbent article 200 into the pull-on wearable article 10.

Figure 48:
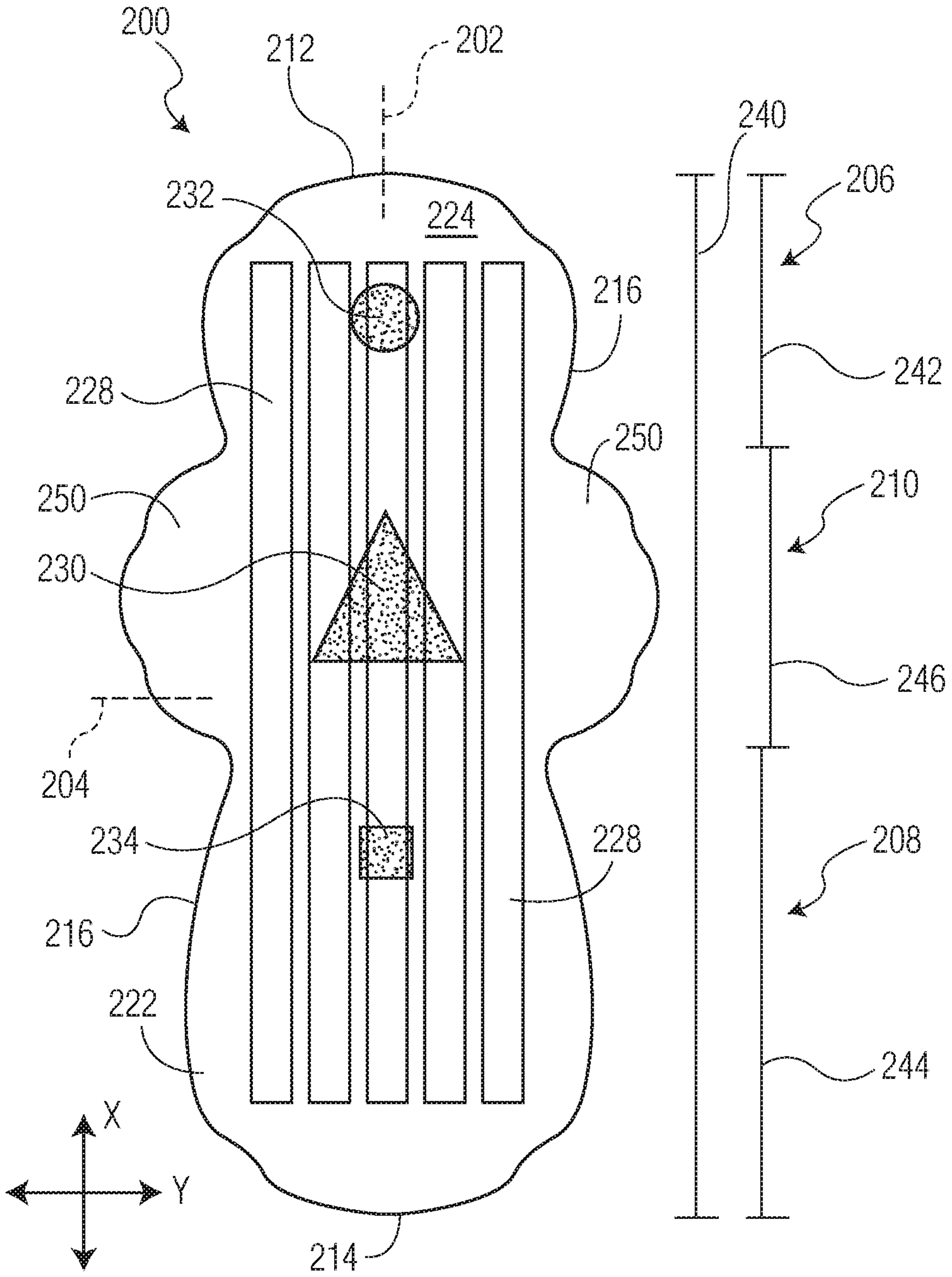

FIG. 48 provides an exemplary illustration of an absorbent article 200 which has three complementary informational cues, a first complementary informational cue 230, a second complementary informational cue 232, and a third complementary informational cue 234. The first complementary informational cue 230 is illustrated in the form of a graphic such as a triangle and is located at the mid-point of the crotch region 210 of the absorbent article 200. The second complementary information cue 232 is illustrated in the form of a graphic such as a circle and is located in the anterior region 206 of the absorbent article 200. The third complementary information cue 234 is illustrated in the form of a graphic such as a square and is located in the posterior region 208 of the absorbent article 200. It is to be understood that the first complementary informational cue 230, the second complementary informational cue 232, and the third complementary cue 234 could be textural features or a combination of a graphic and a textural feature. The first complementary informational cue 230 can communicate with the wearer of the absorbent article 200 the location of the mid-point of the crotch region 210 of the absorbent article 200 and can also align with an internally visible informational cue, such as internally visible informational cue 100 illustrated in FIG. 32. The second complementary informational cue 232 can communicate with the wearer of the absorbent article 200 the location of the anterior region 206 of the absorbent article 200 and can also align with an internally visible informational cue, such as internally visible informational cue 102 illustrated in FIG. 32. The third complementary informational cue 234 can communicate with the wearer of the absorbent article 200 the location of the posterior region 208 of the absorbent article 200 and can also align with an internally visible informational cue, such as internally visible informational cue 104 illustrated in FIG. 32. The wearer of the absorbent article 200 can match the first complementary informational cue 230 of the absorbent article 200 to the internally visible informational cue 100 of the pull-on wearable article 10, the second complement informational cue 232 to the internally visible informational cue 102 of the pull-on wearable article 10, and the third complementary informational cue 234 to the third internally visible informational cue 104 for proper placement of the absorbent article 200 into the pull-on wearable article 10.

Figure 49:
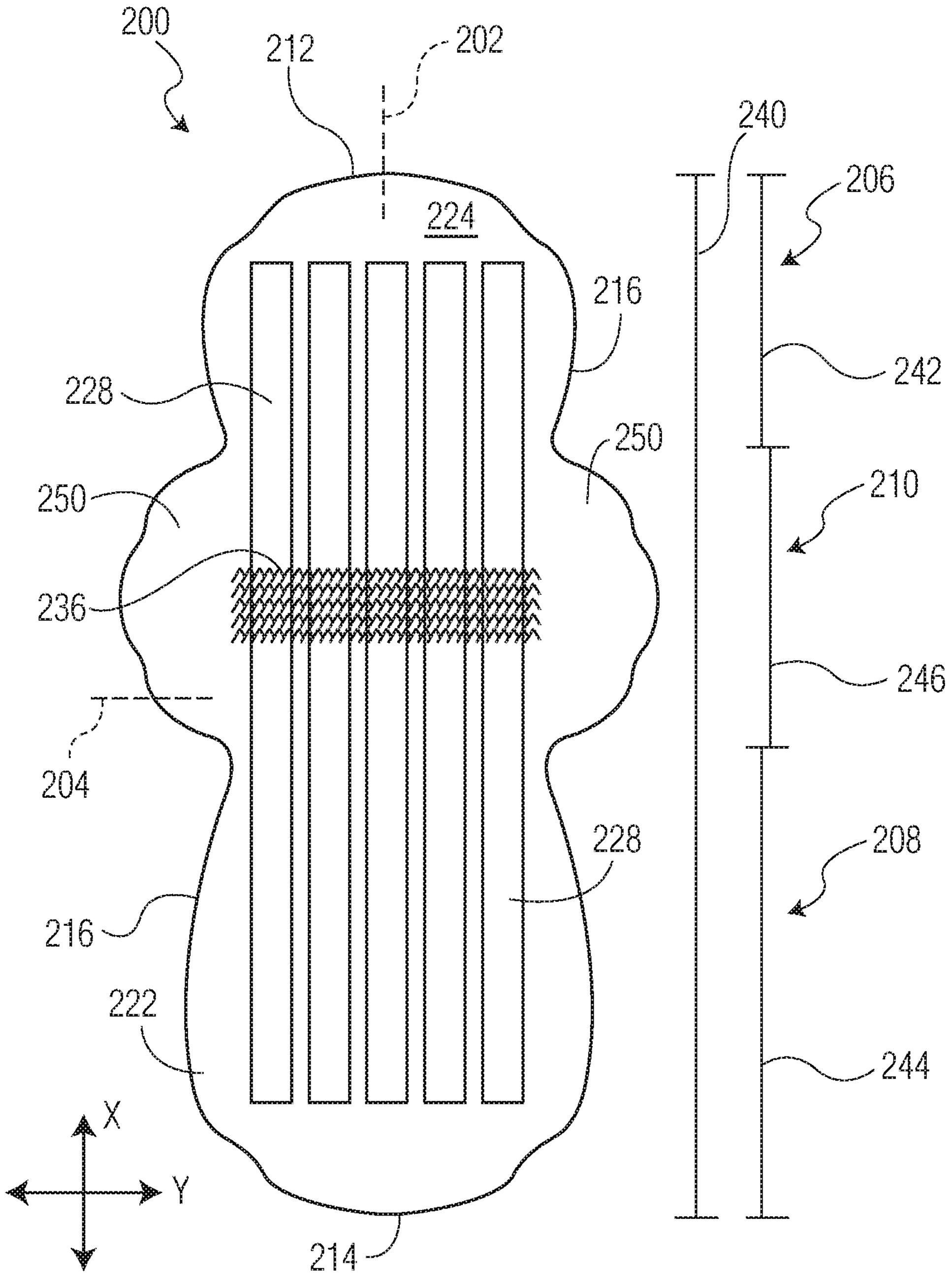

FIG. 49 provides an exemplary illustration of a complementary informational cue 236 located within the crotch region 210 and positioned at the mid-point of the crotch region 210. The complementary informational cue 236 is illustrated in the form of a textural feature, such as, for example, the hooks of a hook-and-loop mating system, however, it is to be understood that the complementary informational cue 236 could be a graphic or a combination of a graphic and a textural feature. The complementary informational cue 236 can communicate with the wearer of the absorbent article 200 the location of the mid-point of the crotch region 210 of the absorbent article 200 and can also align with an internally visible informational cue, such as internally visible informational cue 110 illustrated in FIG. 38. The wearer of the absorbent article 200 can match the complementary informational cue 236 of the absorbent article 200 to the internally visible informational cue 110 of the pull-on wearable article 10 for proper placement of the absorbent article 200 into the pull-on wearable article 10. In various embodiments in which the complementary informational cue 236 is a textural feature, the textural feature can assist in securing the absorbent article 200 to the pull-on wearable article 10. For example, the informational cue 110 and the complementary informational cue 236 can be a hook-and-loop mating system, a snap mating system, a button-and-button hole mating system, etc. For example, the informational cue 110 illustrated in FIG. 38 is a loop portion of a hook-and-loop mating system and the complementary informational cue 236 illustrated in FIG. 44 is the hook portion of a hook-and-loop mating system wherein the two portions, the loop and the hook, can mate to assist in securing the absorbent article 200 to the pull-on wearable article 10.

Referring to FIGS. 45-49 which are exemplary embodiments of an absorbent article 200, in various embodiments, the absorbent article 200 can have a pair of wings 250 extending outwardly, in the transverse direction (Y), from the absorbent article 200. The wings 250 can drape over the edges of the pull-on wearable article 10 so that the wings 250 are disposed between the edges of the wearer's pull-on wearable article 10 and her thighs. The wings 250 can serve at least two purposes. First, the wings 250 can prevent soiling of the wearer's pull-on wearable article 10 by forming a barrier along the edges of the undergarment. Second, the wings 250 can be provided with a fastener, such as, for example, a garment attachment adhesive or a hook, to keep the absorbent article 200 securely and properly positioned in the pull-on wearable article 10. The wings 250 can wrap around the crotch region 40 of the wearer's pull-on wearable article 10 to aid in securing the absorbent article 200 to the wearer's pull-on wearable article 10 when in use. Each wing 250 can fold under the crotch region 40 of the wearer's pull-on wearable article 10 and the fastener can either form a secure attachment to the opposite wing 250 or directly to the non-body facing surface of the wearer's pull-on wearable article 10. In various embodiments in which the pull-on wearable article 10 has an externally visible informational cue located in the crotch region 40 of the pull-on wearable article 10, the wings 250, when present on the absorbent article 200, may be positioned in an at least partially overlapping configuration with the externally visible informational cue of the pull-on wearable article 10. In various embodiments, the wings 250 can be an extension of materials forming the topsheet layer 220 and/or the backsheet layer 222 and can be bonded together along the sealed peripheral region. Such wings 250 can be integrally formed with the main portion of the absorbent article 200. In various embodiments, the wings 250 can be constructed of materials similar to the topsheet layer 220, the backsheet layer 222, or combinations of these materials. In various embodiments, the wings 250 can be separate elements bonded to the main body of the absorbent article 200. Examples of processes for manufacturing absorbent articles 200 and wings 250 include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No. 2004/0040650 to Venturino, et al., and international publication WO1997/040804 to Emenaker, et al., each of which are hereby incorporated by reference thereto in its entirety. It is to be understood that the wings 250 are optional and, in various embodiments, an absorbent article 200 can be configured without wings 80.

Referring to FIG. 50, a top down view of an illustration of an exemplary embodiment of an absorbent article 200 is shown. The absorbent article 200 illustrated in FIG. 50 can have an embossing pattern 260 incorporated therein. In various embodiments, an embossing pattern 260 can be a pattern of depressions downward in a direction towards the absorbent core 226. In various embodiments, an embossing pattern 260 can be a pattern of protrusions upward in a direction away of the from the absorbent core 226. In various embodiments, an embossing pattern 260 can be a combination of a pattern of depressions and protrusions. The embossing pattern 260 can facilitate capture and transport of the body exudates into the absorbent article 200. In various embodiments, it may be deemed suitable for the pull-on wearable article 10 to have an informational cue that fully resembles an absorbent article 200 and the absorbent article embossing pattern 260 to communicate to the wearer of the absorbent article 200 and the pull-on wearable article 10 where to position the absorbent article 200 within the pull-on wearable article 10. For example, referring to FIG. 35, the pull-on wearable article 10 has an internally visible informational cue 100 in the form of a graphic which is an illustrative schematic of an absorbent article in a top down view. As illustrated in the exemplary embodiment of FIG. 35, the schematically illustrated absorbent article has a schematic of an embossing pattern that resembles the embossing pattern of the absorbent article 200 illustrated in FIG. 50. The internally visible informational cue 100 has a first portion 100A located within the crotch region 40, a second portion 100B located within a portion of the front region 20, and a third portion 100C located within a portion of the back region 30 of the pull-on wearable article 10. The first portion 100A of the internally visible informational cue 100 schematically illustrates where the crotch region 210 of the absorbent article 200 should be positioned while each of the second portion 100B of the internally visible informational cue 100 and the third portion 100C of the internally visible informational cue 100 schematically illustrates wherein the anterior region 206 and the posterior region 208 of the absorbent article 200 should be positioned. In such embodiments, a wearer of each of the absorbent article 200 need only match the absorbent article 200 to the internally visible informational cue 100 to result in proper positioning of the absorbent article 200 in the pull-on wearable article 10.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any documents is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. A system of a pull-on wearable article to be worn in combination with an absorbent article, the system comprising:

a. the pull-on wearable article comprising:
   i. a longitudinal direction axis and a transverse direction axis;
   ii. a front region comprising a front waist edge and a back region comprising a back waist edge;
   iii. a crotch region located between the front region and the back region and comprising a narrowest transverse direction region wherein the narrowest transverse direction region is located between the transverse direction axis and the front waist edge;
   iv. a permanent closed waist configuration wherein the pull-on wearable article has a waist opening and two leg openings; and
   v. a first informational cue positioned in the crotch region, at least a portion of the first informational cue in an overlapping configuration with at least a portion of the narrowest transverse direction region, wherein the first informational cue communicates to a wearer of the pull-on wearable article where to place the absorbent article within the pull-on wearable article;

b. the absorbent article comprising:

i. a longitudinal direction axis and a transverse direction axis;

ii. an anterior region, a posterior region, and a crotch region located between the anterior region and the posterior region;

iii. a topsheet layer, a backsheet layer, and an absorbent core positioned between the topsheet layer and the backsheet layer; and iv. a first complementary informational cue located at a mid-point of the crotch region of the absorbent article and associated with the backsheet layer, wherein the first complementary informational cue has an embossing pattern which is combination of a pattern of depressions and protrusions, and wherein the first informational cue has a shape of the embossing pattern, wherein the first informational cue of the pull-on wearable article is internally visible, wherein the absorbent article further comprises a pair of wings, wherein the pull-on wearable article further comprises a second informational cue wherein the second informational cue is externally visible, wherein the second informational cue is in a form of a pair of multi-domed shapes to schematically represent the pair of wings and a location within the crotch region of the pull-on wearable article where the pair of wings should be placed.

2. The system of claim 1 wherein the first informational cue of the pull-on wearable article has a first portion located within a portion of the crotch region of the pull-on wearable article and a second portion located within a portion of the front region of the pull-on wearable article.

3. The system of claim 1 wherein the pull-on wearable article further comprises a second informational cue wherein the second informational cue is located in the front region of the pull-on wearable article.

4. The system of claim 3 wherein the pull-on wearable article further comprises a third informational cue wherein the third informational cue is located in the back region of the pull-on wearable article.

5. The system of claim 1 wherein the first informational cue of the pull-on wearable article is a graphic.

6. The system of claim 1 wherein the first informational cue of the pull-on wearable article is a first textural feature.

7. The system of claim 1 wherein the first complementary informational cue of the absorbent article is a second textural feature.

8. The system of claim 7 wherein the second textural feature of the absorbent article mates with the first textural feature of the pull-on wearable article to secure the absorbent article within the pull-on wearable article.

9. The system of claim 1 wherein the first informational cue of the pull-on wearable article is a combination of a graphic and a textural feature.

10. The system of claim 1 wherein the first informational cue of the pull-on wearable article is externally visible.

11. The system of claim 1 wherein the pull-on wearable article is durable.

12. The system of claim 11 wherein the crotch region of the pull-on wearable article comprises an article body layer.

13. The system of claim 11 wherein at least a portion of the crotch region of the pull-on wearable article comprises a wicking layer.

14. The system of claim 13 wherein at least a portion of the crotch region of the pull-on wearable article comprises a liquid impermeable barrier layer.

15. The system of claim 14 wherein at least a portion of the crotch region of the pull-on wearable article comprises an absorbent layer.

16. The system of claim 1 wherein the absorbent article further comprises a second complementary informational cue located in the anterior region of the absorbent article and associated with the backsheet layer.

17. The system of claim 16 wherein the absorbent article further comprises a third complementary informational cue located in the posterior region of the absorbent article and associated with the backsheet layer.

* * * * *